(12) United States Patent
Classon et al.

(10) Patent No.: US 8,642,741 B2
(45) Date of Patent: Feb. 4, 2014

(54) HUMAN ANTIBODIES TO HUMAN TNF-LIKE LIGAND 1A (TL1A)

(75) Inventors: Brendan J. Classon, Seattle, WA (US); Dimitris Skokos, New York, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 13/291,145

(22) Filed: Nov. 8, 2011

(65) Prior Publication Data

US 2012/0114654 A1 May 10, 2012

Related U.S. Application Data

(60) Provisional application No. 61/478,309, filed on Apr. 22, 2011, provisional application No. 61/411,276, filed on Nov. 8, 2010.

(51) Int. Cl.

| *A61K 39/395* | (2006.01) |
| *C12N 5/10* | (2006.01) |
| *C12N 15/13* | (2006.01) |
| *C12N 15/79* | (2006.01) |
| *C12N 15/86* | (2006.01) |
| *C07K 14/52* | (2006.01) |

(52) U.S. Cl.
USPC .......... 530/388.23; 530/388.15; 536/23.1; 536/23.53; 424/142.1; 424/152.1; 435/335; 435/252.3; 435/254.11; 435/320.1

(58) Field of Classification Search
None
See application file for complete search history.

(56) References Cited

U.S. PATENT DOCUMENTS

| 6,521,422 | B1 | 2/2003 | Hsu et al. |
| 7,597,886 | B2 | 10/2009 | Yu et al. |
| 7,820,798 | B2 | 10/2010 | Yu et al. |
| 8,263,743 | B2 * | 9/2012 | Smith et al. |
| 2009/0280116 | A1 | 11/2009 | Smith et al. |

OTHER PUBLICATIONS

Bamias et al., High intestinal and systemic levels of decoy receptor 3 (DcR3) and its ligand TL1A in active ulcerative colitis, Clin. Immunol. 137:242-249, Aug. 2010.*

Zhan et al., Biochemical and structural characterization of the human TL1A ectodomain, Biochem. 48:7636-7645, 2009.*
Prehn et al., "The T Cell Costimulator TL1A Is Induced by FcγR Signaling in Human Monocytes and Dendritic Cells", J. Immunol., 2007, 178:4033-4038.
Migone et al., "TL1A Is a TNF-like Ligand for DR3 and TR6/DcR3 and Functions as a T Cell Costimulator", Immunity, 2002, 16:479-492.
Meylan et al., "The Tumor Necrosis Factor-Family Receptor DR3 is Essential for Diverse T-Cell Mediated Inflammatory Diseases", Immunity, 2008, 29:79-89.
Zhai et al., "VEGI, a novel cytokine of the tumor necrosis factor family, is an angiogenesis inhibitor that suppresses the growth of colon carcinomas in vivo", FASEB J., 1999, 13:181-189.
Chew et al., A novel secreted splice variant of vascular endothelial cell growth inhibitor, FASEB J., 2002, 16:742-744.
Yang et al., "Soluble Decoy Receptor 3 Induces Angiogenesis by Neutralization of TL1A, a Cytokine Belonging to Tumor Necrosis Factor Superfamily and Exhibiting Angiostatic Action", Cancer Res., 2004, 64:1122-1129.
Screaton et al., "LARD: A new lymphoid-specific death domain containing receptor regulated by alternative pre-mRNA splicing", Proc. Natl. Acad. Sci. (USA), 1997, 94:4615-4619.
Bayry, "TL1A in the inflammatory network in autoimmune diseases", Nature Reviews/Rheumatology, 2010, 6:67-68.
Takedatsu et al., "TL1A (TNFSF15) Regulates the Development of Chronic Colitis by Modulating both T helper (TH) 1 and TH17 Activation", Gastroenterology, 2008, 135:552-567.
Pappu et al., TL1A DR3 interaction regulates Th17 cell function and Th17-mediated autoimmune disease, J. Exp. Med., 2008, 205:1049-1062.
Bamias et al., "Circulating levels of TNF-like cytokine 1A (TL1A) and its decoy receptor 3 (DcR 3) in rheumatoid arthritis", Clin. Immunol., 2008, 129:249-255.
Fang et al., "Essential role of TNF receptor superfamily 25 (TNFRSF25) in the development of allergic lung inflammation", J. Exp. Med., 2008, 205:1037-1048.

* cited by examiner

*Primary Examiner* — Claire Kaufman
(74) *Attorney, Agent, or Firm* — Veronica Mallon; Regeneron Pharmaceuticals, Inc.

(57) ABSTRACT

A fully human antibody or antigen-binding fragment of a human antibody that specifically binds and inhibits human TNF-like ligand 1A (hTL1A) is provided. The human anti-hTL1A antibodies are useful in treating diseases or disorders associated with TL1A, such as inflammatory diseases or disorders, e.g., inflammatory bowel diseases, including ulcerative colitis and Crohn's disease, rheumatoid arthritis, and the like; autoimmune diseases or disorders, such as multiple sclerosis, diabetes, and the like; and allergic reactions, such as asthma and allergic lung inflammation.

13 Claims, No Drawings

HUMAN ANTIBODIES TO HUMAN TNF-LIKE LIGAND 1A (TL1A)

CROSS-REFERENCE TO RELATED APPLICATIONS

This application claims the benefit under 35 U.S.C §119(e) of U.S. provisional application Nos. 61/411,276 filed Nov. 8, 2010; and 61/478,309 filed Apr. 22, 2011, both of which are herein specifically incorporated by reference in their entireties.

FIELD OF THE INVENTION

The present invention is related to human antibodies and antigen-binding fragments of human antibodies that specifically bind human TNF-like ligand 1A (hTL1A), and therapeutic methods of using those antibodies.

STATEMENT OF RELATED ART

TL1A is a type II cell membrane protein of the tumor necrosis factor superfamily (TNFSF) and also designated as TNFSF15. It is expressed on the surface of endothelial cells, and activated cells of the hematopoietic lineage, including monocytes, macrophages, lymphocytes, lamina propria mononuclear cells, dendritic cells and plasma cells (Tan, K. B. et al., 1997, *Gene* 204:35-46; Prehn, J. L. et al., 2007, *J Immunol* 178:4033-4038). It is also expressed in kidney, lung, prostate and thymus (Tan et al., 1997, supra). In endothelial cells, expression of TL1A is upregulated by IL-1α and TNFα (Migone, T. S. et al., 2002, *Immunity* 16:479-492). In human fresh blood monocytes and monocyte-derived dendritic cells, TL1A expression is upregulated by FcγR-mediated or Toll-like receptor (TLR) signaling (Prehn et al., 2007, supra; Meylan, F. et al., 2008, *Immunity* 29:79-89). TL1A can be cleaved from the cell membrane via a mechanism analogous to TNFα and a soluble ectodomain form of TL1A has been reported (Migone et al., 2002, supra; Kim, S. et al., 2005, *J Immunol Methods* 298:1-8; Yang, C. R. et al., 2004, *Cancer Res* 64:1122-1129). Protein sequencing has confirmed that this form of TL1A is liberated following cleavage of the membrane-anchored precursor between residues Ala-71 and Leu-72 (Migone et al., 2002, supra). Two variant cDNAs that potentially encode N-terminally truncated versions of TL1A have been identified: VEGI-174 (or TL1) (Zhai, Y. et al., 1999, *FASEB J* 13:181-189) and VEGI-192 (Chew, L. J. et al., 2002, *FASEB J* 16:742-744). The published data suggest the biologically active products of the TL1A gene are the full-length type II transmembrane protein (residues 1-251) and its proteolytically cleaved ectodomain (residues 72-251) (Migone et al., 2002, supra; Jin et al., 2007, *Biochem Biophys Res Commun* 364:1-6). A variant of hTL1A, designated as "Fhm", containing a single amino acid substitution of Gln-167 with Arg, is disclosed in U.S. Pat. No. 6,521,422.

TL1A mediates signals via its cognate receptor Death Receptor 3 (DR3; also known as TNFRSF25; the nucleic acid and amino acid sequences of SEQ ID NO:251 and 252, respectively), resulting in promoting cell survival and secretion of pro-inflammatory cytokines, or promoting apoptosis, in a context-dependent manner. TL1A is one of three known ligands (in addition to FasL and LIGHT) that are bound by the endogenous soluble decoy receptor, DcR3 (also known as TR6, NTR3 or TNFRSF21; the nucleic acid and amino acid sequences of SEQ ID NO:253 and 254, respectively) (Migone et al., 2002, supra; Yang C. R. et al., 2004, *Cancer Res* 64:1122-1129). DR3 is a TNF receptor-related death-domain receptor expressed on the majority of activated T lymphocytes and NK cells (Migone et al., 2002, supra; Screaton G. R. et al., 1997, *Proc Natl Acad Sci (USA)* 94:4615-4619). TL1A engages DR3 on T cells, enhancing their responsiveness to IL-2 (Migone et al., 2002, supra), potentiating T cell proliferation and release of IFN$_7$ and GM-CSF under conditions of suboptimal costimulation (Migone et al., 2002, supra; Meylan et al., 2008, supra). TL1A has also been shown to synergize with suboptimal levels of IL-12/IL-18 to induce IFNγ production by CD4$^+$ T cells (Papadakis, K. A. et al., 2004, *J Immuno/*172:7002-7007; Prehn, J. L. et al., 2004, *Clin Immunol* 112:66-77; Papadakis, K. A. et al., 2005, *J Immunol* 174:4985-4990; Cassatella, M. A. et al., 2007, *J Immunol* 178:7325-7333).

TL1A has been implicated in various inflammatory diseases and/or auto immune diseases, including inflammatory bowel diseases [e.g., ulcerative colitis (UC) and Crohn's disease (CD)], rheumatoid arthritis, multiple sclerosis (MS), atherosclerosis, and the like (see Bayry, J., 2010, *Nature Reviews/Rheumatology* 6:67-68; Takedatsu, H. et al., 2008, *Gastroenterology* 135:552-567; Prehn et al., 2004, supra; Bamias, G. et al., 2008, *Clin Immunol* 129:249-255; Bull, M. J. et al., 2008, *J Exp Med* 205:2457-2464; Pappu, B. P. et al., 2008, *J Exp Med* 205:1049-1062; Bamias, G. et al., 2003, *J Immuno/*171:4868-4874; Kang, Y. et al., 2005, *Cytokine* 29:229-235). Although the majority of the published data are consistent with a pivotal role for TL1A in driving differentiation of $T_H1$ and $T_H17$ effector function, a recent study has proposed a role for the TL1A/DR3 interaction in development of $T_H2$ T cell responses in asthma models (Fang, L. et al., 2008, *J Exp Med* 205:1037-1048). Thus, the use of TL1A inhibitors, such as fully human antibodies against TL1A with high affinities and neutralizing activity, alone or in combination with currently available anti-inflammatory agents, immunosuppressants (e.g., TNF-α antagonists, cortisone or steroids, and the like), and/or anti-allergy agents, provides effective treatment for these diseases and disorders.

The nucleic acid and the amino acid sequences of human TL1A are shown in SEQ ID NOS: 243 and 244, respectively, and those of Fhm are shown in SEQ ID NOS:245 and 246, respectively. Antibodies to TL1A are disclosed in, for example, US 7,597,886, US 7,820,798 and US 2009/0280116.

BRIEF SUMMARY OF THE INVENTION

In a first aspect, the invention provides fully human monoclonal antibodies (mAbs) and antigen-binding fragments thereof that specifically bind and neutralize human TL1A (hTL1A) activity.

The antibodies can be full-length (for example, an IgG1 or IgG4 antibody) or may comprise only an antigen-binding portion (for example, a Fab, F(ab)$_2$ or scFv fragment), and may be modified to affect functionality, e.g., to eliminate residual effector functions (Reddy et al., 2000, *J. Immunol* 164:1925-1933).

In one embodiment, the invention features an antibody or antigen-binding fragment of an antibody comprising a heavy chain variable region (HCVR) selected from the group consisting of SEQ ID NO:2, 18, 34, 50, 66, 82, 98, 114, 118, 134, 138, 154, 158, 174, 178, 194, 198, 214, 218 and 234, or a substantially similar sequence thereof having at least 90%, at least 95%, at least 98% or at least 99% sequence identity. In another embodiment, the antibody or an antigen-binding fragment thereof comprises a HCVR having an amino acid sequence selected from the group consisting of SEQ ID NO:2, 18, 34, 50, 66, 134, 174 and 234. In yet another embodiment, the antibody or fragment thereof comprises a HCVR comprising SEQ ID NO:2, 18, 174 or 234.

In one embodiment, the antibody or fragment thereof further comprises a light chain variable region (LCVR) selected from the group consisting of SEQ ID NO:10, 26, 42, 58, 74, 90, 106, 116, 126, 136, 146, 156, 166, 176, 186, 196, 206, 216, 226 and 236, or a substantially similar sequence thereof having at least 90%, at least 95%, at least 98% or at least 99% sequence identity. In another embodiment, the antibody or antigen-binding portion of an antibody comprises a LCVR having an amino acid sequence selected from the group consisting of SEQ ID NO:10, 26, 42, 58, 74, 136, 176 and 236. In yet another embodiment, the antibody or fragment thereof comprises a LCVR comprising SEQ ID NO:10, 26, 176 or 236.

In further embodiments, the antibody or fragment thereof comprises a HCVR and LCVR (HCVR/LCVR) sequence pair selected from the group consisting of SEQ ID NO:2/10, 18/26, 34/42, 50/58, 66/74, 82/90, 98/106, 114/116, 118/126, 134/136, 138/146, 154/156, 158/166, 174/176, 178/186, 194/196, 198/206, 214/216, 218/226 and 234/236. In one embodiment, the antibody or fragment thereof comprises a HCVR and LCVR selected from the amino acid sequence pairs of SEQ ID NO:2/10, 18/26, 34/42, 50/58, 66/74, 134/136, 174/176 and 234/236. In another embodiment, the antibody or fragment thereof comprises a HCVR/LCVR pair comprising SEQ ID NO:2/10, 18/26, 174/176 or 234/236.

In a second aspect, the invention features an antibody or antigen-binding fragment of an antibody comprising a heavy chain complementarity determining region 3 (HCDR3) amino acid sequence selected from the group consisting of SEQ ID NO:8, 24, 40, 56, 72, 88, 104, 124, 144, 164, 184, 204 and 224, or a substantially similar sequence thereof having at least 90%, at least 95%, at least 98% or at least 99% sequence identity; and a light chain CDR3 (LCDR3) amino acid sequence selected from the group consisting of SEQ ID NO:16, 32, 48, 64, 80, 96, 112, 132, 152, 172, 192, 212 and 232, or substantially similar sequences thereof having at least 90%, at least 95%, at least 98% or at least 99% sequence identity. In one embodiment, the antibody or fragment thereof comprises a HCDR3/LCDR3 amino acid sequence pair comprising SEQ ID NO:8/16, 24/32, 40/48, 56/64, 72/80, 88/96, 104/112, 124/132, 144/152, 164/172, 184/192, 204/212 or 224/232. In another embodiment, the antibody or fragment thereof comprises a HCDR3/LCDR3 amino acid sequence pair comprising SEQ ID NO: 8/16, 24/32, 40/48, 56/64, 72/80, 124/132, 164/172 or 224/232. In yet another embodiment, the antibody or fragment thereof comprises a HCDR3/LCDR3 amino acid sequence pair comprising SEQ ID NO:8/16, 24/32, 164/172 or 224/232.

In a further embodiment, the invention features an antibody or fragment thereof further comprising a heavy chain CDR1 (HCDR1) amino acid sequence selected from the group consisting of SEQ ID NO:4, 20, 36, 52, 68, 84, 100, 120, 140, 160, 180, 200 and 220, or a substantially similar sequence thereof having at least 90%, at least 95%, at least 98% or at least 99% sequence identity; a heavy chain CDR2 (HCDR2) amino acid sequence selected from the group consisting of SEQ ID NO:6, 22, 38, 54, 70, 86, 102, 122, 142, 162, 182, 202 and 222, or a substantially similar sequence thereof having at least 90%, at least 95%, at least 98% or at least 99% sequence identity; and/or a light chain CDR1 (LCDR1) amino acid sequence selected from the group consisting of SEQ ID NO:12, 28, 44, 60, 76, 92, 108, 128, 148, 168, 188, 208 and 228, or a substantially similar sequence thereof having at least 90%, at least 95%, at least 98% or at least 99% sequence identity; and/or a light chain CDR2 (LCDR2) amino acid sequence selected from the group consisting of SEQ ID NO:14, 30, 46, 62, 78, 94, 110, 130, 150, 170, 190, 210 and 230, or a substantially similar sequence thereof having at least 90%, at least 95%, at least 98% or at least 99% sequence identity. In one embodiment, the antibody or fragment thereof comprises a combination of HCDR1/HCDR2/HCDR3 selected from the group consisting of SEQ ID NO:4/6/8, 20/22/24, 36/38/40, 52/54/56, 68/70/72, 84/86/88, 100/102/104, 120/122/124, 140/142/144, 160/162/164, 180/182/184, 200/202/204 and 220/222/224; and/or a combination of LCDR1/LCDR2/LCDR3 selected from the group consisting of 6SEQ ID NO:12/14/16, 28/30/32, 44/46/48, 60/62/64, 76/78/80, 92/94/96, 108/110/112, 128/130/132, 148/150/152, 168/170/172, 188/190/192, 208/210/212 and 228/230/232. In another embodiment, the heavy and light chain CDR amino acid sequences comprise a CDR sequence combination selected from the group consisting of SEQ ID NO:4/6/8/12/14/16, 20/22/24/28/30/32, 36/38/40/44/46/48, 52/54/56/60/62/64, 68/70/72/76/78/80, 84/86/88/92/94/96, 100/102/104/108/110/112, 120/122/124/128/130/132, 140/142/144/148/150/152, 160/162/164/168/170/172, 180/182/184/188/190/192, 200/202/204/208/210/212 and 220/222/224/228/230/232. In another embodiment, the antibody or antigen-binding fragment thereof comprises heavy and light chain CDR sequences of SEQ ID NO:4/6/8/12/14/16, 20/22/24/28/30/32, 36/38/40/44/46/48, 52/54/56/60/62/64, 68/70/72/76/78/80, 120/122/124/128/130/132, 160/162/164/168/170/172 or 220/222/224/228/230/232. In yet another embodiment, the heavy and light chain CDR amino acid sequences comprise a CDR sequence combination of SEQ ID NO:4/6/8/12/14/16, 20/22/24/28/30/32, 160/162/164/168/170/172 or 220/222/224/228/230/232.

In a related embodiment, the invention comprises an antibody or antigen-binding fragment of an antibody which specifically binds hTL1A, wherein the antibody or fragment thereof comprises heavy and light CDR domains contained within heavy and light chain sequence pairs selected from the group consisting of SEQ ID NO:2/10, 18/26, 34/42, 50/58, 66/74, 82/90, 98/106, 114/116, 118/126, 134/136, 138/146, 154/156, 158/166, 174/176, 178/186, 194/196, 198/206, 214/216, 218/226 and 234/236. Methods and techniques for identifying CDRs within HCVR and LCVR amino acid sequences are known in the art and can be applied to identify CDRs within the specified HCVR and/or LCVR amino acid sequences disclosed herein. Conventional definitions that can be applied to identify the boundaries of CDRs include the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., *J. Mol. Biol.* 273:927-948 (1997); and Martin et al., *Proc. Natl. Acad. Sci. USA* 86:9268-9272 (1989). Public databases are also available for identifying CDR sequences within an antibody. In one embodiment, the antibody or fragment thereof comprises CDR sequences contained within a HCVR and LCVR pair selected from the group consisting of the amino acid sequence pairs of SEQ ID NO:2/10, 18/26, 34/42, 50/58, 66/74, 134/136, 174/176 and 234/236. In another embodiment, the antibody or fragment thereof comprises CDR sequences contained within the HCVR and LCVR sequence pair of SEQ ID NO: 2/10, 18/26, 174/176 or 234/236.

In another related embodiment, the invention provides an antibody or antigen-binding fragment thereof that competes for specific binding to hTL1A with an antibody or antigen-binding fragment comprising heavy and light chain CDR sequences of SEQ ID NO:4/6/8/12/14/16, 20/22/24/28/30/32, 36/38/40/44/46/48, 52/54/56/60/62/64, 68/70/72/76/78/80, 120/122/124/128/130/132, 160/162/164/168/170/172 or 220/222/224/228/230/232. In one embodiment, the antibody or antigen-binding fragment thereof competes for specific binding to hTL1A with an antibody or antigen-binding fragment comprising heavy and light chain CDR sequences of SEQ ID NO:4/6/8/12/14/16, 20/22/24/28/30/32, 160/162/164/168/170/172 or 220/222/224/228/230/232. In another embodiment, the antibody or antigen-binding fragment of the invention competes for specific binding to hTL1A with an antibody or antigen-binding fragment comprising a HCVR/LCVR sequence pair of SEQ ID NO:2/10, 18/26, 34/42, 50/58, 66/74, 134/136, 174/176 or 234/236. In yet another embodiment, the antibody or antigen-binding fragment thereof competes for specific binding to hTL1A with an antibody or antigen-binding fragment comprising a HCVR/LCVR sequence pair of SEQ ID NO:2/10, 18/26, 174/176 or 234/236.

In another related embodiment, the invention provides an antibody or antigen-binding fragment thereof that binds the same epitope on hTL1A that is recognized by an antibody or fragment thereof comprising heavy and light chain CDR sequences of SEQ ID NO:4/6/8/12/14/16, 20/22/24/28/30/32, 36/38/40/44/46/48, 52/54/56/60/62/64, 68/70/72/76/78/80, 120/122/124/128/130/132, 160/162/164/168/170/172 or 220/222/224/228/230/232. In one embodiment, the antibody or antigen-binding fragment thereof binds the same epitope on hTL1A that is recognized by an antibody or antigen-binding fragment thereof comprising heavy and light chain CDR sequences of SEQ ID NO:4/6/8/12/14/16, 20/22/24/28/30/32, 160/162/164/168/170/172 or 220/222/224/228/230/232. In another embodiment, the antibody or antigen-binding fragment of the invention recognizes the same epitope on hTL1A that is recognized by an antibody or antigen-binding fragment thereof comprising a HCVR/LCVR sequence pair of SEQ ID NO: SEQ ID NO:2/10, 18/26, 34/42, 50/58, 66/74, 134/136, 174/176 or 234/236. In yet another embodiment, the antibody or antigen-binding fragment thereof recognizes the same epitope on hTL1A that is recognized by an antibody or antigen-binidng fragment thereof comprising a HCVR/LCVR sequence pair of SEQ ID NO:2/10, 18/26, 174/176 or 234/236.

In a third aspect, the invention provides nucleic acid molecules encoding anti-TL1A antibodies or fragments thereof described above. Recombinant expression vectors carrying the nucleic acids of the invention, and isolated host cells, e.g., bacterial cells, such as E. coli, or mammalian cells, such as CHO cells, into which such vectors have been introduced, are also encompassed by the invention, as are methods of producing the antibodies by culturing the host cells under conditions permitting production of the antibodies, and recovering the antibodies produced.

In one embodiment, the invention provides an antibody or fragment thereof comprising a HCVR encoded by a nucleic acid sequence selected from the group consisting of SEQ ID NO:1, 17, 33, 49, 65, 81, 97, 113, 117, 133, 137, 153, 157, 173, 177, 193, 197, 213, 217 and 233, or a substantially identical sequence having at least 90%, at least 95%, at least 98%, or at least 99% homology thereof. In another embodiment, the antibody or fragment thereof comprises a HCVR encoded by a nucleic acid sequence selected from the group consisting of SEQ ID NO:1, 17, 33, 49, 65, 133, 173 and 233. In yet another embodiment, the antibody or fragment thereof comprises a HCVR encoded by the nucleic acid sequence of SEQ ID NO:1, 17, 173 or 233.

In one embodiment, the antibody or fragment thereof further comprises a LCVR encoded by a nucleic acid sequence selected from the group consisting of SEQ ID NO:9, 25, 41, 57, 73, 89, 105, 115, 125, 135, 145, 155, 165, 175, 185, 195, 205, 215, 225 and 235, or a substantially identical sequence having at least 90%, at least 95%, at least 98%, or at least 99% homology thereof. In another embodiment, the antibody or fragment thereof comprises a LCVR encoded by a nucleic acid sequence selected from the group consisting of SEQ ID NO:9, 25, 41, 57, 73, 135, 175 and 235. In yet another embodiment, the antibody or fragment thereof comprises a LCVR encoded by the nucleic acid sequence of SEQ ID NO:9, 25, 175 or 235.

In further embodiments, the antibody or fragment thereof comprises a HCVR and LCVR (HCVR/LCVR) sequence pair encoded by a nucleic acid sequence pair selected from the group consisting of SEQ ID NO:1/9, 17/25, 33/41, 49/57, 65/73, 81/89, 97/105, 113/115, 117/125, 133/135, 137/145, 153/155, 157/165, 173/175, 177/185, 193/195, 197/205, 213/215, 217/225 and 233/235. In one embodiment, the antibody or fragment thereof comprises a HCVR/LCVR sequence pair encoded by a nucleic acid sequence pair selected from the group consisting of SEQ ID NO:1/9, 17/25, 33/41, 49/57, 65/73, 133/135, 173/175 and 233/235. In yet another embodiment, the antibody or fragment thereof comprises a HCVR/LCVR pair encoded by a nucleic acid sequence pair of SEQ ID NO:1/9, 17/25, 173/175 or 233/235.

In one embodiment, the invention features an antibody or antigen-binding fragment of an antibody comprising a HCDR3 domain encoded by a nucleotide sequence selected from the group consisting of SEQ ID NO:7, 23, 39, 55, 71, 87, 103, 123, 143, 163, 183, 203 and 223, or a substantially identical sequence having at least 90%, at least 95%, at least 98%, or at least 99% homology thereof; and a LCDR3 domain encoded by a nucleotide sequence selected from the group consisting of SEQ ID NO:15, 31, 47, 63, 79, 95, 111, 131, 151, 171, 191, 211 and 231, or a substantially identical sequence having at least 90%, at least 95%, at least 98%, or at least 99% homology thereof. In another embodiment, the antibody or fragment thereof comprises a HCDR3 and LCDR3 sequence pair encoded by the nucleic acid sequence pair of SEQ ID NO:7/15, 23/31, 39/47, 55/63, 71/79, 87/95, 103/111, 123/131, 143/151, 163/171, 183/191, 203/211 or 223/231. In another embodiment, the antibody or fragment thereof comprises a HCDR3 and LCDR3 sequence pair encoded by the nucleic acid sequence pair of SEQ ID NO:7/15, 23/31, 39/47, 55/63, 71/79, 123/131, 163/171 or 223/231. In yet another embodiment, the HCDR3/LCDR3 sequence pair is encoded by the nucleic acid sequence pair of SEQ ID NO:7/15, 23/31, 163/171 or 223/231.

In a further embodiment, the antibody or fragment thereof further comprises, a HCDR1 domain encoded by a nucleotide sequence selected from the group consisting of SEQ ID NO:3, 19, 35, 51, 67, 83, 99, 119, 139, 159, 179, 199 and 219, or a substantially identical sequence having at least 90%, at least 95%, at least 98%, or at least 99% homology thereof; a HCDR2 domain encoded by a nucleotide sequence selected from the group consisting of SEQ ID NO:5, 21, 37, 53, 69, 85, 101, 121, 141, 161, 181, 201 and 221, or a substantially identical sequence having at least 90%, at least 95%, at least 98%, or at least 99% homology thereof; a LCDR1 domain encoded by a nucleotide sequence selected from the group consisting of SEQ ID NO:11, 27, 43, 59, 75, 91, 107, 127, 147, 167, 187, 207 and 227, or a substantially identical sequence having at least 90%, at least 95%, at least 98%, or at least 99% homology thereof; and a LCDR2 domain encoded by a nucleotide sequence selected from the group consisting of SEQ ID NO:13, 29, 45, 61, 77, 93, 109, 129, 149, 169, 189, 209 and 229, or a substantially identical sequence having at least 90%, at least 95%, at least 98%, or at least 99% homology thereof. In one embodiment, the antibody or fragment thereof comprises a combination of HCDR1/HCDR2/HCDR3 encoded by SEQ ID NO:3/5/7, 19/21/23, 35/37/39, 51/53/55, 67/69/71, 83/85/87, 99/101/103, 119/121/123, 139/141/143, 159/161/163, 179/181/183, 199/201/203 or 219/221/223; and a combination of LCDR1/LCDR2/LCDR3 encoded by SEQ ID NO:11/13/15, 27/29/31, 43/45/47, 59/61/63, 75/77/79, 91/93/95, 107/109/111, 127/129/131, 147/149/151, 167/169/171, 187/189/191, 207/209/211 or 227/229/231. In one embodiment, the antibody or fragment thereof comprises heavy and light chain CDR sequences encoded by a nucleic acid sequence combination selected from the group consisting of SEQ ID NO:3/5/7/11/13/15, 19/21/23/27/29/31, 35/37/39/43/45/47, 51/53/55/59/61/63, 67/69/71/75/77/79, 83/85/87/91/93/95, 99/101/103/107/109/111, 119/121/123/127/129/131, 139/141/143/147/149/151, 159/161/163/167/169/171, 179/181/183/187/189/191, 199/201/203/207/209/211 and 219/221/223/227/229/231. In another embodiment, the antibody or antigen-binding portion thereof comprises heavy and light chain CDR sequences encoded by a nucleic acid sequence combination of SEQ ID NO:3/5/7/11/13/15, 19/21/23/27/29/31, 35/37/39/43/45/47, 51/53/55/59/61/63, 67/69/71/75/77/79, 119/121/123/127/129/131, 159/161/163/167/169/171 or 219/221/223/227/229/231. In yet another embodiment, the antibody or antigen-binding portion thereof comprises heavy and light chain CDR sequences encoded by a nucleic acid sequence combination of SEQ ID NO: 3/5/7/11/13/15, 19/21/23/27/29/31, 159/161/163/167/169/171 or 219/221/223/227/229/231.

In a fourth aspect, the invention features an isolated antibody or antigen-binding fragment of an antibody that specifically binds hTL1A, comprising a HCDR3 and a LCDR3, wherein the HCDR3 comprises an amino acid sequence of the formula $X^1$-$X^2$-$x^3$-$X^4$-$X^5$-$X^6$-$x^7$-$X^8$-$X^9$-$X^{10}$ $^{l-x}$11-x12-13-x14-x15-X16 (SEQ ID NO:239), wherein $X^1$ is Thr or Ala, $X^2$ is Lys, Arg or absent, $X^3$ is Glu, Gly or absent, $X^4$ is Asp, Pro or absent, $X^5$ is Leu or absent, $X^6$ is Arg, Tyr, Glu or absent, $X^7$ is Gly, Asp, Ala or absent, $X^8$ is Asp, Ser or Tyr, $X^9$ is Tyr or Trp, $X^{10}$ is Tyr or Asp, $X^{11}$ is Tyr, Lys or Ile, $X^{12}$ is Gly, Tyr, Asn, or Ser, $X^{13}$ is Val, Gly or Ser, $X^{14}$ is Phe or Met, $X^{15}$ is Asp, and $X^{16}$ is Tyr or Val; and the LCDR3 comprises an amino acid sequence of the formula $X^1$-$X^2$-$X^3$-$X^4$-$X^5$-$X^6$-$X^7$-$X^8$-$X^9$ (SEQ ID NO:242), wherein $X^1$ is Gln, $X^2$ is Gln, $X^3$ is Tyr, Leu or Phe, $X^4$ is His, Tyr or Asn, $X^5$ is Arg or Ser, $X^6$ is Ser, Thr or Tyr, $X^7$ is Trp or Pro, $X^8$ is Phe, Leu or absent, and $X^9$ is Thr.

In a further embodiment, the antibody or fragment thereof further comprises a HCDR1 sequence comprising an amino acid sequence of the formula $X^1$-$X^2$-$X^3$-$X^4$-$X^5$-$X^6$-$X^7$-$X^8$ (SEQ ID NO:237), wherein $X^1$ is Gly, $X^2$ is Phe, $X^3$ is Thr, $X^4$ is Phe, $X^5$ is Ser, $X^6$ is Thr, Ser or Asn, $X^7$ is Tyr, and $X^8$ is Gly, Trp, Val or Ala; a HCDR2 sequence comprising an amino acid sequence of the formula $X^1$-$X^2$-$X^3$-$X^4$-$X^5$-$X^6$-$X^7$-$X^8$ (SEQ ID NO:238), wherein $X^1$ is Ile or Val, $X^2$ is Ser or Lys, $X^3$ is Gly or Glu, $X^4$ is Thr, Asp, Ser or Arg, $X^5$ is Gly, $X^6$ is Arg, Ser or Gly, $X^7$ is Thr, Glu or Ser, and $X^8$ is Thr or Lys; a LCDR1 sequence comprising an amino acid sequence of the formula X1-$X^2$-$X^3$-$X^4$-$X^5$-$X^6$$X^7$$X^8$-$X^9$-$X^{10}$-$X^{11}$$X^{12}$ (SEQ ID NO:240), wherein $X^1$ is Gln, $X^2$ is Thr, Ser, Ala or Gly, $X^3$ is Ile, $X^4$ is Ser or Leu, $X^5$ is Tyr or absent, $X^6$ is Ser or absent, $X^7$ is Ser or absent, $X^8$ is Asn or absent, $X^9$ is Asn or absent, $X^{10}$ is Lys or absent, $X^{11}$ is Ser, Asn or Thr, and $X^{12}$ is Trp or Tyr; and a LCDR2 sequence comprising an amino acid sequence of the formula $X^1$-$X^2$-$X^3$ (SEQ ID NO:241) wherein $X^1$ is Ala, Trp or Ser, $X^2$ is Ala or Thr, and $X^3$ is Ser.

In a fifth aspect, the invention features a human anti-TL1A antibody or antigen-binding fragment thereof comprising a heavy chain variable region (HCVR) encoded by nucleotide sequence segments derived from $V_H$, $D_H$ and $J_H$ germline sequences, and a light chain variable region (LCVR) encoded by nucleotide sequence segments derived from $V_K$ and $J_K$ germline sequences. In certain embodiments, the antibody or antigen-binding fragment thereof comprises the HCVR and the LCVR encoded by nucleotide sequence segments derived from a germline gene combination selected from the group consisting of: (i) $V_H$3-23, $D_H$2-21, $J_H$4, $V_K$1-5 and $J_K$1; (ii) $V_H$3-7, $D_H$1-7, $J_H$6, $V_K$4-1 and $J_K$3; (iii) $V_H$3-23, $D_H$2-2, $J_H$6, $V_K$1-9 and $J_K$2; (iv) $V_H$3-23, $D_H$6-6, $K_H$4 $V_K$1-9 and $J_K$4; (v) $V_H$1-2, $D_H$2-15, $J_H$3, $V_K$1-12 and $J_K$4; (vi) $V_H$4-34, $D_H$3-9, $J_H$4, $V_K$3-20 and $J_K$4; (vii) $V_H$4-34, $D_H$1-1, $J_H$4, $V_K$3-20 and $J_K$4; and (viii) $V_H$4-34, $D_H$3-3, $J_H$4, $V_K$2-24 and $J_K$4.

In a sixth aspect, the invention features an antibody or antigen-binding fragment thereof that specifically binds to hTL1A or Fhm with an equilibrium dissociation constant ($K_D$) of about 1 nM or less, as measured by surface plasmon resonance assay (for example, BIACORE™). In certain embodiments, the antibody of the invention exhibits a $K_D$ of about 800 pM or less; about 700 pM or less; about 600 pM or less; about 500 pM or less; about 400 pM or less; about 300 pM or less; about 200 pM or less; about 150 pM or less; about 100 pM or less; about 90 pM or less; about 80 pM or less; about 50 pM or less; or 30 pM or less.

In a seventh aspect, the present invention provides an anti-hTL1A antibody or antigen-binding fragment thereof that binds hTL1A protein of SEQ ID NO:244, but does not cross-react with a variant thereof, such as Fhm of SEQ ID NO:246, as determined by, for example, ELISA, surface plasmon resonance assay, or Luminex® xMAP® Technology, as described herein. Fhm contains a single amino acid substitution at position 167, corresponding to Gln in hTL1A, with Arg (see U.S. Pat. No. 6,521,422). In related embodiments, the invention also provides an anti-hTL1A antibody or antigen-binding fragment thereof that binds a hTL1A protein and cross-reacts with an Fhm. In another related embodiment, the invention provides an anti-hTL1A antibody or antigen binding fragment thereof that does not cross-react with mouse TL1A (mTL1A: SEQ ID NO:250, encoded by the nucleotide sequence of SEQ ID NO:249) but does cross-react with TL1A of cynomolgus monkey (Macaca fascicularis, or MfTL1A: SEQ ID NO:248, encoded by the nucleotide sequence of SEQ ID NO:247) or rhesus monkey (Macaca mulatta: the same amino acid sequence as MfTL1A). In further related embodiments, the invention provides an anti-hTL1A antibody or antigen-binding fragment thereof that cross-reacts with both mTL1A and MfTL1A.

The invention encompasses anti-hTL1A antibodies having a modified glycosylation pattern. In some applications, modification to remove undesirable glycosylation sites may be useful, or e.g., removal of a fucose moiety to increase antibody dependent cellular cytotoxicity (ADCC) function (see Shield et a/. (2002) JBC 277:26733). In other applications, removal of N-glycosylation site may reduce undesirable immune reactions against the therapeutic antibodies, or increase affinities of the antibodies. In yet other applications, modification of galactosylation can be made in order to modify complement dependent cytotoxicity (CDC).

In an eighth aspect, the invention features a pharmaceutical composition comprising a recombinant human antibody or fragment thereof which specifically binds hTL1A and a pharmaceutically acceptable carrier. In one embodiment, the invention features a composition which is a combination of an antibody or antigen-binding fragment thereof of the invention, and a second therapeutic agent. The second therapeutic agent may be one or more of any agent such as immunosuppressants, anti-inflammatory agents, analgesic agents, anti-allergy agents, and the like, many of which may have overlapping therapeutic effects of one another. Suitable immunosuppressants to be used in combination with the anti-hTL1A antibodies of the invention include, but are not limited to, glucocorticoids, cyclosporin, methotrexate, interferon β (IFN-β), tacrolimus, sirolimus, azathioprine, mercaptopurine, opioids, mycophenolate, TNF-binding proteins, such as infliximab, eternacept, adalimumab, and the like, cytotoxic antibiotics, such as dactinomycin, anthracyclines, mitomycin C, bleomycin, mithramycin, and the like, antibodies targeting immune cells, such as anti-CD20 antibodies, anti-CD3 antibodies, and the like. Suitable anti-inflammatory agents and/or analgesics for combination therapies with anti-hTL1A antibodies include, corticosteroids, non-steroidal anti-inflammatory drugs (NSAIDs), such as aspirin, ibuprofen, naproxen, Cox-2 inhibitors, and the like, TNF-a antagonists, IL-1 antagonists, IL-6 antagonists, acetaminophen, morphinomimetics, and the like. Suitable anti-allergy agents include antihistamines, glucocorticoids, epinephrine (adrenaline), theophylline, cromolyn sodium and anti-leukotrienes, as well as anti-cholinergics, decongestants, mast cell stabilizers, and the like.

In a ninth aspect, the invention features methods for inhibiting hTL1A activity using the anti-hTL1A antibody or antigen-binding portion of the antibody of the invention, wherein the therapeutic methods comprise administering a therapeutically effective amount of a pharmaceutical composition comprising an antibody or antigen-binding fragment of an antibody of the invention and, optionally, one or more additional therapeutic agents described above. The disease or disorder treated is any disease or condition which is improved, ameliorated, inhibited or prevented, or its occurrence rate reduced compared to that without anti-hTL1A antibody treatment, by removal, inhibition or reduction of TL1A activity. Examples of diseases or disorders treatable by the methods of the invention include, but are not limited to, inflammatory diseases and/or autoimmune diseases, such as inflammatory bowel diseases (IBD) including UC and CD, RA, MS, type 1 and type 2 diabetes, psoriasis, psoriatic arthritis, ankylosing spondylitis, atopic dermatitis, and the like; allergic reactions or conditions, including asthma, allergic lung inflammation, and the like; cancers atherosclerosis, infections, neurodegenerative diseases, graft rejection, graft vs. host diseases (GVHD), cardiovascular disorders/diseases, and the like.

Other embodiments will become apparent from a review of the ensuing detailed description.

DETAILED DESCRIPTION

Before the present invention is described in detail, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, preferred methods and materials are now described. All publications mentioned herein are incorporated herein by reference in their entirety.

Definitions

The term "human TNF-like ligand 1A" or "hTL1A", as used herein, refers to hTL1A having the nucleic acid sequence shown in SEQ ID NO:243 and the amino acid sequence of SEQ ID NO:244, or a biologically active fragment thereof, as well as hTL1A variants, including Fhm having the nucleic acid sequence shown in SEQ ID NO:245 and the amino acid sequence of SEQ ID NO:246, or a biologically active fragment thereof, unless specifically indicated otherwise.

The term "antibody", as used herein, is intended to refer to immunoglobulin molecules comprised of four polypeptide chains, two heavy (H) chains and two light (L) chains interconnected by disulfide bonds. Each heavy chain is comprised of a heavy chain variable region (HCVR) and a heavy chain constant region ($C_H$; comprised of domains $C_H1$, $C_H2$ and $C_H3$). Each light chain is comprised of a light chain variable region (LCVR) and a light chain constant region ($C_L$). The HCVR and LCVR can be further subdivided into regions of hypervariability, termed complementarity determining regions (CDR), interspersed with regions that are more conserved, termed framework regions (FR). Each HCVR and LCVR is composed of three CDRs and four FRs, arranged from amino-terminus to carboxy-terminus in the following order: FR1, CDR1, FR2, CDR2, FR3, CDR3, and FR4.

Substitution of one or more CDR residues or omission of one or more CDRs is also possible. Antibodies have been described in the scientific literature in which one or two CDRs can be dispensed with for binding. Padlan et al. (1995 FASEB J. 9:133-139) analyzed the contact regions between antibodies and their antigens, based on published crystal structures, and concluded that only about one fifth to one third of CDR residues actually contact the antigen. Padlan also found many antibodies in which one or two CDRs had no amino acids in contact with an antigen (see also, Vajdos et al. 2002 *J Mol Biol* 320:415-428).

CDR residues not contacting antigen can be identified based on previous studies (for example, residues H60-H65 in CDRH2 are often not required), from regions of Kabat CDRs lying outside Chothia CDRs, by molecular modeling and/or empirically. If a CDR or residue(s) thereof is omitted, it is usually substituted with an amino acid occupying the corresponding position in another human antibody sequence or a consensus of such sequences. Positions for substitution within CDRs and amino acids to substitute can also be selected empirically. Empirical substitutions can be conservative or non-conservative substitutions.

The term "human antibody", as used herein, is intended to include antibodies having variable and constant regions derived from human germline immunoglobulin sequences. The human mAbs of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include mAbs in which CDR sequences derived from the germline of another mammalian species (e.g., mouse), have been grafted onto human FR sequences.

The fully-human anti-TL1A antibodies disclosed herein may comprise one or more amino acid substitutions, insertions and/or deletions in the framework and/or CDR regions of the heavy and light chain variable domains as compared to the corresponding germline sequences. Such mutations can be readily ascertained by comparing the amino acid sequences disclosed herein to germline sequences available from, for example, public antibody sequence databases. The present invention includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residues(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline back-mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present invention may contain any combination of two or more germline mutations within the framework and/or CDR regions, e.g., wherein certain individual residues are mutated to the corresponding residues of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present invention.

The present invention also includes anti-TL1A antibodies comprising variants of any of the HCVR, LCVR, and/or CDR amino acid sequences disclosed herein having one or more conservative substitutions. For example, the present invention includes anti-TL1A antibodies having HCVR, LCVR, and/or CDR amino acid sequences with, e.g., 10 or fewer, 8 or fewer, 6 or fewer, 4 or fewer, 2 or 1, conservative amino acid substitution(s) relative to any of the HCVR, LCVR, and/or CDR amino acid sequences disclosed herein.

Unless specifically indicated otherwise, the term "antibody" (Ab), as used herein, shall be understood to encompass antibody molecules comprising two immunoglobulin heavy chains and two immunoglobulin light chains (i.e., "full antibody molecules") as well as antigen-binding fragments thereof. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and (optionally) constant domains. Such DNA is known and/or is readily available from, e.g., commercial sources, DNA libraries (including, e.g., phage-display antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H1$; (ii) $V_H$-$C_H2$; $V_H$-$C_H3$; (iv) $V_H$-$C_H1$-$C_H2$; (v) $V_H$-$C_H1$-$C_H2$-$C_H3$; (VI) $V_H$-$C_H2$-$C_H3$; (Vii) $V_H$-$C_L$; (Viii) $V_L$-$C_H1$; (ix) $V_L$-$C_H2$; (X) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be monospecific or multispecific (e.g., bispecific).

A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen-binding fragment of an antibody of the present invention using routine techniques available in the art.

In certain embodiments, antibody or antibody fragments of the invention may be conjugated to a therapeutic moiety ("immunoconjugate"), such as a cytotoxin, a chemotherapeutic drug, an immunosuppressant or a radioisotope.

The term "specifically binds," or the like, means that an antibody or antigen-binding fragment thereof forms a complex with an antigen that is relatively stable under physiological conditions. Specific binding can be characterized by an equilibrium dissociation constant ($K_D$) of about 3000 nM or less (i.e., a smaller $K_D$ denotes a tighter binding), about 2000 nM or less, about 1000 nM or less; about 500 nM or less; about 300 nM or less; about 200 nM or less; about 100 nM or less; about 50 nM or less; about 1 nM or less; or about 0.5 nM or less. Methods for determining whether two molecules specifically bind are well known in the art and include, for example, equilibrium dialysis, surface plasmon resonance, and the like. An isolated antibody that specifically binds hTL1A may, however, exhibit cross-reactivity to other antigens, such as TL1A molecules from other species, for example, cynomolgus monkey TL1A (SEQ ID NO:248), and/or mouse TL1A (SEQ ID NO:250), and/or a TL1A variant, such as Fhm (SEQ ID NO:246). Moreover, multi-specific antibodies (e.g., bispecifics) that bind to hTL1A and one or more additional antigens are nonetheless considered antibodies that "specifically bind' hTL1A, as used herein.

The term "high affinity" antibody refers to those antibodies having a binding affinity to hTL1A, expressed as $K_D$, of about $1\times10^{-9}$ M or less, about $0.5\times10^{-9}$ M or less, about $0.25\times10^{-9}$ M or less, about $1\times10^{10}$ M or less, or about $0.5\times10^{-10}$ M or less, as measured by surface plasmon resonance, e.g., BIACORE™ or solution-affinity ELISA.

The term "$K_D$", as used herein, is intended to refer to the equilibrium dissociation constant of a particular antibody-antigen interaction.

By the term "slow off rate", "Koff" or "$k_d$" is meant an antibody that dissociates from hTL1A with a rate constant of $1\times10^{-3}$ s$^{-1}$ or less, preferably $1\times10^{-4}$ s$^{-1}$ or less, as determined by surface plasmon resonance, e.g., BIACORE™.

By the term "intrinsic affinity constant" or "$k_a$" is meant an antibody that associates with hTL1A at a rate constant of about $1\times10^{3}$ M$^{-1}$s$^{-1}$ or higher, as determined by surface plasmon resonance, e.g., BIACORE™.

An "isolated antibody", as used herein, is intended to refer to an antibody that is substantially free of other mAbs having different antigenic specificities (e.g., an isolated antibody that specifically binds hTL1A is substantially free of Abs that specifically bind antigens other than hTL1A). An isolated antibody that specifically binds hTL1A may, however, have cross-reactivity to other antigens, such as TL1A molecules from other species, such as cynomolgus monkey and mouse, and/or hTL1A variants, such as Fhm.

A "neutralizing antibody", as used herein (or an "antibody that neutralizes TL1A activity"), is intended to refer to an antibody whose binding to TL1A results in inhibition of at least one biological activity of TL1A. This inhibition of the biological activity of TL1A can be assessed by measuring one or more indicators of TL1A biological activity by one or more of several standard in vitro or in vivo assays known in the art (also see examples below).

The term "surface plasmon resonance", as used herein, refers to an optical phenomenon that allows for the analysis of real-time biospecific interactions by detection of alterations in protein concentrations within a biosensor matrix, for example using the BIACORE™ system (Pharmacia Biosensor AB, Uppsala, Sweden and Piscataway, N.J.).

The term "epitope" is a region of an antigen that is bound by an antibody. Epitopes may be defined as structural or functional. Functional epitopes are generally a subset of the structural epitopes and have those residues that directly contribute to the affinity of the interaction. Epitopes may also be conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 90%, and more preferably at least about 95%, 96%, 97%, 98% or 99% of the nucleotide bases, as measured by any well-known algorithm of sequence identity, such as FASTA, BLAST or GAP, as discussed below.

As applied to polypeptides, the term "substantial similarity" or "substantially similar" means that two peptide sequences, when optimally aligned, such as by the programs GAP or BESTFIT using default gap weights, share at least 90% sequence identity, even more preferably at least 95%, 98% or 99% sequence identity. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent or degree of similarity may be adjusted upwards to correct for the conservative nature of the substitution. Means for making this adjustment are well known to those of skill in the art. See, e.g., Pearson (1994) *Methods Mol. Biol.* 24: 307-331, which is herein incorporated by reference. Examples of groups of amino acids that have side chains with similar chemical properties include 1) aliphatic side chains: glycine, alanine, valine, leucine and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartate and glutamate, and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) *Science* 256: 1443 45, herein incorporated by reference. A "moderately conservative" replacement is any change having a nonnegative value in the PAM250 log-likelihood matrix.

Sequence similarity for polypeptides is typically measured using sequence analysis software. Protein analysis software matches similar sequences using measures of similarity assigned to various substitutions, deletions and other modifications, including conservative amino acid substitutions. For instance, GCG software contains programs such as GAP and BESTFIT which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA with default or recommended parameters; a program in GCG Version 6.1. FASTA (e.g., FASTA2 and FASTA3) provides alignments and percent sequence identity of the regions of the best overlap between the query and search sequences (Pearson, 2000, supra). Another preferred algorithm when comparing a sequence of the invention to a database containing a large number of sequences from different organisms is the computer program BLAST, especially BLASTP or TBLASTN, using default parameters. See, e.g., Altschul et al., 1990, *J. Mol. Biol.* 215: 403 410 and, 1997, *Nucleic Acids Res.* 25:3389 402, each of which is herein incorporated by reference.

By the phrase "therapeutically effective amount" is meant an amount that produces the desired effect for which it is administered. The exact amount will depend on the purpose of the treatment, the age and the size of a subject treated, the route of administration, and the like, and will be ascertainable by one skilled in the art using known techniques (see, for example, Lloyd (1999) The Art, Science and Technology of Pharmaceutical Compounding).

Preparation of Human Antibodies

Methods for generating human antibodies in transgenic mice are known in the art. Any such known methods can be used in the context of the present invention to make human antibodies that specifically bind to TL1A.

Using VELOCIMMUNE™ technology or any other known method for generating monoclonal antibodies, high affinity chimeric antibodies to TL1A are initially isolated having a human variable region and a mouse constant region. As in the experimental section below, the antibodies are characterized and selected for desirable characteristics, including affinity, selectivity, epitope, and the like.

In general, the antibodies of the instant invention possess very high affinities, typically possessing $K_D$ of from about $10^{-12}$ M through about $10^{-9}$ M, when measured by binding to antigen either immobilized on solid phase or in solution phase. The mouse constant regions are replaced with desired human constant regions, for example, wild-type IgG1 (SEQ ID NO:255) or IgG4 (SEQ ID NO:256), or modified IgG1 or IgG4 (for example, IgG4 with Ser-108 substituted with Pro as shown in SEQ ID NO:257), to generate the fully human antibodies of the invention. While the constant region selected may vary according to specific use, high affinity antigen-binding and target specificity characteristics of the antibodies reside in the variable region.

Epitope Mapping and Related Technologies

To screen for antibodies that bind to a particular epitope, a routine cross-blocking assay such as that described in Antibodies, Harlow and Lane (Cold Spring Harbor Press, Cold Spring Harb., N.Y.) can be performed. Other methods include alanine scanning mutants, peptide blots (Reineke, 2004, *Methods Mol Biol* 248:443-63) (herein specifically incorporated by reference in its entirety), or peptide cleavage analysis. In addition, methods such as epitope excision, epitope extraction and chemical modification of antigens can be employed (Tomer, 2000, *Protein Science* 9: 487-496) (herein specifically incorporated by reference in its entirety).

The term "epitope" refers to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5 or 8-10 amino acids in a unique spatial conformation.

Modification-Assisted Profiling (MAP), also known as Antigen Structure-based Antibody Profiling (ASAP) is a method that categorizes large numbers of mAbs directed against the same antigen according to the similarities of the binding profile of each antibody to chemically or enzymatically modified antigen surfaces (US 2004/0101920, herein specifically incorporated by reference in its entirety). Each category may reflect a unique epitope either distinctly different from or partially overlapping with epitope represented by another category. This technology allows rapid filtering of genetically identical mAbs, such that characterization can be focused on genetically distinct mAbs. When applied to hybridoma screening, MAP may facilitate identification of rare hybridoma clones that produce mAbs having the desired characteristics. MAP may be used to sort the anti-TL1A mAbs of the invention into groups of mAbs binding different epitopes.

The present invention includes hTL1A antibodies that bind to the same epitope as any of the specific exemplary antibodies described herein. Likewise, the present invention also includes anti-hTL1A antibodies that compete for binding to hTL1A or a hTL1A fragment with any of the specific exemplary antibodies described herein.

One can easily determine whether an antibody binds to the same epitope as, or competes for binding with, a reference anti-hTL1A antibody by using routine methods known in the art. For example, to determine if a test antibody binds to the same epitope as a reference anti-hTL1A antibody of the invention, the reference antibody is allowed to bind to a hTL1A protein or peptide under saturating conditions. Next, the ability of a test antibody to bind to the hTL1A molecule is assessed. If the test antibody is able to bind to hTL1A following saturation binding with the reference anti-hTL1A antibody, it can be concluded that the test antibody binds to a different epitope than the reference anti-hTL1A antibody. On the other hand, if the test antibody is not able to bind to the hTL1A molecule following saturation binding with the reference anti-hTL1A antibody, then the test antibody may bind to the same epitope as the epitope bound by the reference anti-hTL1A antibody of the invention.

To determine if an antibody competes for binding with a reference anti-hTL1A antibody, the above-described binding methodology is performed in two orientations: In a first orientation, the reference antibody is allowed to bind to a hTL1A molecule under saturating conditions followed by assessment of binding of the test antibody to the hTL1A molecule. In a second orientation, the test antibody is allowed to bind to a hTL1A molecule under saturating conditions followed by assessment of binding of the reference antibody to the TL1A molecule. If, in both orientations, only the first (saturating) antibody is capable of binding to the TL1A molecule, then it is concluded that the test antibody and the reference antibody compete for binding to hTL1A. As will be appreciated by a person of ordinary skill in the art, an antibody that competes for binding with a reference antibody may not necessarily bind to the identical epitope as the reference antibody, but may sterically block binding of the reference antibody by binding an overlapping or adjacent epitope.

Two antibodies bind to the same or overlapping epitope if each competitively inhibits (blocks) binding of the other to the antigen. That is, a 1-, 5-, 10-, 20- or 100-fold excess of one antibody inhibits binding of the other by at least 50% but preferably 75%, 90% or even 99% as measured in a competitive binding assay (see, e.g., Junghans et al., *Cancer Res.* 1990:50:1495-1502). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, surface plasmon resonance, flow cytometry or any other quantitative or qualitative antibody-binding assay available in the art.

Immunoconjugates

The invention encompasses a human anti-TL1A monoclonal antibody conjugated to a therapeutic moiety ("immunoconjugate"), such as a cytotoxin, a chemotherapeutic drug, an immunosuppressant or a radioisotope. Cytotoxin agents include any agent that is detrimental to cells. Examples of suitable cytotoxin agents and chemotherapeutic agents for forming immunoconjugates are known in the art, see for example, WO 05/103081, herein specifically incorporated by reference).

Bispecifics

The antibodies of the present invention may be monospecific, bispecific, or multispecific. Multispecific mAbs may be specific for different epitopes of one target polypeptide or may contain antigen-binding domains specific for more than one target polypeptide. See, e.g., Tutt et al., 1991, *J. Immunol.* 147:60-69. The human anti-hTL1A mAbs can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment, to produce a bispecific or a multispecific antibody with a second binding specificity.

An exemplary bi-specific antibody format that can be used in the context of the present invention involves the use of a first immunoglobulin (Ig) $C_H3$ domain and a second Ig $C_H3$ domain, wherein the first and second Ig $C_H3$ domains differ from one another by at least one amino acid, and wherein at least one amino acid difference reduces binding of the bispecific antibody to Protein A as compared to a bi-specific antibody lacking the amino acid difference. In one embodiment, the first Ig $C_H3$ domain binds Protein A and the second Ig $C_H3$ domain contains a mutation that reduces or abolishes Protein A binding such as an H95R modification (by IMGT exon numbering; H435R by EU numbering). The second $C_H3$ may further comprise a Y96F modification (by IMGT; Y436F by EU). Further modifications that may be found within the second $C_H3$ include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies. Variations on the bi-specific antibody format described above are contemplated within the scope of the present invention.

Bioequivalents

The anti-hTL1A antibodies and antibody fragments of the present invention encompass proteins having amino acid sequences that vary from those of the described mAbs, but that retain the ability to bind human TL1A. Such variant mAbs and antibody fragments comprise one or more additions, deletions, or substitutions of amino acids when compared to parent sequence, but exhibit biological activity that is essentially equivalent to that of the described mAbs. Likewise, the hTL1A mAb-encoding DNA sequences of the present invention encompass sequences that comprise one or more additions, deletions, or substitutions of nucleotides when compared to the disclosed sequence, but that encode an anti-hTL1A antibody or antibody fragment that is essentially bioequivalent to an anti-hTL1A antibody or antibody fragment of the invention. Examples of such variant amino acid and DNA sequences are discussed above.

Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single does or multiple dose. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied. In one embodiment, two antigen-binding proteins are bioequivalent if there are no clinically meaningful differences in their safety, purity, and potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of anti-hTL1A antibodies of the invention may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation.

Therapeutic Administration and Formulations

The invention provides therapeutic compositions comprising the anti-hTL1A antibodies or antigen-binding fragments thereof of the present invention and the therapeutic methods using the same. The administration of therapeutic compositions in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA, 1998, *J Pharm Sci Technol* 52:238-311.

The dose may vary depending upon the age and the size of a subject to be administered, target disease, the purpose of the treatment, conditions, route of administration, and the like. When the antibody of the present invention is used for treating various conditions and diseases directly or indirectly associated with TL1A, including inflammatory diseases/disorders, autoimmune diseases/disorders, allergic reactions, and the like, in an adult patient, it is advantageous to intravenously or subcutaneously administer the antibody of the present invention at a single dose of about 0.01 to about 20 mg/kg body weight, more preferably about 0.02 to about 7, about 0.03 to about 5, or about 0.05 to about 3 mg/kg body weight. Depending on the severity of the condition, the frequency and the duration of the treatment can be adjusted. In certain embodiments, the antibody or antigen-binding fragment thereof of the invention can be administered as an initial dose of at least about 0.1 mg to about 800 mg, about 1 to about 500 mg, about 5 to about 300 mg, or about 10 to about 200 mg, to about 100 mg, or to about 50 mg. In certain embodiments, the initial dose may be followed by administration of a second or a plurality of subsequent doses of the antibody or antigen-binding fragment thereof in an amount that can be approximately the same or less than that of the initial dose, wherein the subsequent doses are separated by at least 1 day to 3 days; at least one week, at least 2 weeks; at least 3 weeks; at least 4 weeks; at least 5 weeks; at least 6 weeks; at least 7 weeks; at least 8 weeks; at least 9 weeks; at least 10 weeks; at least 12 weeks; or at least 14 weeks.

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al., 1987, *J. Biol. Chem.* 262:4429-4432). Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

The pharmaceutical composition can be also delivered in a vesicle, in particular a liposome (see Langer, 1990, *Science* 249:1527-1533; Treat et al., 1989, in Liposomes in the Therapy of Infectious Disease and Cancer, Lopez Berestein and Fidler (eds.), Liss, New York, pp. 353-365; Lopez-Berestein, ibid., pp. 317-327; see generally ibid.).

In certain situations, the pharmaceutical composition can be delivered in a controlled release system. In one embodiment, a pump may be used (see Langer, supra; Sefton, 1987, *CRC Crit. Ref. Biomed. Eng.* 14:201). In another embodiment, polymeric materials can be used; see, Medical Applications of Controlled Release, Langer and Wise (eds.), CRC Pres., Boca Raton, Fla. (1974). In yet another embodiment, a controlled release system can be placed in proximity of the composition's target, thus requiring only a fraction of the systemic dose (see, e.g., Goodson, in Medical Applications of Controlled Release, supra, vol. 2, pp. 115-138, 1984).

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule. A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but certainly are not limited to AUTOPEN™ (Owen Mumford, Inc., Woodstock, UK), DISETRONIC™ pen (Disetronic Medical Systems, Burghdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (sanofi-aventis, Frankfurt, Germany), to name only a few. Examples of disposable pen delivery devices having applications in subcutaneous delivery of a pharmaceutical composition of the present invention include, but certainly are not limited to the SOLOSTAR™ pen (sanofi-aventis), the FLEXPEN™ (Novo Nordisk), and the KWIKPEN™ (Eli Lilly).

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 0.1 to about 800 mg per dosage form in a unit dose; especially in the form of injection, the aforesaid antibody is contained in about 1 to about 500 mg, in about 5 to 300 mg, in about 8 to 200 mg, and in about 10 to about 100 mg for the other dosage forms.

Combination Therapies

The invention further provides therapeutic methods for treating diseases or disorders, which is directly or indirectly associated with hTL1A, by administering the hTL1A mAb or fragment thereof of the invention in combination with one or more additional therapeutic agents. The additional therapeutic agent may be one or more of any agent that is advantageously combined with the antibody or fragment thereof of the invention, including immunosuppressants, anti-inflammatory agents, analgesic agents, anti-allergy agents, and the like. Suitable immunosuppressants include, but are not limited to, glucocorticoids, cyclosporin, methotrexate, interferon β (IFN-β), tacrolimus, sirolimus, azathioprine, mercaptopurine, opioids, mycophenolate, TNF-binding proteins, such as infliximab, eternacept, adalimumab, and the like, cytotoxic antibiotics, such as dactinomycin, anthracyclines, mitomycin C, bleomycin, mithramycin, and the like, antibodies targeting immune cells, such as anti-CD20 antibodies, anti-CD3 antibodies, and the like. Suitable anti-inflammatory agents and/or analgesics for combination therapies with the anti-hTL1A antibodies include, corticosteroids, non-steroidal anti-inflammatory drugs (NSAIDs), such as aspirin, ibuprofen, naproxen, Cox-2 inhibitors, and the like, TNF-a antagonists (e.g., Infliximab or REMICADE® by Centocor Inc.; golimumab by Centocor Inc.; etanercept or ENBREL® by AmgenANyeth; adalimumab or HUMIRA® by Abbott Laboratories, and the like), IL-1 antagonists (e.g., IL-1-binding fusion proteins, for example, ARCALYST® by Regeneron Pharmaceuticals, Inc., see U.S. Pat. No. 6,927,044; KINERET® by Amgen, and the like), IL-6 antagonists (e.g., anti-IL-6 receptor antibodies as disclosed in U.S. Pat. No. 7,582,298, and ACTEMRA® by Roche), acetaminophen, morphinomimetics, and the like. Suitable anti-allergy agents, which can block the action of allergic mediators, or to prevent activation of cells and degranulation processes, include antihistamines, glucocorticoids, epinephrine (adrenaline), theophylline, cromolyn sodium and anti-leukotrienes, such as montelukast (SINGULAIR® by Merck) or zafirlukast (ACCOLATE® by AstraZeneca), as well as anti-cholinergics, decongestants, mast cell stabilizers, and other compounds that can impair eosinophil chemotaxis.

The hTL1A mAb or fragment thereof of the invention and the additional therapeutic agent(s) can be co-administered together or separately. Where separate dosage formulations are used, the antibody or fragment thereof of the invention and the additional agents can be administered concurrently, or separately at staggered times, i.e., sequentially, in appropriate orders.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used but some experimental errors and deviations should be accounted for. Unless indicated otherwise, molecular weight is average molecular weight, temperature is in degrees Centigrade, and pressure is at or near atmospheric.

Example 1

Generation of Human Antibodies to Human TL1A

VELOCIMMUNE™ mice were immunized with human TL1A, and the antibody immune response monitored by antigen-specific immunoassay using serum obtained from these mice. Anti-hTL1A antibody-expressing B cells were harvested from the spleens of immunized mice shown to have elevated anti-hTL1A antibody titers and were fused with mouse myeloma cells to form hybridomas. The hybridomas were screened and selected to identify cell lines expressing hTL1A-specific antibodies using assays as described below. The assays identified several cell lines that produced chimeric anti-hTL1A antibodies designated as H2M1681N, H2M1704N, H2M1804N, H2M1805N, H2M1817N and H2M1818N. These antibodies were later converted to hIgG4 isotype by replacing the respective mouse constant regions with the hIgG4 amino acid sequence of SEQ ID NO:257, which contains a S108P mutation in the hinge region, and designated as H4H1681N, H4H1704N, H4H1804N, H4H1805N, H4H1817N and H4H1818N, respectively.

Human TL1A-specific antibodies were also isolated directly from antigen-immunized B cells without fusion to myeloma cells, as described in U.S. Pat. No. 7,582,298, which is hereby incorporated by reference in its entirety. Heavy and light chain variable regions were cloned to generate fully human anti-hTL1A antibodies designated as H4H1719P, H4H1725P, H4H1738P, H4H1742P, H4H1745P, H4H1750P and H4H1752P. Stable recombinant antibody-expressing CHO cell lines were established.

Example 2

Variable Gene Utilization Analysis

To analyze the structure of antibodies produced, the nucleic acids encoding antibody variable regions were cloned and sequenced. From the nucleic acid sequence and predicted amino acid sequence of the antibodies, gene usage was identified for each Heavy Chain Variable Region (HCVR) and Light Chain Variable Region (LCVR). Table 1 shows the gene usage for selected antibodies in accordance with the invention.

TABLE 1

| Antibody | HCVR | | | LCVR | |
|---|---|---|---|---|---|
| | $V_H$ | $D_H$ | $J_H$ | $V_K$ | $J_K$ |
| H2M1704 | 3-7 | 1-7 | 6 | 4-1 | 3 |
| H2M1681 | 3-23 | 2-21 | 4 | 1-5 | 1 |
| H2M1817 | 4-34 | 3-9 | 4 | 3-20 | 4 |
| H2M1804 | 4-34 | 1-1 | 4 | 3-20 | 4 |
| H2M1818 | 3-11 | 4-17 | 6 | 4-1 | 1 |
| H2M1805 | 4-34 | 3-3 | 4 | 2-24 | 4 |
| H4H1719 | 3-9 | 3-3 | 6 | 2-28 | 2 |
| H4H1725 | 1-2 | 2-15 | 3 | 1-12 | 4 |
| H4H1738 | 3-15 | 4-4 | 6 | 2-28 | 2 |
| H4H1742 | 3-23 | 2-2 | 6 | 1-9 | 2 |
| H4H1745 | 3-23 | 6-6 | 4 | 1-9 | 4 |
| H4H1750 | 3-30 | 4-17 | 6 | 1-17 | 1 |
| H4H1752 | 3-23 | 1-7 | 4 | 1-5 | 1 |

Table 2 shows the heavy and light chain variable region amino acid sequence pairs of selected anti-hTL1A antibodies and their corresponding antibody identifiers. The N and P designations refer to antibodies having heavy and light chains with identical CDR sequences but with sequence variations in regions that fall outside of the CDR sequences (i.e., in the framework regions). Thus, N and P variants of a particular antibody have identical CDR sequences within their heavy and light chain variable regions but contain modifications within the framework regions.

TABLE 2

| mAb Name (H2M- or H4H-) | HCVR/LCVR SEQ ID NOS |
|---|---|
| 1704N | 2/10 |
| 1681N | 18/26 |
| 1804N | 34/42 |
| 1805N | 50/58 |
| 1817N | 66/74 |
| 1818N | 82/90 |
| 1719N | 98/106 |
| 1719P | 114/116 |
| 1725N | 118/126 |
| 1725P | 134/136 |
| 1738N | 138/146 |
| 1738P | 154/156 |
| 1745N | 158/166 |
| 1745P | 174/176 |
| 1750N | 178/186 |
| 1750P | 194/196 |
| 1752N | 198/206 |
| 1752P | 214/216 |
| 1742N | 218/226 |
| 1742P | 234/236 |

Example 3

TL1A Binding Affinity Determination.

Binding affinities and kinetic constants were determined by surface plasmon resonance at 25° C. and 37° C. as indicated in Tables 3-5 for human monoclonal anti-TL1A antibodies binding to the following TL1A species variants: human (h) (CHO-expressed, residues 72-251 of SEQ ID NO:244, with N-terminal His$_6$-tag), cynomolgus monkey (Mf) (E. coil-expressed, residues 72-251 of SEQ ID NO:248, with or without N-terminal Met), cynomolgus monkey (CHO-expressed, residues 72-251 of SEQ ID NO:248, with N-terminal His$_6$-tag), mouse (m) (E. coli-expressed, residues 76-252 of SEQ ID NO:250, with or without N-terminal Met), mouse (CHO-expressed, residues 76-252 of SEQ ID NO:250, with N-terminal His$_6$-tag), and rat (CHO cell-expressed; residues 76-252 of SEQ ID NO:258, with N-terminal His$_6$-tag). Binding constants were also determined for the hTL1A variant, Fhm (E. coli-expressed, residues 72-251 of SEQ ID NO:246 containing Q167R substitution, with or without N-terminal Met). Measurements were conducted on a T100 BIACORE™ instrument. Antibodies, expressed with either mouse Fc (designated with prefix "H2M") or human IgG4 (S108P) Fc (designated with prefix "H4H"), were captured onto an anti-Fc sensor surface, and at least three different concentrations of the soluble TL1A proteins ranging from 1.25 nM to 100 nM were injected over the sensor surface. Kinetic association ($k_a$) and dissociation ($k_d$) rate constants were determined by fitting the data to a 1:1 binding model using BIAevaluation 4.1 curve fitting software (BIAcore Life Sciences). Molar concentrations of TL1A/Fhm used in the data fitting assumed a monomeric state for TL1A in solution. Binding dissociation equilibrium constants ($K_D$) and dissociative half-lives ($t_{1/2}$) were calculated from the kinetic rate constants as: $K_D(M)=k_d/k_a$; and $t_{1/2}$ (min) $=[\ln2/(60*k_d)]$. NB: No binding under the conditions tested; NT: Not tested in this experiment; *: Fitted $k_d$ values below $1\times10^{-6}$ (1/s) are slower than the detection limit under these experimental conditions; therefore, $k_d$ values were set at $1\times10^{-6}$ (1/s) for the purpose of approximating $K_D$ and $t_{1/2}$: **: Equilibrium dissociation constants for antibodies were determined under steady state conditions.

As shown in Tables 3 and 4, antibodies bound with high affinity to CHO-expressed forms of both human and monkey TL1A proteins at 25° C. (13 and 12 antibodies with $K_D$ <1 nM, respectively) and at 37° C. (13 and 12 antibodies with $K_D$<1 nM, respectively). H4H1750P bound significantly weaker to the monkey compared to the human TL1A protein. H4H1704N bound to CHO-expressed mTL1A with $K_D$<2nM at both 25° C. and 37° C. H4H1818N bound CHO-expressed mTL1A at 25° C. ($K_D$<7 nM) but not at 37° C. Five antibodies, H4H1681N, H4H1738P, H4H1750P, H4H1752P and H4H1805N, did not bind to CHO-expressed rat TL1A at either 25° C. or 37° C.; the other eight antibodies bound to rat TL1A at both temperatures with $K_D$ ranging from ~0.6 pM to ~16 nM.

As shown in Table 5, three antibodies (H2M1681N, H4H1752P and H2M1805N) did not demonstrate binding to the E. coli-expressed Fhm variant [hTL1A(Q167R)] under the conditions tested. Three antibodies (H2M1704N, H4H1725P, and H2M1818N) demonstrated weak binding ($K_D$ ranging from ~60 nM to ~170 nM) to mouse TL1A expressed in E. coli as assessed under steady-state conditions, while all other tested antibodies did not bind to the mouse TL1A protein under the tested conditions.

TABLE 3

CHO-expressed TL1A at 25° C.

| mAb | hTL1A $K_D$ (pM) | hTL1A $t_{1/2}$ (min) | MfTL1A $K_D$ (pM) | MfTL1A $t_{1/2}$ (min) | mTL1A $K_D$ (pM) | mTL1A $t_{1/2}$ (min) | rTL1A $K_D$ (pM) | rTL1A $t_{1/2}$ (min) |
|---|---|---|---|---|---|---|---|---|
| H4H1681N | 263 | 36 | 404 | 25 | NB | NB | NB | NB |
| H4H1704N | 39.2 | 453 | 59.9 | 276 | 194 | 46 | 404 | 25 |
| H4H1719P | 481 | 44 | 417 | 45 | NB | NB | 364 | 38 |
| H4H1725P | 63.6 | 185 | 346 | 64 | NB | NB | 317 | 26 |
| H4H1738P | 608 | 64 | 361 | 93 | NB | NB | NB | NB |
| H4H1742P | 60.4 | 755 | 115 | 577 | NB | NB | 78 | 144 |
| H4H1745P | 164 | 172 | 115 | 231 | NB | NB | 2.7 (nM) | 4 |
| H4H1750P | 15.8* | 11550* | 8.6 (nM) | 21 | NB | NB | NB | NB |
| H4H1752P | 156 | 197 | 213 | 139 | NB | NB | NB | NB |
| H4H1804N | 291 | 51 | 264 | 49 | NB | NB | 321 | 43 |
| H4H1805N | 365 | 73 | 342 | 74 | NB | NB | NB | NB |
| H4H1817N | 321 | 103 | 356 | 92 | NB | NB | 2.5 (nM) | 25 |
| H4H1818N | 124 | 120 | 119 | 122 | 7.1 (nM) | 12 | 88 | 92 |

TABLE 4

CHO-expressed TL1A at 37° C.

| mAb | hTL1A $K_D$ (pM) | hTL1A $t_{1/2}$ (min) | MfTL1A $K_D$ (pM) | MfTL1A $t_{1/2}$ (min) | mTL1A $K_D$ (pM) | mTL1A $t_{1/2}$ (min) | rTL1A $K_D$ (pM) | rTL1A $t_{1/2}$ (min) |
|---|---|---|---|---|---|---|---|---|
| H4H1681N | 254 | 31 | 226 | 32 | NB | NB | NB | NB |
| H4H1704N | 1.00* | 11550* | 0.93* | 11550* | 1.3 (nM) | 27 | 46 | 133 |
| H4H1719P | 7.61 | 1912 | 2.01 | 5784 | NB | NB | 78 | 86 |
| H4H1725P | 23.9 | 758 | 17.7 | 888 | NB | NB | 411 | 15 |
| H4H1738P | 571 | 51 | 465 | 60 | NB | NB | NB | NB |
| H4H1742P | 4.37* | 11550* | 4.45* | 11550* | NB | NB | 653 | 27 |
| H4H1745P | 177 | 129 | 173 | 124 | NB | NB | 16.5 (nM) | 11 |
| H4H1750P | 13.8* | 11550* | 17.1 (nM) | 11 | NB | NB | NB | NB |
| H4H1752P | 225 | 96 | 223 | 91 | NB | NB | NB | NB |
| H4H1804N | 45.8 | 286 | 78 | 167 | NB | NB | 127 | 88 |
| H4H1805N | 299 | 80 | 352 | 68 | NB | NB | NB | NB |
| H4H1817N | 27.8 | 1098 | 25.6 | 1150 | NB | NB | 1.6 (nM) | 26 |
| H4H1818N | 0.925* | 11550* | 0.804* | 11550* | NB | NB | 0.61* | 11550* |

TABLE 5

E. coli-expressed Fhm/TL1A

| mAb | 25° C. Fhm $K_D$ (pM) | 25° C. Fhm $t_{1/2}$ (min) | 37° C. Fhm $K_D$ (pM) | 37° C. Fhm $t_{1/2}$ (min) | 25° C. MfTL1A $K_D$ (pM) | 25° C. MfTL1A $t_{1/2}$ (min) | 37° C. MfTL1A $K_D$ (pM) | 37° C. MfTL1A $t_{1/2}$ (min) | 25° C. mTL1A $K_D$ (pM)** |
|---|---|---|---|---|---|---|---|---|---|
| H2M1681N | NB | NB | NT | NT | 546 | 54 | 1.5 (nM) | 14 | NB |
| H2M1704N | 282 | 52 | NT | NT | 285 | 57 | 751 | 16 | 127 (nM) |
| H2M1719P | 109 | 96 | 174 | 42 | 242 | 79 | 289 | 40 | NB |
| H4H1725P | 28.9 | 447 | 43.6 | 194 | 63.7 | 292 | 62.2 | 174 | 62 (nM) |
| H4H1738P | 1020 | 19 | 3100 | 4 | 1360 | 18 | 4.2 (nM) | 4 | NB |
| H4H1742P | 437 | 129 | 696 | 45 | 593 | 97 | 945 | 35 | NB |
| H4H1745P | 115 | 226 | 207 | 71 | 141 | 221 | 281 | 74 | NB |
| H4H1750P | 204 | 623 | 244 | 335 | 52.7 (nM) | 4 | 456 (nM) | 1 | NB |
| H4H1752P | NB | NB | NB | NB | 274 | 122 | 1320 | 29 | NB |
| H2M1804N | 192 | 108 | NT | NT | 176 | 172 | 218 | 118 | NB |
| H2M1805N | NB | NB | NT | NT | 345 | 67 | 439 | 36 | NB |
| H2M1817N | 451 | 57 | NT | NT | 1250 | 37 | 1.0 (nM) | 30 | NB |
| H2M1818N | 1080 | 17 | NT | NT | 1840 | 10 | 4.1 (nM) | 3 | 171 (nM) |

Experiment 4

Inhibition of TL1A by Anti-hTL1A Antibodies

HEK293 cell lines (CRK01573, ATCC) were generated to stably express human DR3 (full-length; SEQ ID NO:252) or mouse DR3 (full-length; SEQ ID NO:259) along with a luciferase reporter [NFκB response element (5×)-luciferase-IRES-GFP]. NFκB activation by TL1A has been shown previously (Migone et al., 2002, *Immunity* 16:479-492). In order to test the membrane-bound form of TL1A and TL1A variants, HEK293 cell lines were generated that stably express full length human TL1A (SEQ ID NO:244), full-length human TL1A with Gln-167 substituted by Arg [Fhm; TL1A (Q167R); SEQ ID NO:246], full-length TL1A from cynomolgus monkey, *Macaca fascicularis* (MfTL1A; SEQ ID NO:248), full length mouse TL1A (SEQ ID NO:250), and full length rat TL1A (SEQ ID NO:258). The stable cell lines were isolated and maintained in 10% fetal bovine serum (FBS; Irvine Scientific), Dulbecco's Modified Eagle Medium(D-MEM; Irvine Scientific), non-essential amino acids (NEAA; Irvine Scientific), Penicillin/Streptomycin (Invitrogen), and 6418 (Invitrogen).

For the bioassay, human or mouse DR3 reporter cells were seeded into 96-well assay plates at $1×10^4$ cells/well in low serum media, i.e., 0.1% FBS and OPTIMEM® (Invitrogen), and incubated at 37° C. and 5% $CO_2$ overnight. The next day, soluble TL1A or FHM (sTL1A or sFHM) was serially diluted at 1:3 and added to cells at concentrations ranging from 0.002 nM to 100 nM (plus a buffer control containing no TL1A). For inhibition, antibodies were serially diluted at 1:3 and added to cells at concentrations ranging from 0.002 nM to 100 nM (plus a buffer control containing no antibody) in the presence of constant concentrations of TL1A or Fhm: 800 pM hTL1A (CHO cell-expressed; residues 72-251 of SEQ ID NO:244, with N-terminal $His_6$-tag), 100 pM hTL1A (*E. coli*-expressed; residues 72-251 of SEQ ID NO:244, with or without N-terminal Met), 500 pM Fhm (CHO cell-expressed; residues 72-251 of SEQ ID NO:246), 400 pM MfTL1A (CHO cell-expressed; residues 72-251 of SEQ ID NO:248, with N-terminal $His_6$-tag), 400 pM MfTL1A (*E. coli*-expressed; residues 72-251 of SEQ ID NO:248, with or without N-terminal Met), 50 pM mouse TL1A (CHO cell-expressed; residues 76-252 of SEQ ID NO:250, with N-terminal $His_6$-tag), 20 pM mouse TL1A (*E. coli*-expressed; residues 76-252 of SEQ ID NO:250, with or without N-terminal Met), and 50 pM rat TL1A (CHO cell-expressed; residues 76-252 of SEQ ID NO:258, with N-terminal $His_6$-tag). Luciferase activity was detected after 5.5 hours of incubation at 37° C. and 5% $CO_2$. The results are shown in Table 6. Control mAb1: Positive control (an anti-hTL1A antibody with heavy and light chain variable domains having the amino acid sequences corresponding to SEQ ID NOS:21 and 27 of US 2009/0280116); control mAb2: Negative control (irrelevant antibody); NB: No binding under the conditions tested; NT: Not tested in this assay; *: Inhibition is not to baseline at the highest antibody concentration of 100 nM.

TABLE 6

| | sTL1A or sFhm | hTL1A (CHO) | hTL1A (*E. Coli*) | Fhm (CHO) | MfTL1A (CHO) | MfTL1A (*E. Coli*) | mTL1A (CHO) | mTL1A (*E. Coli*) | rTL1A (CHO) |
|---|---|---|---|---|---|---|---|---|---|
| | EC50 (nM) | 0.63 | 0.12 | 0.32 | 0.86 | 2.02 | 0.08 | 0.01 | 0.06 |
| | Constant TL1A or Fhm (pM) | 800 | 100 | 500 | 400 | 400 | 50 | 20 | 50 |
| IC50 [nM] | H4H1681N | 0.17 | 0.02 | NB | 0.03 | 0.02 | NB | NB | NB |
| | H4H1704N | 0.13 | 0.06 | 0.17 | 0.01 | 0.03 | NB | NB | 0.40 |
| | H4H1804N | 0.07 | 0.03 | 0.10 | 0.03 | 0.02 | NB | NB | 3.64 |
| | H4H1805N | 0.10 | 0.04 | 185.50* | 0.03 | 0.02 | NB | NB | NB |
| | H4H1817N | 0.11 | 0.04 | 0.12 | 0.04 | 0.02 | NB | NB | 23.87 |
| | H4H1818N | 0.37 | 0.29 | 0.62 | 0.13 | 0.06 | NB | NB | 1.10 |
| | H4H1719P | 0.06 | 0.02 | 0.08 | 0.01 | 0.02 | NT | NB | NT |
| | H4H1725P | 0.05 | 0.02 | 0.07 | 0.01 | 0.02 | NB | NB | 63.43 |
| | H4H1738P | 0.39 | 0.16 | 0.33 | 0.39 | 0.07 | NT | NB | NT |
| | H4H1742P | 0.31 | 0.19 | 0.53 | 0.26 | 0.07 | NB | NB | 6.12 |
| | H4H1745P | 0.09 | 0.06 | 0.15 | 0.05 | 0.03 | NB | NB | NB |
| | H4H1750P | 0.90 | 2.17 | 3.10 | 154.70 | 32.47* | NT | NB | NT |
| | H4H1752P | 0.36 | 0.21 | NB | 0.12 | 0.05 | NT | NB | NT |
| | Control mAb1 | NB | 0.74 | NB | NB | 3.25 | NT | NB | NT |
| | Control mAb2 | NB | NB | NB | NB | NB | NB | NT | NB |

As shown in Table 6, thirteen anti-TL1A antibodies were shown to inhibit soluble human TL1A (CHO and *E. coli*-expressed) stimulation of the human DR3 receptor expressed on HEK293 cells as determined using a luciferase reporter for NFκB activation. A positive control antibody (control mAb1) inhibited *E. coli*-expressed, but not CHO-expressed, hTL1A. Ten antibodies also inhibited stimulation of hDR3-expressing cells by Fhm (hTL1A with Q167R). H4H1681N, H4H1805N and H4H1752P did not fully inhibit Fhm at the highest antibody concentration of 100 nM. All thirteen antibodies also blocked MfTL1A (Table 6). Mouse TL1A (produced from both CHO and *E. coli*) stimulated NFκB activation in the hDR3 reporter cells; however, none of the 13 anti-human TL1A antibodies inhibited *E. coli*-expressed mouse TL1A in this assay (Table 6). Nine selected antibodies were further tested and did not demonstrate blocking of CHO-expressed mouse TL1A in this assay (Table 6).

To test the ability of TL1A expressed on cells to stimulate signaling in the hDR3 reporter system, bioassays were performed as described above for soluble TL1A with the following changes: Adherent HEK293/TL1A cells were dissociated using Enzyme-Free Dissociation Solution (Chemicon) and added to adherent hDR3 reporter cells after serially diluting the TL1A cells at 1:2 starting from $2×10^5$ cells to 195 cells (plus a no-cell control). For inhibition by antibodies, $1×10^4$ cells were added together with serially diluted antibodies from 100 nM to 0.002 nM (plus a control containing no antibody). The results are shown in Table 7. Control mAb1 and mAb2: Same as the assays above. NB: No binding under the conditions tested; NT: Not tested in this assay; *: Inhibition is not to baseline at the highest antibody concentration of 100 nM.

TABLE 7

| Cell-Bound TL1A or Fhm | | HEK293/ hTL1A | HEK293/ Fhm | HEK293/ MfTL1A | HEK293/ mTL1A | HEK293/ rTL1A |
|---|---|---|---|---|---|---|
| EC50 (cells) | | 23474 | 47921 | 8465 | 12366 | 9773 |
| Constant TL1A or Fhm (# cells) | | | | 10,000 | | |
| IC50 [nM] | H4H1681N | 0.66 | NB | 3.07 | NT | NT |
| | H4H1704N | 1.11 | 1.58 | 3.76 | NB | NT |
| | H4H1804N | 0.56 | 1.23 | 2.23 | NB | 3.99 |
| | H4H1805N | 0.82 | 54.10* | 1.93 | NB | NB |
| | H4H1817N | 1.11 | 0.62 | 5.04 | NB | 94.96* |
| | H4H1818N | 1.54 | 1.42 | 4.29 | NT | NT |
| | H4H1719P | 0.82 | 0.84 | 3.00 | NT | NT |
| | H4H1725P | 0.66 | 0.94 | 2.82 | NB | 190.30* |
| | H4H1738P | 7.47 | 7.75 | 20.25 | NT | NT |
| | H4H1742P | 6.55 | 8.39 | 18.45 | NB | NT |
| | H4H1745P | 0.76 | 2.12 | 4.28 | NT | NT |
| | H4H1750P | 12.82 | 29.52* | 107.40* | NT | NT |
| | H4H1752P | 1.99 | 138.10* | 11.67 | NT | NT |
| | Control mAb1 | NB | NB | NB | NB | NT |
| | Control mAb2 | NB | NB | NB | NB | NB |

As shown in Table 7, all thirteen antibodies blocked the stimulation of hDR3-expressing cells by hTL1A expressed on cells. With cell-bound Fhm, all antibodies inhibited significantly except H4H1681N, H4H1805N, H4H1750P and H4H1752P, which did not inhibit fully at the highest tested antibody concentration of 100 nM. With cell-bound MfTL1A, all antibodies inhibited, except H4H1750 that did not inhibit completely at the highest tested antibody concentration of 100 nM. Six of the antibodies H4H1704N, H4H1804N, H4H1805N, H4H1817N, H4H1725P, and H4H1742P were tested for blocking cell-surface mTL1A stimulation of mDR3 cells; and none showed inhibition. Reporter cells expressing mouse DR3 could also be stimulated by rTL1A-expressing 293 cells, with an observed EC$_{50}$ of 9773 cells (Table 7). Four antibodies were tested in the rTL1A/mDR3 assay: three antibodies H4H1804N, H4H1817N, H4H1725P blocked while H4H1805N did not block stimulation of mDR3 cells by cell-surface rTL1A (Table 7). Control mAb1 blocked E. coli-expressed soluble hTL1A and MfTL1A stimulation of hDR3 cells, but failed to block the CHO-expressed forms of hTL1A and MfTL1A under all tested conditions (Table 6). Control mAb1 also did not inhibit stimulation of hDR3-expressing cells by any of the cell-surface expressed TL1A and Fhm under all tested conditions (Table 7).

Experiment 5

Blocking of TL1A to hDR3 and DcR3 by Anti-TL1A Antibodies

The ability of antibodies to block human TL1A binding to its cognate receptors, the DR3 and DcR3 receptors, was measured using a competition sandwich ELISA. In addition, blocking of a human TL1A variant FHM (human TL1A Q167R) and the cynomolgus monkey (Macaca fascicularis) TL1A (MfTL1A) protein binding to the human DR3 or DcR3 receptors was measured in the same manner. Constant amounts of biotinylated human TL1A or FHM (both expressed with a 6-His tag in CHO cells) or biotinylated MfTL1A (expressed in CHO cells) were separately titrated with varying amounts of antibodies. The antibody-protein complexes were incubated in solution (1 hr, 25° C.) and then transferred to microtiter plates coated with human DR3 (hDR3) or human DcR3 (hDcR3) expressed as human IgG1 Fc fusion proteins. After one hour at 25° C. the wells were washed, and bound human or monkey TL1A was detected with streptavidin conjugated with horseradish peroxidase (HRP). Wells were developed with a TMB solution to produce a colorimetric reaction and quenched with aqueous sulfuric acid before reading absorbance at 450 nm on a Perkin-Elmer Victor X5 plate reader. A sigmoidal dose-response curve was fit to the data using the Prism™ data analysis package. The calculated IC50 value, defined as the concentration of antibody required to block 50% of TL1A binding to hDR3 or hDcR3, was used as an indicator of blocking potency. Both fully human anti-hTL1A mAbs and comparator antibodies, i.e., control mAb1 (an anti-hTL1A antibody with heavy and light chain variable domains having the amino acid sequences corresponding to SEQ ID NOS:21 and 27, respectively, of US 2009/0280116) and control mAb3 (an anti-hTL1A antibody with heavy and light chain variable domains having the amino acid sequences corresponding to SEQ ID NOS:57 and 48, respectively, of US 2009/0280116), were included in the study. The results are shown in Table 8. NB: No binding under the conditions tested; NT: Not tested. Concentrations of biotinylated soluble ligands: (1) 150 pM; (2) 500 pM; (3) 10 pM; and (4) 50 pM.

As shown in Table 8, most of the fully human mAbs show effective blocking of the TL1A/hDR3 and TL1A/hDcR3 binding interaction, with several showing IC50 values below 50 pM. Two of the antibodies, H4H1752P and H4H1805N, strongly blocked binding of both human and monkey TL1A binding to both hDR3 and hDcR3 but failed to block binding of FHM to either hDR3 or hDcR3, suggesting that the binding epitope for these two antibodies may involve the region near the FHM mutation site (hTL1A with Q167R). The crystal structure of hTL1A shows that residue Q167 occurs within a surface-exposed loop (Zhan et al., 2009, Biochemistry 48: 7636-7645).

TABLE 8

| mAb ID | hDR3 hTL1A (CHO)[1] IC$_{50}$ (pM) | hDR3 FHM (CHO)[1] IC$_{50}$ (pM) | hDR3 MfTL1A (CHO)[2] IC$_{50}$ (pM) | DcR3 hTL1A (CHO)[3] IC$_{50}$ (pM) | DcR3 FHM (CHO)[3] IC$_{50}$ (pM) | DcR3 MfTL1A (CHO)[4] IC$_{50}$ (pM) |
|---|---|---|---|---|---|---|
| H4H1681N | 60 | >10000 | 141 | 17 | 90 | 93 |
| H2M1681N | 37 | >10000 | 61 | 13 | 234 | 149 |
| H4H1704N | 30 | 44 | 42 | 77 | 170 | 110 |
| H2M1704N | NT | NT | NT | NT | NT | NT |
| H4H1719P | 22 | 23 | 46 | 44 | 45 | 61 |
| H4H1725P | 15 | 18 | 16 | 68 | 85 | 145 |
| H4H1738P | 69 | 152 | 117 | 122 | 150 | 68 |
| H4H1742P | 64 | 214 | 240 | 181 | 231 | 127 |
| H4H1745P | 18 | 44 | 50 | 58 | 85 | 118 |
| H4H1750P | 341 | 589 | 5209 | 656 | 626 | NB |
| H4H1752P | 104 | NB | 110 | 31 | NB | 56 |
| H4H1804N | 40 | 69 | 71 | 175 | >10000 | 34 |
| H2M1804N | 46 | 102 | 81 | 120 | >10000 | 9 |
| H4H1805N | 14 | NB | 26 | 33 | 436 | 313 |
| H2M1805N | 6 | NB | 13 | 12 | 2241 | 1138 |
| H4H1817N | 114 | 235 | 101 | 270 | NT | 322 |
| H2M1817N | 154 | 249 | 137 | 890 | 666 | 776 |
| H4H1818N | 119 | 202 | 123 | 232 | NT | 1102 |
| H2M1818N | 154 | 317 | 239 | 396 | NB | 55 |
| Control mAb1 | >10000 | NB | 5300 | >1000 | NT | 21000 |
| Control mAb3 | >10000 | NB | 17000 | 8600 | NT | NT |

Example 6

Cell Surface Binding Competition of Anti-TL1A Antibodies with Soluble hTL1A

Human embryonic kidney 293 cells stably transfected to over-express cell-surface hTL1A were first stained in a flow cytometric experiment with eight anti-hTL1A antibodies at four concentrations (1, 0.1, 0.01, and 0.003 μg/ml). Bound human antibodies were detected using an allophycocyanin-labeled goat F(ab')$_2$ specific for human Fcγ [or anti-hFcγ-APC F(ab')$_2$, Jackson ImmunoResearch, #109-136-170]. The lowest antibody concentration providing significant staining levels was then used in a competition binding experiment. A negative isotype control antibody (human IgG4) was used at 1 μg/ml to define the background signal. For the competition experiment, eight antibody samples, at the minimal concentrations identified above, were first treated with soluble hTL1A expressed from CHO cells at concentrations ranging from 0.03 μg/ml to 10 μg/ml. After pre-incubation for 30 min on ice, the antibody/hTL1A mixture was added to 293/HEK-hTL1A cells that had been isolated by centrifugation in a 96-well conical plate. After incubation for an additional 10 minutes on ice, the cells were washed. The secondary reagent, anti-hFcγ-APC F(ab')$_2$, was added to all wells at a 200-fold dilution to detect bound antibodies. Samples were incubated for 15 minutes on ice, away from light, and then washed. Cells were processed on an BD™ LSR II Flow Cytometer (BD Biosciences) to detect anti-hTL1A antibodies bound to the cell surface, and data were analyzed using FlowJo software (version 8.8.6; Tree Star Inc.). The results are shown in Table 9. Maximum signal: Anti-hTL1A antibody binding in the absence of soluble hTL1A; Minimum signal: Signal recorded when 1 μg/ml of isotype control antibody was added in place of the anti-hTL1A antibody. NT: Not tested.

TABLE 9

| Soluble hTL1A (μg/ml) | Mean Fluorescence Intensity for anti-hTL1A antibodies (H4H) binding to cell-surface hTL1A | | | | | | | |
|---|---|---|---|---|---|---|---|---|
| | 1704N 0.1 μg/ml | 1725P 0.1 μg/ml | 1742P 1 μg/ml | 1804N 0.1 μg/ml | 1805N 0.1 μg/ml | 1817N 1 μg/ml | 1681N 1 μg/ml | 1745P 1 μg/ml |
| 10 | NT | NT | NT | NT | NT | NT | 16.9 | 15 |
| 3 | 22.6 | 34.9 | 19.9 | 28.9 | 23.6 | 25.2 | 28.5 | 19.5 |
| 1 | 26 | 29.2 | 32.7 | 33.7 | 25.1 | 29.1 | 80.9 | 26.9 |
| 0.3 | 31.5 | 40.7 | 44.7 | 33.5 | 36.8 | 23.6 | 236 | 115 |
| 0.1 | 132 | 84.5 | 79.4 | 51.1 | 60.2 | 97.2 | 327 | 93.1 |
| 0.03 | 163 | 207 | 126 | 126 | 156 | 85.3 | 318 | 80 |
| Maximum signal | 116 | 211 | 126 | 127 | 158 | 110 | 320 | 87.2 |
| Minimum signal | 27.5 | 27.5 | 27.5 | 27.5 | 27.5 | 27.5 | 17.9 | 17.9 |

As shown in Table 9, the signals from the eight tested antibodies could be competed down to baseline levels by the addition of excess soluble hTL1A, demonstrating the specificity of binding of the antibodies to cell-surface hTL1A.

Example 7

Blocking of hTL1A-Dependent CD4+ T-cell Stimulation by Anti-TL1A Antibodies

To determine the ability of anti-hTL1A antibodies to block hTL1A-dependent stimulation of human CD4+ T-cells, an in vitro assay was developed in which hTL1A/anti-CD3/anti-CD28-stimulated release of IFN-gamma (IFN-γ) was measured in the presence or absence of antibodies. Human CD4+ T-cells were isolated from fresh buffy coats prepared from human blood samples obtained from the New York Blood Center. Cells from a single donor were kept separate from other donor cells for each assay. The CD4+ T-cells were added to the wells of a 96-well plate at 3.5×10$^5$ cells per well. To each well was then added soluble hTL1A (residues 72-251 of NP 005109.2 with an N-terminal hexa-histidine tag, expressed from CHO cells) to a final concentration of 1 μg/ml (16 nM, assuming hTL1A forming trimers in solution) in RPMI +10% FBS, L-glutamine and penicillin/streptomycin. To each well was also added the anti-hTL1A antibodies or an isotype control antibody to final concentrations of 1.0 μg/ml or 3.0 μg/ml (6.7 nM or 20 nM, respectively). The samples were incubated for 15 minutes at 4° C. in the dark, followed by the additions of anti-hCD3 (BD Pharmingen, cat #555336) and anti-hCD28 (BD Pharmingen, cat # 555725) to each well to final concentrations of 1.0 μg/ml. Samples were incubated for 24 hours at 37° C., the supernatants harvested, and IFN-γ levels determined by ELISA. The blocking effect (average from two separate wells for each condition) of each antibody on each human CD4+ T-cell donor sample is represented as the reduction from maximal signal divided by maximal response window; i.e., % Blocking=[(Max−Inhib)/(Max−Min)]×100, where "Max", "Inhib", and "Min" are concentrations of IFN-γ measured for CD4+ human T-cells treated as follows: "Max"—treated with [hTL1A+anti-hCD3+anti-hCD28+isotype control mAb]; "Min:"—treated with [anti-hCD3+anti-hCD28+isotype control mAb]; and "Inhib"—treated with [hTL1A+anti-hCD3+anti-hCD28+anti-hTL1A test mAb]. Antibodies for which IFN-γ blockade surpassed the "Min" baseline level are represented as 100% blockade. Ratio (Max/Min) is the ratio of the IFN-γ concentration produced from human CD4+ T-cells treated under Max and Min conditions as defined above.

As shown in Table 10, the antibodies H4H1725P, H4H1805N, H4H1817N, and H4H1804N significantly blocked hTL1A-stimulated IFN-γ release at both 1 μg/ml and 3 μg/ml concentrations, with nearly complete blockade (>80%) observed for most donors at the higher antibody concentration. The results for blockade of IFN-γ secretion by thirteen different anti-hTL1A antibodies against CD4+ T-cells from 10 different human donors are further summarized in Table 11. SD: Standard deviation.

TABLE 10

| | | % Blocking of IFN-γ production in human T-cells from 10 donors | | | | | | | | | |
|---|---|---|---|---|---|---|---|---|---|---|---|
| | | Donor # | | | | | | | | | |
| mAb ID | Ratio (Max/Min) | D1 5 | D2 4 | D3 10 | D4 10 | D5 4 | D6 3 | D7 4 | D8 3 | D9 8 | D10 2 |
| H4H1725P | mAb | 90 | 100 | 70 | 85 | 45 | 80 | 60 | 85 | 50 | 95 |
| H4H1805N | 1 μg/ml | 100 | 100 | 90 | 100 | 100 | 100 | 100 | 100 | 90 | 100 |
| H4H1817N | (6.7 nM) | 100 | 100 | 90 | 90 | 100 | 45 | 55 | 100 | 55 | 80 |
| H4H1804N | | 95 | 100 | 80 | 90 | 100 | 50 | 10 | 100 | 50 | 0 |
| H4H1725P | mAb | 95 | 100 | 95 | 100 | 90 | 80 | 90 | 100 | 90 | 100 |
| H4H1805N | 3 μg/ml | 100 | 100 | 95 | 100 | 80 | 100 | 100 | 100 | 70 | 100 |
| H4H1817N | (20 nM) | 100 | 100 | 100 | 100 | 100 | 100 | 100 | 100 | 95 | 85 |
| H4H1804N | | 100 | 100 | 95 | 100 | 100 | 100 | 100 | 100 | 100 | 80 |

TABLE 11

| mAb ID | Average % Blocking (SD) 0.1 μg/ml mAb | Average % Blocking (SD) 1 μg/ml mAb | Average % Blocking (SD) 3 μg/ml mAb |
|---|---|---|---|
| H4H1681N | 20% (24) | 45% (30) | 95% (7) |
| H4H1704N | 22% (29) | 53% (27) | 98% (5) |
| H4H1719P | 10% (22) | 37% (23) | 78% (30) |
| H4H1725P | 13% (14) | 80% (20) | 94% (7) |
| H4H1738P | 25% (30) | 41% (35) | 81% (18) |
| H4H1742P | 10% (22) | 58% (33) | 83% (16) |
| H4H1745P | 22% (27) | 36% (36) | 91% (7) |
| H4H1750P | 11% (14) | 42% (35) | 89% (15) |
| H4H1752P | 18% (25) | 52% (35) | 71% (30) |
| H4H1804N | 26% (30) | 68% (38) | 98% (6) |
| H4H1805N | 21% (28) | 98% (4) | 94% (10) |
| H4H1817N | 25% (33) | 81% (22) | 98% (5) |
| H4H1818N | 25% (33) | 42% (33) | 71% (35) |
| Isotype Control | 16% (21) | 26% (33) | 28% (27) |

IFN-γ levels were also measured at six different antibody concentrations (ranging from 0.03 μg/ml to 10 μg/ml) for each of six different antibodies added to CD4+ T-cells from twelve human donors. Curve fitting to the data allowed estimation of the antibody concentration at which half-maximal inhibition was achieved for each antibody for each donor cell sample. The average (±SD) concentrations for achieving half-maximal inhibition are provided in Table 12.

TABLE 12

| Donor # | mAb IC$_{50}$ (nM) | | | | | |
|---|---|---|---|---|---|---|
| | H4H1725P | H4H1742P | H4H1805N | H4H1817N | H4H1804N | H4H1704N |
| D1 | 3.4 | 24 | 2.4 | 6.6 | 6.8 | — |
| D2 | 3.2 | 4.6 | 5.5 | 3.1 | 8.6 | — |
| D3 | 5.4 | 10 | 3.4 | 4.7 | 8.6 | — |
| D4 | 4.7 | 13 | 2.5 | 2.4 | 7.7 | — |
| D5 | 7.0 | 12 | 2.9 | 8.5 | 6.7 | 17 |
| D6 | 5.4 | 10 | 3.4 | 4.7 | 8.6 | 11 |
| D7 | 13 | 31 | 8.0 | 7.0 | 12 | 12 |
| D8 | 12 | 27 | 5.1 | 7.0 | 11 | 19 |
| D9 | 6.4 | 56 | 5.9 | 9.5 | 8.1 | 7.5 |
| D10 | 4.1 | 12 | 2.8 | 7.3 | 12 | 10 |
| D11 | 6.1 | 27 | 3.0 | 7.3 | 7.6 | 11 |
| D12 | 6.4 | 14 | 3.1 | 9.4 | 7.5 | 8.0 |
| Average | 6.4 | 20 | 4.0 | 6.5 | 8.8 | 12 |
| (±SD) | (3.1) | (14) | (1.7) | (2.3) | (1.9) | (4.1) |

Four of the antibodies, H4H1725P, H4H1804N, H4H1805N, H4H1817N exhibited average half-maximal inhibition concentrations below 10 nM (ranging approximately 4-9 nM).

---

The invention claimed is:

1. An isolated human antibody or antigen-binding fragment thereof that specifically binds human TNF-like ligand 1A (hTL1A), comprising a heavy chain complementarity determining region 1 (HCDR1), HCDR2 and HCDR3 sequence combination of SEQ ID NO:20/22/24; and/or a light chain complementarity determining region 1 (LCDR1), LCDR2 and LCDR3 sequence combination of SEQ ID NO:28/30/32.

2. The antibody or antigen-binding fragment according to claim 1, wherein heavy and light chain CDR sequences, HCDR1/HCDR2/HCDR3/LCDR1/LCDR2/LCDR3, comprise a CDR sequence combination of SEQ ID NO:20/22/24/28/30/32.

3. The antibody or antigen-binding fragment of claim 1, wherein the antibody or antigen-binding fragment comprises a heavy chain variable region (HCVR) comprising the amino acid sequence of SEQ ID NO:18.

4. The antibody or antigen-binding fragment of claim 1, wherein the antibody or antigen-binding fragment comprises a light chain variable region (LCVR) comprising the amino acid sequence of SEQ ID NO:26.

5. The antibody or antigen-binding fragment of claim 2, wherein the antibody or fragment does not cross-react with Fhm comprising the amino acid sequence of SEQ ID NO:246.

6. An antibody or antigen-binding fragment thereof which binds the same epitope on hTL1A as an antibody or antigen-binding fragment comprising heavy chain and light chain complementarity determining regions (CDRs) of SEQ ID NO:20/22/24/28/30/32.

7. An isolated human antibody or antigen-binding fragment thereof that specifically binds human TNF-like ligand 1A (hTL1A), comprising a heavy chain variable region (HCVR) comprising an amino acid sequence of SEQ ID NO:18 and/or a light chain variable region (LCVR) comprising an amino acid sequence of SEQ ID NO: 26.

8. The antibody or antigen-binding fragment of claim 7, comprising a HCVR/LCVR sequence pair of SEQ ID NO:18/26.

9. An isolated nucleic acid molecule encoding the antibody or antigen-binding fragment of claim 1.

10. An expression vector comprising the nucleic acid molecule of claim 9.

11. An isolated host cell comprising the expression vector of claim 10.

12. A method of producing an anti-hTL1A antibody or antigen-binding fragment thereof, comprising growing the host cell of claim 11 under conditions permitting production of the antibody or fragment thereof, and recovering the antibody or fragment thereof so produced.

13. A pharmaceutical composition comprising the antibody or antigen-binding fragment of claim 1, wherein the antibody or antigen-binding fragment thereof further neutralizes hTL1A, and a pharmaceutically acceptable carrier.

* * * * *

SEQUENCE LISTING

<160> NUMBER OF SEQ ID NOS: 259

<210> SEQ ID NO 1
<211> LENGTH: 366
<212> TYPE: DNA
<213> ORGANISM: Artificial Sequence
<220> FEATURE:
<223> OTHER INFORMATION: Synthetic

<400> SEQUENCE: 1
gaggtgcagc tggtggagtc tgggggaggc ttggtccagc ctggggggtc cctgagactc    60
tcctgtgcag tctctggatt cacctttagt agttattgga tgagctgggt ccgccaggct   120
ccagggaagg ggctggaatg ggtggccaac ataaaggaag atggaagtga aaaaactat    180 gtggactctg tgaagggccg attcacccctc tccagcgaca cgccaagaa ctcactgtat   240 ctgcaaatga acagcctgag agccgaggac acggctgttt attactgtgc gagagaggac   300
tatgactcct actacaagta cggtatggac gtttggggcc aagggaccgc ggtcatcgtc   360
tcctca                                                              366

<210> SEQ ID NO 2
<211> LENGTH: 122
<212> TYPE: PRT
<213> ORGANISM: Artificial Sequence
<220> FEATURE:
<223> OTHER INFORMATION: Synthetic

<400> SEQUENCE: 2

Glu Val Gln Leu Val Glu Ser Gly Gly Gly Leu Val Gln Pro Gly Gly
 1               5                  10                  15

Ser Leu Arg Leu Ser Cys Ala Val Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Glu Asp Gly Ser Glu Lys Asn Tyr Val Asp Ser Val
    50                  55                  60

Lys Gly Arg Phe Thr Leu Ser Ser Asp Asn Ala Lys Asn Ser Leu Tyr
65                  70                  75                  80

```
Leu Gln Met Asn Ser Leu Arg Ala Glu Asp Thr Ala Val Tyr Tyr Cys
                85                  90                  95

Ala Arg Glu Asp Tyr Asp Ser Tyr Tyr Lys Tyr Gly Met Asp Val Trp
            100                 105                 110

Gly Gln Gly Thr Ala Val Ile Val Ser Ser
        115                 120
```

```
<210> SEQ ID NO 3
<211> LENGTH: 24
<212> TYPE: DNA
<213> ORGANISM: Artificial Sequence
<220> FEATURE:
<223> OTHER INFORMATION: Synthetic

<400> SEQUENCE: 3
ggattcacct ttagtagtta ttgg                                          24

<210> SEQ ID NO 4
<211> LENGTH: 8
<212> TYPE: PRT
<213> ORGANISM: Artificial Sequence
<220> FEATURE:
<223> OTHER INFORMATION: Synthetic

<400> SEQUENCE: 4

Gly Phe Thr Phe Ser Ser Tyr Trp
 1               5

<210> SEQ ID NO 5
<211> LENGTH: 24
<212> TYPE: DNA
<213> ORGANISM: Artificial Sequence
<220> FEATURE:
<223> OTHER INFORMATION: Synthetic

<400> SEQUENCE: 5
ataaaggaag atggaagtga gaaa                                          24

<210> SEQ ID NO 6
<211> LENGTH: 8
<212> TYPE: PRT
<213> ORGANISM: Artificial Sequence
<220> FEATURE:
<223> OTHER INFORMATION: Synthetic

<400> SEQUENCE: 6

Ile Lys Glu Asp Gly Ser Glu Lys
 1               5

<210> SEQ ID NO 7
<211> LENGTH: 45
<212> TYPE: DNA
<213> ORGANISM: Artificial Sequence
<220> FEATURE:
<223> OTHER INFORMATION: Synthetic

<400> SEQUENCE: 7
gcgagagagg actatgactc ctactacaag tacggtatgg acgtt                   45

<210> SEQ ID NO 8
<211> LENGTH: 15
<212> TYPE: PRT
<213> ORGANISM: Artificial Sequence
<220> FEATURE:
<223> OTHER INFORMATION: Synthetic

<400> SEQUENCE: 8
```

Ala Arg Glu Asp Tyr Asp Ser Tyr Tyr Lys Tyr Gly Met Asp Val
 1               5                  10                  15

<210> SEQ ID NO 9
<211> LENGTH: 339
<212> TYPE: DNA
<213> ORGANISM: Artificial Sequence
<220> FEATURE:
<223> OTHER INFORMATION: Synthetic

<400> SEQUENCE: 9
gacatcgtga tgacccagtc tccagactcc ctggctgtgt ctctgggcga gagggccacc     60
atcaactgca agtccagcca gagtatttta tacagctcca acaataagaa ctacttagct    120
tggtatcagc agaaaccagg acagcctcct aagctgctca tttactgggc atctacccgg    180
gaatccgggg tccctgaccg attcagtggc agcgggtctg gaacagattt cactctcacc    240
atcagcagcc tgcaggctga agatgtgtca gtttattact gtcaacaata ttatagtact    300
ccattcactt tcggccctgg gaccaaagtg gatatcaaa                           339

<210> SEQ ID NO 10
<211> LENGTH: 113
<212> TYPE: PRT
<213> ORGANISM: Artificial Sequence
<220> FEATURE:
<223> OTHER INFORMATION: Synthetic

<400> SEQUENCE: 10

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Ile Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ser Val Tyr Tyr Cys Gln Gln
                85                  90                  95

Tyr Tyr Ser Thr Pro Phe Thr Phe Gly Pro Gly Thr Lys Val Asp Ile
            100                 105                 110

Lys

<210> SEQ ID NO 11
<211> LENGTH: 36
<212> TYPE: DNA
<213> ORGANISM: Artificial Sequence
<220> FEATURE:
<223> OTHER INFORMATION: Synthetic

<400> SEQUENCE: 11
cagagtattt tatacagctc caacaataag aactac                               36

<210> SEQ ID NO 12
<211> LENGTH: 12
<212> TYPE: PRT
<213> ORGANISM: Artificial Sequence
<220> FEATURE:
<223> OTHER INFORMATION: Synthetic

<400> SEQUENCE: 12

Gln Ser Ile Leu Tyr Ser Ser Asn Asn Lys Asn Tyr
  1               5                   10

<210> SEQ ID NO 13
<211> LENGTH: 9
<212> TYPE: DNA
<213> ORGANISM: Artificial Sequence
<220> FEATURE:
<223> OTHER INFORMATION: Synthetic

<400> SEQUENCE: 13 tgggcatct                                                                 9

<210> SEQ ID NO 14
<211> LENGTH: 3
<212> TYPE: PRT
<213> ORGANISM: Artificial Sequence
<220> FEATURE:
<223> OTHER INFORMATION: Synthetic

<400> SEQUENCE: 14

Trp Ala Ser
  1

<210> SEQ ID NO 15
<211> LENGTH: 27
<212> TYPE: DNA
<213> ORGANISM: Artificial Sequence
<220> FEATURE:
<223> OTHER INFORMATION: Synthetic

<400> SEQUENCE: 15
caacaatatt atagtactcc attcact                                            27

<210> SEQ ID NO 16
<211> LENGTH: 9
<212> TYPE: PRT
<213> ORGANISM: Artificial Sequence
<220> FEATURE:
<223> OTHER INFORMATION: Synthetic

<400> SEQUENCE: 16

Gln Gln Tyr Tyr Ser Thr Pro Phe Thr
  1               5

<210> SEQ ID NO 17
<211> LENGTH: 363
<212> TYPE: DNA
<213> ORGANISM: Artificial Sequence
<220> FEATURE:
<223> OTHER INFORMATION: Synthetic

<400> SEQUENCE: 17
gaggtgcaac tattggagtc tgggggaggc ttggtgcagc ctgggaagtc ccttagactc        60
tcctgtgcag tctctggatt cacctttagt acctatggca tgaattgggt ccgccaggct       120
ccagggaagg ggctggagtg gtctcaagt attagtggta ctggtcgtac cacataccat        180
gcagactccg tgcagggccg gttcaccgtc tccagagaca attccaagaa cattctatat       240
ttacagatga acagtctgcg agccgacgac acgccgtat atttctgtac gaaagagcgg        300
ggagattact actacgggt ttttgactac tggggccagg aaccctggt caccgtctcc         360 tca                                                                     363

<210> SEQ ID NO 18

<211> LENGTH: 121
<212> TYPE: PRT
<213> ORGANISM: Artificial Sequence
<220> FEATURE:
<223> OTHER INFORMATION: Synthetic

<400> SEQUENCE: 18

```
Glu Val Gln Leu Leu Glu Ser Gly Gly Gly Leu Val Gln Pro Gly Lys
 1               5                  10                  15

Ser Leu Arg Leu Ser Cys Ala Val Ser Gly Phe Thr Phe Ser Thr Tyr
            20                  25                  30

Gly Met Asn Trp Val Arg Gln Ala Pro Gly Lys Gly Leu Glu Trp Val
        35                  40                  45

Ser Ser Ile Ser Gly Thr Gly Arg Thr Thr Tyr His Ala Asp Ser Val
50                  55                  60

Gln Gly Arg Phe Thr Val Ser Arg Asp Asn Ser Lys Asn Ile Leu Tyr
65                  70                  75                  80

Leu Gln Met Asn Ser Leu Arg Ala Asp Asp Thr Ala Val Tyr Phe Cys
                85                  90                  95

Thr Lys Glu Arg Gly Asp Tyr Tyr Tyr Gly Val Phe Asp Tyr Trp Gly
            100                 105                 110

Gln Gly Thr Leu Val Thr Val Ser Ser
        115                 120
```

<210> SEQ ID NO 19
<211> LENGTH: 24
<212> TYPE: DNA
<213> ORGANISM: Artificial Sequence
<220> FEATURE:
<223> OTHER INFORMATION: Synthetic

<400> SEQUENCE: 19
ggattcacct ttagtaccta tggc                                         24

<210> SEQ ID NO 20
<211> LENGTH: 8
<212> TYPE: PRT
<213> ORGANISM: Artificial Sequence
<220> FEATURE:
<223> OTHER INFORMATION: Synthetic

<400> SEQUENCE: 20

```
Gly Phe Thr Phe Ser Thr Tyr Gly
 1               5
```

<210> SEQ ID NO 21
<211> LENGTH: 24
<212> TYPE: DNA
<213> ORGANISM: Artificial Sequence
<220> FEATURE:
<223> OTHER INFORMATION: Synthetic

<400> SEQUENCE: 21
attagtggta ctggtcgtac caca                                         24

<210> SEQ ID NO 22
<211> LENGTH: 8
<212> TYPE: PRT
<213> ORGANISM: Artificial Sequence
<220> FEATURE:
<223> OTHER INFORMATION: Synthetic

<400> SEQUENCE: 22

Ile Ser Gly Thr Gly Arg Thr Thr

<210> SEQ ID NO 23
<211> LENGTH: 42
<212> TYPE: DNA
<213> ORGANISM: Artificial Sequence
<220> FEATURE:
<223> OTHER INFORMATION: Synthetic

<400> SEQUENCE: 23
acgaaagagc ggggagatta ctactacggg gtttttgact ac                               42

<210> SEQ ID NO 24
<211> LENGTH: 14
<212> TYPE: PRT
<213> ORGANISM: Artificial Sequence
<220> FEATURE:
<223> OTHER INFORMATION: Synthetic

<400> SEQUENCE: 24

Thr Lys Glu Arg Gly Asp Tyr Tyr Tyr Gly Val Phe Asp Tyr
1               5                   10

<210> SEQ ID NO 25
<211> LENGTH: 318
<212> TYPE: DNA
<213> ORGANISM: Artificial Sequence
<220> FEATURE:
<223> OTHER INFORMATION: Synthetic

<400> SEQUENCE: 25
gacatccaga tgacccagtc tccttccacc ctgtctgcat ctgtaggaga cagagtcacc            60
atcacttgcc gggccagtca gactattagt tcctggttgg cctggtatca gcagacacca          120
gagaaagccc ctaagctcct gatctatgcg gcgtctaatt tacaaagtgg agtcccatca          180
aggttcagcg gcagtggatc tgggacagaa ttcactctca ccatcagcag cctacagcct          240
gatgattttg caacttatta ctgccagcag tatcatcgtt cttggacgtt cggccaaggg          300
accaaggtgg aaatcaca                                                         318

<210> SEQ ID NO 26
<211> LENGTH: 106
<212> TYPE: PRT
<213> ORGANISM: Artificial Sequence
<220> FEATURE:
<223> OTHER INFORMATION: Synthetic

<400> SEQUENCE: 26

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Thr Ile Ser Ser Trp
            20                  25                  30

Leu Ala Trp Tyr Gln Gln Thr Pro Glu Lys Ala Pro Lys Leu Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr His Arg Ser Trp Thr
                85                  90                  95

Phe Gly Gln Gly Thr Lys Val Glu Ile Thr
            100                 105

```
<210> SEQ ID NO 27
<211> LENGTH: 18
<212> TYPE: DNA
<213> ORGANISM: Artificial Sequence
<220> FEATURE:
<223> OTHER INFORMATION: Synthetic

<400> SEQUENCE: 27
cagactatta gttcctgg                                                  18

<210> SEQ ID NO 28
<211> LENGTH: 6
<212> TYPE: PRT
<213> ORGANISM: Artificial Sequence
<220> FEATURE:
<223> OTHER INFORMATION: Synthetic

<400> SEQUENCE: 28

Gln Thr Ile Ser Ser Trp
 1               5

<210> SEQ ID NO 29
<211> LENGTH: 9
<212> TYPE: DNA
<213> ORGANISM: Artificial Sequence
<220> FEATURE:
<223> OTHER INFORMATION: Synthetic

<400> SEQUENCE: 29 gcggcgtct                                                             9

<210> SEQ ID NO 30
<211> LENGTH: 3
<212> TYPE: PRT
<213> ORGANISM: Artificial Sequence
<220> FEATURE:
<223> OTHER INFORMATION: Synthetic

<400> SEQUENCE: 30

Ala Ala Ser
 1

<210> SEQ ID NO 31
<211> LENGTH: 24
<212> TYPE: DNA
<213> ORGANISM: Artificial Sequence
<220> FEATURE:
<223> OTHER INFORMATION: Synthetic

<400> SEQUENCE: 31
cagcagtatc atcgttcttg gacg                                           24

<210> SEQ ID NO 32
<211> LENGTH: 8
<212> TYPE: PRT
<213> ORGANISM: Artificial Sequence
<220> FEATURE:
<223> OTHER INFORMATION: Synthetic

<400> SEQUENCE: 32

Gln Gln Tyr His Arg Ser Trp Thr
 1               5

<210> SEQ ID NO 33
<211> LENGTH: 351
<212> TYPE: DNA
<213> ORGANISM: Artificial Sequence
```

<220> FEATURE:
<223> OTHER INFORMATION: Synthetic

<400> SEQUENCE: 33

```
caggtgcagc tacaccagtg gggcgcagga ctgttgaagc cttcggagac cctgtccctc      60
acctgcgctg tctctggtgt gtccttcagt gattatcact gggcctggat ccgccagtcc     120
ccagggaagg gctggagtg gattgggat atcaatcatc gtggaaggac caactacaac       180
ccgtccctca agagtcgagt caccatatca cttgacacgt ccgggaaccc gttctccctg     240
aagctgacct ctgtgaccgc cgcggacacg gctgtttatt actgtgcgag agattttccc     300
aactgggttt ttgactcctg gggccaggga atcctagtca ccgtctcctc a              351
```

<210> SEQ ID NO 34
<211> LENGTH: 117
<212> TYPE: PRT
<213> ORGANISM: Artificial Sequence
<220> FEATURE:
<223> OTHER INFORMATION: Synthetic

<400> SEQUENCE: 34

Gln Val Gln Leu His Gln Trp Gly Ala Gly Leu Leu Lys Pro Ser Glu
1               5                   10                  15
Thr Leu Ser Leu Thr Cys Ala Val Ser Gly Val Ser Phe Ser Asp Tyr
            20                  25                  30
His Trp Ala Trp Ile Arg Gln Ser Pro Gly Lys Gly Leu Glu Trp Ile
        35                  40                  45
Gly Asp Ile Asn His Arg Gly Arg Thr Asn Tyr Asn Pro Ser Leu Lys
    50                  55                  60
Ser Arg Val Thr Ile Ser Leu Asp Thr Ser Gly Asn Pro Phe Ser Leu
65                  70                  75                  80
Lys Leu Thr Ser Val Thr Ala Ala Asp Thr Ala Val Tyr Tyr Cys Ala
                85                  90                  95
Arg Asp Phe Pro Asn Trp Val Phe Asp Ser Trp Gly Gln Gly Ile Leu
            100                 105                 110
Val Thr Val Ser Ser
        115

<210> SEQ ID NO 35
<211> LENGTH: 24
<212> TYPE: DNA
<213> ORGANISM: Artificial Sequence
<220> FEATURE:
<223> OTHER INFORMATION: Synthetic

<400> SEQUENCE: 35

```
ggtgtgtcct tcagtgatta tcac                                             24
```

<210> SEQ ID NO 36
<211> LENGTH: 8
<212> TYPE: PRT
<213> ORGANISM: Artificial Sequence
<220> FEATURE:
<223> OTHER INFORMATION: Synthetic

<400> SEQUENCE: 36

Gly Val Ser Phe Ser Asp Tyr His
1               5

<210> SEQ ID NO 37
<211> LENGTH: 21
<212> TYPE: DNA

```
<213> ORGANISM: Artificial Sequence
<220> FEATURE:
<223> OTHER INFORMATION: Synthetic

<400> SEQUENCE: 37
atcaatcatc gtggaaggac c                                              21

<210> SEQ ID NO 38
<211> LENGTH: 7
<212> TYPE: PRT
<213> ORGANISM: Artificial Sequence
<220> FEATURE:
<223> OTHER INFORMATION: Synthetic

<400> SEQUENCE: 38

Ile Asn His Arg Gly Arg Thr
 1               5

<210> SEQ ID NO 39
<211> LENGTH: 33
<212> TYPE: DNA
<213> ORGANISM: Artificial Sequence
<220> FEATURE:
<223> OTHER INFORMATION: Synthetic

<400> SEQUENCE: 39
gcgagagatt ttcccaactg ggtttttgac tcc                                 33

<210> SEQ ID NO 40
<211> LENGTH: 11
<212> TYPE: PRT
<213> ORGANISM: Artificial Sequence
<220> FEATURE:
<223> OTHER INFORMATION: Synthetic

<400> SEQUENCE: 40

Ala Arg Asp Phe Pro Asn Trp Val Phe Asp Ser
 1               5                  10

<210> SEQ ID NO 41
<211> LENGTH: 324
<212> TYPE: DNA
<213> ORGANISM: Artificial Sequence
<220> FEATURE:
<223> OTHER INFORMATION: Synthetic

<400> SEQUENCE: 41
gaaattgtat tgtcgcagtc tccaggcacc ctgtctttgt ctccagggga aagagccacc    60
ctctcctgca gggccagtca gagtgttagc agcagcttct tagcctggta ccaacaatat   120
cctggccagg ctcccaggct cctcatctat ggtgcatcca aaggccac tggcatccca     180 gacaggttcc gtggcagtgg gtctgggaca gacttcactc tcaccatcag cagactggag   240
cctgaagatt ttgcagtgta ttactgtcaa caatatggta gttcaccgct caccttcggc   300
ggagggacca aggtggagaa caaa                                          324

<210> SEQ ID NO 42
<211> LENGTH: 108
<212> TYPE: PRT
<213> ORGANISM: Artificial Sequence
<220> FEATURE:
<223> OTHER INFORMATION: Synthetic

<400> SEQUENCE: 42

Glu Ile Val Leu Ser Gln Ser Pro Gly Thr Leu Ser Leu Ser Pro Gly
 1               5                  10                  15
```

```
Glu Arg Ala Thr Leu Ser Cys Arg Ala Ser Gln Ser Val Ser Ser
            20                  25                  30

Phe Leu Ala Trp Tyr Gln Gln Tyr Pro Gly Gln Ala Pro Arg Leu Leu
        35                  40                  45

Ile Tyr Gly Ala Ser Arg Arg Ala Thr Gly Ile Pro Asp Arg Phe Arg
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gly Gly Thr Lys Val Glu Asn Lys
            100                 105

<210> SEQ ID NO 43
<211> LENGTH: 21
<212> TYPE: DNA
<213> ORGANISM: Artificial Sequence
<220> FEATURE:
<223> OTHER INFORMATION: Synthetic

<400> SEQUENCE: 43
cagagtgtta gcagcagctt c                                            21

<210> SEQ ID NO 44
<211> LENGTH: 7
<212> TYPE: PRT
<213> ORGANISM: Artificial Sequence
<220> FEATURE:
<223> OTHER INFORMATION: Synthetic

<400> SEQUENCE: 44

Gln Ser Val Ser Ser Ser Phe
1               5

<210> SEQ ID NO 45
<211> LENGTH: 9
<212> TYPE: DNA
<213> ORGANISM: Artificial Sequence
<220> FEATURE:
<223> OTHER INFORMATION: Synthetic

<400> SEQUENCE: 45 ggtgcatcc                                                           9

<210> SEQ ID NO 46
<211> LENGTH: 3
<212> TYPE: PRT
<213> ORGANISM: Artificial Sequence
<220> FEATURE:
<223> OTHER INFORMATION: Synthetic

<400> SEQUENCE: 46

Gly Ala Ser
1

<210> SEQ ID NO 47
<211> LENGTH: 27
<212> TYPE: DNA
<213> ORGANISM: Artificial Sequence
<220> FEATURE:
<223> OTHER INFORMATION: Synthetic

<400> SEQUENCE: 47
caacaatatg gtagttcacc gctcacc                                      27
```

<210> SEQ ID NO 48
<211> LENGTH: 9
<212> TYPE: PRT
<213> ORGANISM: Artificial Sequence
<220> FEATURE:
<223> OTHER INFORMATION: Synthetic

<400> SEQUENCE: 48

Gln Gln Tyr Gly Ser Ser Pro Leu Thr
 1               5

<210> SEQ ID NO 49
<211> LENGTH: 357
<212> TYPE: DNA
<213> ORGANISM: Artificial Sequence
<220> FEATURE:
<223> OTHER INFORMATION: Synthetic

<400> SEQUENCE: 49
caggtgcagc tacagcagtg gggcgcagga ctgttgaagc cttcggagac cctgtccctc      60
acctgcgctg tctatggtgg gtccttcact ggtttctact ggagctggat ccgccagccc     120
cccgggaagg ggctggagtg gattggggaa atcaatcatc gtggaaacac caactacaat     180
ccgtccctca agagtcgagt caccatgtca gtagacacgt ccaagaacca gttctccctg     240
aacatgatct ctgtgaccgc cgcggacacg gctatgtatt tctgtgcgag tccttttac      300 gattttggga gtggttccga ctactggggc cagggaaccc tggtcaccgt ctcctca       357

<210> SEQ ID NO 50
<211> LENGTH: 119
<212> TYPE: PRT
<213> ORGANISM: Artificial Sequence
<220> FEATURE:
<223> OTHER INFORMATION: Synthetic

<400> SEQUENCE: 50

Gln Val Gln Leu Gln Gln Trp Gly Ala Gly Leu Leu Lys Pro Ser Glu
 1               5                  10                  15

Thr Leu Ser Leu Thr Cys Ala Val Tyr Gly Gly Ser Phe Thr Gly Phe
            20                  25                  30

Tyr Trp Ser Trp Ile Arg Gln Pro Pro Gly Lys Gly Leu Glu Trp Ile
        35                  40                  45

Gly Glu Ile Asn His Arg Gly Asn Thr Asn Tyr Asn Pro Ser Leu Lys
    50                  55                  60

Ser Arg Val Thr Met Ser Val Asp Thr Ser Lys Asn Gln Phe Ser Leu
65                  70                  75                  80

Asn Met Ile Ser Val Thr Ala Ala Asp Thr Ala Met Tyr Phe Cys Ala
                85                  90                  95

Ser Pro Phe Tyr Asp Phe Trp Ser Gly Ser Asp Tyr Trp Gly Gln Gly
            100                 105                 110

Thr Leu Val Thr Val Ser Ser
        115

<210> SEQ ID NO 51
<211> LENGTH: 24
<212> TYPE: DNA
<213> ORGANISM: Artificial Sequence
<220> FEATURE:
<223> OTHER INFORMATION: Synthetic

<400> SEQUENCE: 51

```
ggtgggtcct tcactggttt ctac                                           24
```

<210> SEQ ID NO 52
<211> LENGTH: 8
<212> TYPE: PRT
<213> ORGANISM: Artificial Sequence
<220> FEATURE:
<223> OTHER INFORMATION: Synthetic

<400> SEQUENCE: 52

Gly Gly Ser Phe Thr Gly Phe Tyr
1               5

<210> SEQ ID NO 53
<211> LENGTH: 21
<212> TYPE: DNA
<213> ORGANISM: Artificial Sequence
<220> FEATURE:
<223> OTHER INFORMATION: Synthetic

<400> SEQUENCE: 53

```
atcaatcatc gtggaaacac c                                              21
```

<210> SEQ ID NO 54
<211> LENGTH: 7
<212> TYPE: PRT
<213> ORGANISM: Artificial Sequence
<220> FEATURE:
<223> OTHER INFORMATION: Synthetic

<400> SEQUENCE: 54

Ile Asn His Arg Gly Asn Thr
1               5

<210> SEQ ID NO 55
<211> LENGTH: 39
<212> TYPE: DNA
<213> ORGANISM: Artificial Sequence
<220> FEATURE:
<223> OTHER INFORMATION: Synthetic

<400> SEQUENCE: 55

```
gcgagtcctt tttacgattt ttggagtggt tccgactac                            39
```

<210> SEQ ID NO 56
<211> LENGTH: 13
<212> TYPE: PRT
<213> ORGANISM: Artificial Sequence
<220> FEATURE:
<223> OTHER INFORMATION: Synthetic

<400> SEQUENCE: 56

Ala Ser Pro Phe Tyr Asp Phe Trp Ser Gly Ser Asp Tyr
1               5                   10

<210> SEQ ID NO 57
<211> LENGTH: 336
<212> TYPE: DNA
<213> ORGANISM: Artificial Sequence
<220> FEATURE:
<223> OTHER INFORMATION: Synthetic

<400> SEQUENCE: 57

```
gacattatgt tgacccagac tccactcacc tcacctgtca cccttgggca gccggcctcc     60
atctcctgca agtctagtca aagcctcgta cacagtgatg gaaacaccta cttgagttgg    120
cttcagcaga ggccaggcca gcctccaaga ctcctatttt ataagatttc taaccggttc    180
```

```
tctggagtcc cagacagatt cagtggcagt ggggcaggga cagatttcac actgaaaatc    240
agcagggtgg aagctgagga tgtcggggtt tattactgca tgcaagctac acaatttcct    300
ctcactttcg gcggagggac caaggtagag atcaaa                              336
```

```
<210> SEQ ID NO 58
<211> LENGTH: 112
<212> TYPE: PRT
<213> ORGANISM: Artificial Sequence
<220> FEATURE:
<223> OTHER INFORMATION: Synthetic

<400> SEQUENCE: 58
```

```
Asp Ile Met Leu Thr Gln Thr Pro Leu Thr Ser Pro Val Thr Leu Gly
  1               5                  10                  15

Gln Pro Ala Ser Ile Ser Cys Lys Ser Ser Gln Ser Leu Val His Ser
             20                  25                  30

Asp Gly Asn Thr Tyr Leu Ser Trp Leu Gln Gln Arg Pro Gly Gln Pro
         35                  40                  45

Pro Arg Leu Leu Phe Tyr Lys Ile Ser Asn Arg Phe Ser Gly Val Pro
     50                  55                  60

Asp Arg Phe Ser Gly Ser Gly Ala Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Thr Gln Phe Pro Leu Thr Phe Gly Gly Gly Thr Lys Val Glu Ile Lys
            100                 105                 110
```

```
<210> SEQ ID NO 59
<211> LENGTH: 33
<212> TYPE: DNA
<213> ORGANISM: Artificial Sequence
<220> FEATURE:
<223> OTHER INFORMATION: Synthetic

<400> SEQUENCE: 59
caaagcctcg tacacagtga tggaaacacc tac                                  33
```

```
<210> SEQ ID NO 60
<211> LENGTH: 11
<212> TYPE: PRT
<213> ORGANISM: Artificial Sequence
<220> FEATURE:
<223> OTHER INFORMATION: Synthetic

<400> SEQUENCE: 60
```

```
Gln Ser Leu Val His Ser Asp Gly Asn Thr Tyr
  1               5                  10
```

```
<210> SEQ ID NO 61
<211> LENGTH: 9
<212> TYPE: DNA
<213> ORGANISM: Artificial Sequence
<220> FEATURE:
<223> OTHER INFORMATION: Synthetic

<400> SEQUENCE: 61 aagatttct                                                             9
```

```
<210> SEQ ID NO 62
<211> LENGTH: 3
<212> TYPE: PRT
<213> ORGANISM: Artificial Sequence
```

```
<220> FEATURE:
<223> OTHER INFORMATION: Synthetic

<400> SEQUENCE: 62

Lys Ile Ser
 1

<210> SEQ ID NO 63
<211> LENGTH: 27
<212> TYPE: DNA
<213> ORGANISM: Artificial Sequence
<220> FEATURE:
<223> OTHER INFORMATION: Synthetic

<400> SEQUENCE: 63
atgcaagcta cacaatttcc tctcact                                          27

<210> SEQ ID NO 64
<211> LENGTH: 9
<212> TYPE: PRT
<213> ORGANISM: Artificial Sequence
<220> FEATURE:
<223> OTHER INFORMATION: Synthetic

<400> SEQUENCE: 64

Met Gln Ala Thr Gln Phe Pro Leu Thr
 1               5

<210> SEQ ID NO 65
<211> LENGTH: 351
<212> TYPE: DNA
<213> ORGANISM: Artificial Sequence
<220> FEATURE:
<223> OTHER INFORMATION: Synthetic

<400> SEQUENCE: 65
caggtgcaac tacaacagtg gggcgcagga ctgttgaagc cctcggagac cctgtccctc      60
acctgcgctg tctctggtgg gtccttcagt gattacttct ggacctggat ccgccagccc     120
cccgggaagg ggctggagtg gattggggaa atcagtcata gtggaagaac caactacaac     180
ccgtccctca agagtcgagt caccatatca gttgacacgt ccatgagcca gttctccctg     240
aagatgacct ctgtgaccgc cgcggactcg gctgtatatt actgtgcgag agattatccc     300
aactgggttt ttgactactg ggccaggga accctggtca ccgtctcctc a              351

<210> SEQ ID NO 66
<211> LENGTH: 117
<212> TYPE: PRT
<213> ORGANISM: Artificial Sequence
<220> FEATURE:
<223> OTHER INFORMATION: Synthetic

<400> SEQUENCE: 66

Gln Val Gln Leu Gln Gln Trp Gly Ala Gly Leu Leu Lys Pro Ser Glu
 1               5                  10                  15

Thr Leu Ser Leu Thr Cys Ala Val Ser Gly Gly Ser Phe Ser Asp Tyr
             20                  25                  30

Phe Trp Thr Trp Ile Arg Gln Pro Pro Gly Lys Gly Leu Glu Trp Ile
         35                  40                  45

Gly Glu Ile Ser His Ser Gly Arg Thr Asn Tyr Asn Pro Ser Leu Lys
     50                  55                  60

Ser Arg Val Thr Ile Ser Val Asp Thr Ser Met Ser Gln Phe Ser Leu
 65                  70                  75                  80
```

```
Lys Met Thr Ser Val Thr Ala Ala Asp Ser Ala Val Tyr Tyr Cys Ala
                85                  90                  95

Arg Asp Tyr Pro Asn Trp Val Phe Asp Tyr Trp Gly Gln Gly Thr Leu
            100                 105                 110

Val Thr Val Ser Ser
        115

<210> SEQ ID NO 67
<211> LENGTH: 24
<212> TYPE: DNA
<213> ORGANISM: Artificial Sequence
<220> FEATURE:
<223> OTHER INFORMATION: Synthetic

<400> SEQUENCE: 67
ggtgggtcct tcagtgatta cttc                                           24

<210> SEQ ID NO 68
<211> LENGTH: 8
<212> TYPE: PRT
<213> ORGANISM: Artificial Sequence
<220> FEATURE:
<223> OTHER INFORMATION: Synthetic

<400> SEQUENCE: 68

Gly Gly Ser Phe Ser Asp Tyr Phe
 1               5

<210> SEQ ID NO 69
<211> LENGTH: 21
<212> TYPE: DNA
<213> ORGANISM: Artificial Sequence
<220> FEATURE:
<223> OTHER INFORMATION: Synthetic

<400> SEQUENCE: 69
atcagtcata gtggaagaac c                                              21

<210> SEQ ID NO 70
<211> LENGTH: 7
<212> TYPE: PRT
<213> ORGANISM: Artificial Sequence
<220> FEATURE:
<223> OTHER INFORMATION: Synthetic

<400> SEQUENCE: 70

Ile Ser His Ser Gly Arg Thr
 1               5

<210> SEQ ID NO 71
<211> LENGTH: 33
<212> TYPE: DNA
<213> ORGANISM: Artificial Sequence
<220> FEATURE:
<223> OTHER INFORMATION: Synthetic

<400> SEQUENCE: 71
gcgagagatt atcccaactg ggttttgac tac                                  33

<210> SEQ ID NO 72
<211> LENGTH: 11
<212> TYPE: PRT
<213> ORGANISM: Artificial Sequence
<220> FEATURE:
<223> OTHER INFORMATION: Synthetic

<400> SEQUENCE: 72
```

Ala Arg Asp Tyr Pro Asn Trp Val Phe Asp Tyr
 1               5                  10

<210> SEQ ID NO 73
<211> LENGTH: 324
<212> TYPE: DNA
<213> ORGANISM: Artificial Sequence
<220> FEATURE:
<223> OTHER INFORMATION: Synthetic

<400> SEQUENCE: 73
gaaattgagt tgacgcagtc tccaggcacc ctgtctttgt ctccagggga aggagccacc    60
ctctcctgca gggccagtca gagtgttttc aacagctact tagcgtggta ccagcagaaa   120
cctggccagg ctcccaggct cctcatctat ggtgcatcca ggagggccac tggcatccct   180
gacaggttca gtggcagtgg gtctgggaca gacttcactc tcaccatcag cagactggag   240
cctggagatt ttgcagtata tttctgtcag cagtatggta actcaccgct cactttcggc   300
ggagggacca aggtggagat caaa                                          324

<210> SEQ ID NO 74
<211> LENGTH: 108
<212> TYPE: PRT
<213> ORGANISM: Artificial Sequence
<220> FEATURE:
<223> OTHER INFORMATION: Synthetic

<400> SEQUENCE: 74

Glu Ile Glu Leu Thr Gln Ser Pro Gly Thr Leu Ser Leu Ser Pro Gly
 1               5                  10                  15

Glu Gly Ala Thr Leu Ser Cys Arg Ala Ser Gln Ser Val Phe Asn Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Arg Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Gly Asp Phe Ala Val Tyr Phe Cys Gln Gln Tyr Gly Asn Ser Pro
                85                  90                  95

Leu Thr Phe Gly Gly Gly Thr Lys Val Glu Ile Lys
            100                 105

<210> SEQ ID NO 75
<211> LENGTH: 21
<212> TYPE: DNA
<213> ORGANISM: Artificial Sequence
<220> FEATURE:
<223> OTHER INFORMATION: Synthetic

<400> SEQUENCE: 75
cagagtgttt tcaacagcta c                                              21

<210> SEQ ID NO 76
<211> LENGTH: 7
<212> TYPE: PRT
<213> ORGANISM: Artificial Sequence
<220> FEATURE:
<223> OTHER INFORMATION: Synthetic

<400> SEQUENCE: 76

Gln Ser Val Phe Asn Ser Tyr

<210> SEQ ID NO 77
<211> LENGTH: 9
<212> TYPE: DNA
<213> ORGANISM: Artificial Sequence
<220> FEATURE:
<223> OTHER INFORMATION: Synthetic

<400> SEQUENCE: 77 ggtgcatcc                                                                9

<210> SEQ ID NO 78
<211> LENGTH: 3
<212> TYPE: PRT
<213> ORGANISM: Artificial Sequence
<220> FEATURE:
<223> OTHER INFORMATION: Synthetic

<400> SEQUENCE: 78

Gly Ala Ser
 1

<210> SEQ ID NO 79
<211> LENGTH: 27
<212> TYPE: DNA
<213> ORGANISM: Artificial Sequence
<220> FEATURE:
<223> OTHER INFORMATION: Synthetic

<400> SEQUENCE: 79
cagcagtatg gtaactcacc gctcact                                           27

<210> SEQ ID NO 80
<211> LENGTH: 9
<212> TYPE: PRT
<213> ORGANISM: Artificial Sequence
<220> FEATURE:
<223> OTHER INFORMATION: Synthetic

<400> SEQUENCE: 80

Gln Gln Tyr Gly Asn Ser Pro Leu Thr
 1               5

<210> SEQ ID NO 81
<211> LENGTH: 366
<212> TYPE: DNA
<213> ORGANISM: Artificial Sequence
<220> FEATURE:
<223> OTHER INFORMATION: Synthetic

<400> SEQUENCE: 81
cggttgcagc tggtggagtc tgggggaggc ttggtcaagc ctggagggtc cctgaaactc        60
tcctgtgcag cctctggatt caccatcagt gactactaca tgagctggat ccgccaggct       120
ccagggaagg gctggagtg gtttcgtac attggtggta gtggtagtac catatattac         180
gcagactctg tgaagggccg attcaccatc tccaggaca cgccaagaa ctcactgtat         240 ctgcaaatga acagcctgag agccgaggac acggccgtat attactgtgc gagagaggac       300
gctgactcct actactacta cggtatggac gtctggggcc aagggaccac ggtcaccgtc       360
tcctca                                                                 366

<210> SEQ ID NO 82
<211> LENGTH: 122
<212> TYPE: PRT

<213> ORGANISM: Artificial Sequence
<220> FEATURE:
<223> OTHER INFORMATION: Synthetic

<400> SEQUENCE: 82

```
Arg Leu Gln Leu Val Glu Ser Gly Gly Gly Leu Val Lys Pro Gly Gly
 1               5                  10                  15
Ser Leu Lys Leu Ser Cys Ala Ala Ser Gly Phe Thr Ile Ser Asp Tyr
            20                  25                  30
Tyr Met Ser Trp Ile Arg Gln Ala Pro Gly Lys Gly Leu Glu Trp Val
        35                  40                  45
Ser Tyr Ile Gly Gly Ser Gly Ser Thr Ile Tyr Tyr Ala Asp Ser Val
    50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Ala Arg Glu Asp Ala Asp Ser Tyr Tyr Tyr Gly Met Asp Val Trp
            100                 105                 110
Gly Gln Gly Thr Thr Val Thr Val Ser Ser
        115                 120
```

<210> SEQ ID NO 83
<211> LENGTH: 24
<212> TYPE: DNA
<213> ORGANISM: Artificial Sequence
<220> FEATURE:
<223> OTHER INFORMATION: Synthetic

<400> SEQUENCE: 83
ggattcacca tcagtgacta ctac                                          24

<210> SEQ ID NO 84
<211> LENGTH: 8
<212> TYPE: PRT
<213> ORGANISM: Artificial Sequence
<220> FEATURE:
<223> OTHER INFORMATION: Synthetic

<400> SEQUENCE: 84

```
Gly Phe Thr Ile Ser Asp Tyr Tyr
 1               5
```

<210> SEQ ID NO 85
<211> LENGTH: 24
<212> TYPE: DNA
<213> ORGANISM: Artificial Sequence
<220> FEATURE:
<223> OTHER INFORMATION: Synthetic

<400> SEQUENCE: 85
attggtggta gtggtagtac cata                                          24

<210> SEQ ID NO 86
<211> LENGTH: 8
<212> TYPE: PRT
<213> ORGANISM: Artificial Sequence
<220> FEATURE:
<223> OTHER INFORMATION: Synthetic

<400> SEQUENCE: 86

```
Ile Gly Gly Ser Gly Ser Thr Ile
 1               5
```

<210> SEQ ID NO 87
<211> LENGTH: 45
<212> TYPE: DNA
<213> ORGANISM: Artificial Sequence
<220> FEATURE:
<223> OTHER INFORMATION: Synthetic

<400> SEQUENCE: 87
gcgagagagg acgctgactc ctactactac tacggtatgg acgtc            45

<210> SEQ ID NO 88
<211> LENGTH: 15
<212> TYPE: PRT
<213> ORGANISM: Artificial Sequence
<220> FEATURE:
<223> OTHER INFORMATION: Synthetic

<400> SEQUENCE: 88

Ala Arg Glu Asp Ala Asp Ser Tyr Tyr Tyr Tyr Gly Met Asp Val
 1               5                  10                  15

<210> SEQ ID NO 89
<211> LENGTH: 339
<212> TYPE: DNA
<213> ORGANISM: Artificial Sequence
<220> FEATURE:
<223> OTHER INFORMATION: Synthetic

<400> SEQUENCE: 89
gatattgtga tgacccagtc tccagactcc ctggctgtgt ctctgggcga gagggccacc     60
atcaactgca gtccagcca gagtgtttta tacagctcca acaataagaa ccacttatct    120
tggtatcagc agaaaccagg acagcctcct aagctgctca tttactgggc atctacccgg    180
gaatccgggg tccctgaccg attcagtggc agcgggtctg ggacagattt cactctcacc    240
atcagcagcc tgcaggctga agatgtggca gtttattact gtcaacaata ttatagtact    300
cctcggacgt tcggccaagg gaccaaggtg gaaatcaaa                           339

<210> SEQ ID NO 90
<211> LENGTH: 113
<212> TYPE: PRT
<213> ORGANISM: Artificial Sequence
<220> FEATURE:
<223> OTHER INFORMATION: Synthetic

<400> SEQUENCE: 90

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Val Leu Tyr Ser
            20                  25                  30

Ser Asn Asn Lys Asn His Leu Ser Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Arg Thr Phe Gly Gln Gly Thr Lys Val Glu Ile
            100                 105                 110

Lys

<210> SEQ ID NO 91
<211> LENGTH: 36
<212> TYPE: DNA
<213> ORGANISM: Artificial Sequence
<220> FEATURE:
<223> OTHER INFORMATION: Synthetic

<400> SEQUENCE: 91
cagagtgttt tatacagctc caacaataag aaccac                                    36

<210> SEQ ID NO 92
<211> LENGTH: 12
<212> TYPE: PRT
<213> ORGANISM: Artificial Sequence
<220> FEATURE:
<223> OTHER INFORMATION: Synthetic

<400> SEQUENCE: 92

Gln Ser Val Leu Tyr Ser Ser Asn Asn Lys Asn His
 1               5                  10

<210> SEQ ID NO 93
<211> LENGTH: 9
<212> TYPE: DNA
<213> ORGANISM: Artificial Sequence
<220> FEATURE:
<223> OTHER INFORMATION: Synthetic

<400> SEQUENCE: 93 tgggcatct                                                                   9

<210> SEQ ID NO 94
<211> LENGTH: 3
<212> TYPE: PRT
<213> ORGANISM: Artificial Sequence
<220> FEATURE:
<223> OTHER INFORMATION: Synthetic

<400> SEQUENCE: 94

Trp Ala Ser
 1

<210> SEQ ID NO 95
<211> LENGTH: 27
<212> TYPE: DNA
<213> ORGANISM: Artificial Sequence
<220> FEATURE:
<223> OTHER INFORMATION: Synthetic

<400> SEQUENCE: 95
caacaatatt atagtactcc tcggacg                                              27

<210> SEQ ID NO 96
<211> LENGTH: 9
<212> TYPE: PRT
<213> ORGANISM: Artificial Sequence
<220> FEATURE:
<223> OTHER INFORMATION: Synthetic

<400> SEQUENCE: 96

Gln Gln Tyr Tyr Ser Thr Pro Arg Thr
 1               5

<210> SEQ ID NO 97
<211> LENGTH: 366
<212> TYPE: DNA
<213> ORGANISM: Artificial Sequence

```
<220> FEATURE:
<223> OTHER INFORMATION: Synthetic

<400> SEQUENCE: 97
gaagtgcaac tggtggagtc tgggggaggc ttggtacagc ctggcaggtc cctgagactc      60
tcctgtgtag cctctggatt cacctttcaa gattatgcca tgcactgggt ccggcaagct     120
ccaggaaagg gcctggagtg ggtctcaggt attaattgga ttagtgatga catgggctat     180
gcggactctg tgatgggccg attcaccatc tccagagaca acgccaagaa ctccctgtat     240
ctgcaaatgg acagtctgag agctgaggac acggccttgt attactgtgc aaaagataag     300
ggattacgat ttttggacta tgttatggac gtctggggcc aagggaccac ggtcaccgtc     360
tcctca                                                                366

<210> SEQ ID NO 98
<211> LENGTH: 122
<212> TYPE: PRT
<213> ORGANISM: Artificial Sequence
<220> FEATURE:
<223> OTHER INFORMATION: Synthetic

<400> SEQUENCE: 98

Glu Val Gln Leu Val Glu Ser Gly Gly Gly Leu Val Gln Pro Gly Arg
1               5                   10                  15

Ser Leu Arg Leu Ser Cys Val Ala Ser Gly Phe Thr Phe Gln Asp Tyr
            20                  25                  30

Ala Met His Trp Val Arg Gln Ala Pro Gly Lys Gly Leu Glu Trp Val
        35                  40                  45

Ser Gly Ile Asn Trp Ile Ser Asp Asp Met Gly Tyr Ala Asp Ser Val
    50                  55                  60

Met Gly Arg Phe Thr Ile Ser Arg Asp Asn Ala Lys Asn Ser Leu Tyr
65                  70                  75                  80

Leu Gln Met Asp Ser Leu Arg Ala Glu Asp Thr Ala Leu Tyr Tyr Cys
                85                  90                  95

Ala Lys Asp Lys Gly Leu Arg Phe Leu Asp Tyr Val Met Asp Val Trp
            100                 105                 110

Gly Gln Gly Thr Thr Val Thr Val Ser Ser
        115                 120

<210> SEQ ID NO 99
<211> LENGTH: 24
<212> TYPE: DNA
<213> ORGANISM: Artificial Sequence
<220> FEATURE:
<223> OTHER INFORMATION: Synthetic

<400> SEQUENCE: 99
ggattcacct ttcaagatta tgcc                                             24

<210> SEQ ID NO 100
<211> LENGTH: 8
<212> TYPE: PRT
<213> ORGANISM: Artificial Sequence
<220> FEATURE:
<223> OTHER INFORMATION: Synthetic

<400> SEQUENCE: 100

Gly Phe Thr Phe Gln Asp Tyr Ala
1               5

<210> SEQ ID NO 101
```

```
<211> LENGTH: 24
<212> TYPE: DNA
<213> ORGANISM: Artificial Sequence
<220> FEATURE:
<223> OTHER INFORMATION: Synthetic

<400> SEQUENCE: 101
attaattgga ttagtgatga catg                                              24

<210> SEQ ID NO 102
<211> LENGTH: 8
<212> TYPE: PRT
<213> ORGANISM: Artificial Sequence
<220> FEATURE:
<223> OTHER INFORMATION: Synthetic

<400> SEQUENCE: 102

Ile Asn Trp Ile Ser Asp Asp Met
 1               5

<210> SEQ ID NO 103
<211> LENGTH: 45
<212> TYPE: DNA
<213> ORGANISM: Artificial Sequence
<220> FEATURE:
<223> OTHER INFORMATION: Synthetic

<400> SEQUENCE: 103
gcaaaagata agggattacg atttttggac tatgttatgg acgtc                       45

<210> SEQ ID NO 104
<211> LENGTH: 15
<212> TYPE: PRT
<213> ORGANISM: Artificial Sequence
<220> FEATURE:
<223> OTHER INFORMATION: Synthetic

<400> SEQUENCE: 104

Ala Lys Asp Lys Gly Leu Arg Phe Leu Asp Tyr Val Met Asp Val
 1               5                  10                  15

<210> SEQ ID NO 105
<211> LENGTH: 339
<212> TYPE: DNA
<213> ORGANISM: Artificial Sequence
<220> FEATURE:
<223> OTHER INFORMATION: Synthetic

<400> SEQUENCE: 105
gacatccagt tgacccagtc tcctctctcc ctgcccgtca cccctggaga gccggcctcc        60
atctcctgca ggtctactca gagcctcctg cataggaatg ccacaactat tttgcattgg       120
tacctacata agccagggca gtctccacaa ctcctgattc atctgggttc taatcgggcc       180
tccggggtcc ctgacaggtt cagtggcagt ggatcaggca cagattttac actgaaaatc       240
agcagagtgg aggctgagga tgttggggtc tattactgca tgcaagctct acagactccg       300
tacacttttg gccaggggac caaggtggag atcaaacga                              339

<210> SEQ ID NO 106
<211> LENGTH: 113
<212> TYPE: PRT
<213> ORGANISM: Artificial Sequence
<220> FEATURE:
<223> OTHER INFORMATION: Synthetic

<400> SEQUENCE: 106
```

-continued

Asp Ile Gln Leu Thr Gln Ser Pro Leu Ser Leu Pro Val Thr Pro Gly
1               5                   10                  15

Glu Pro Ala Ser Ile Ser Cys Arg Ser Thr Gln Ser Leu Leu His Arg
            20                  25                  30

Asn Gly His Asn Tyr Leu His Trp Tyr Leu His Lys Pro Gly Gln Ser
        35                  40                  45

Pro Gln Leu Leu Ile His Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Tyr Thr Phe Gly Gln Gly Thr Lys Val Glu Ile Lys
            100                 105                 110

Arg

<210> SEQ ID NO 107
<211> LENGTH: 33
<212> TYPE: DNA
<213> ORGANISM: Artificial Sequence
<220> FEATURE:
<223> OTHER INFORMATION: Synthetic

<400> SEQUENCE: 107
cagagcctcc tgcataggaa tggccacaac tat                              33

<210> SEQ ID NO 108
<211> LENGTH: 11
<212> TYPE: PRT
<213> ORGANISM: Artificial Sequence
<220> FEATURE:
<223> OTHER INFORMATION: Synthetic

<400> SEQUENCE: 108

Gln Ser Leu Leu His Arg Asn Gly His Asn Tyr
1               5                   10

<210> SEQ ID NO 109
<211> LENGTH: 9
<212> TYPE: DNA
<213> ORGANISM: Artificial Sequence
<220> FEATURE:
<223> OTHER INFORMATION: Synthetic

<400> SEQUENCE: 109 ctgggttct                                                          9

<210> SEQ ID NO 110
<211> LENGTH: 3
<212> TYPE: PRT
<213> ORGANISM: Artificial Sequence
<220> FEATURE:
<223> OTHER INFORMATION: Synthetic

<400> SEQUENCE: 110

Leu Gly Ser
1

<210> SEQ ID NO 111
<211> LENGTH: 27
<212> TYPE: DNA
<213> ORGANISM: Artificial Sequence
<220> FEATURE:
<223> OTHER INFORMATION: Synthetic

```
<400> SEQUENCE: 111
atgcaagctc tacagactcc gtacact                                            27

<210> SEQ ID NO 112
<211> LENGTH: 9
<212> TYPE: PRT
<213> ORGANISM: Artificial Sequence
<220> FEATURE:
<223> OTHER INFORMATION: Synthetic

<400> SEQUENCE: 112

Met Gln Ala Leu Gln Thr Pro Tyr Thr
 1               5

<210> SEQ ID NO 113
<211> LENGTH: 363
<212> TYPE: DNA
<213> ORGANISM: Artificial Sequence
<220> FEATURE:
<223> OTHER INFORMATION: Synthetic

<400> SEQUENCE: 113
gaggtgcagc tggtggagtc tgggggaggc ttggtacagc ctggcaggtc cctgagactc        60
tcctgtgtag cctctggatt cacctttcaa gattatgcca tgcactgggt ccggcaagct       120
ccaggaaagg gcctggagtg ggtctcaggt attaattgga ttagtgatga catgggctat       180
gcggactctg tgatgggccg attcaccatc tccagagaca cgccaagaa ctccctgtat        240 ctgcaaatgg acagtctgag agctgaggac acggccttgt attactgtgc aaaagataag      300
ggattacgat ttttggacta tgttatggac gtctggggcc aagggaccac ggtcaccgtc      360
tcc                                                                    363

<210> SEQ ID NO 114
<211> LENGTH: 121
<212> TYPE: PRT
<213> ORGANISM: Artificial Sequence
<220> FEATURE:
<223> OTHER INFORMATION: Synthetic

<400> SEQUENCE: 114

Glu Val Gln Leu Val Glu Ser Gly Gly Gly Leu Val Gln Pro Gly Arg
 1               5                  10                  15

Ser Leu Arg Leu Ser Cys Val Ala Ser Gly Phe Thr Phe Gln Asp Tyr
            20                  25                  30

Ala Met His Trp Val Arg Gln Ala Pro Gly Lys Gly Leu Glu Trp Val
        35                  40                  45

Ser Gly Ile Asn Trp Ile Ser Asp Asp Met Gly Tyr Ala Asp Ser Val
    50                  55                  60

Met Gly Arg Phe Thr Ile Ser Arg Asp Asn Ala Lys Asn Ser Leu Tyr
65                  70                  75                  80

Leu Gln Met Asp Ser Leu Arg Ala Glu Asp Thr Ala Leu Tyr Tyr Cys
                85                  90                  95

Ala Lys Asp Lys Gly Leu Arg Phe Leu Asp Tyr Val Met Asp Val Trp
            100                 105                 110

Gly Gln Gly Thr Thr Val Thr Val Ser
        115                 120

<210> SEQ ID NO 115
<211> LENGTH: 336
<212> TYPE: DNA
```

<213> ORGANISM: Artificial Sequence
<220> FEATURE:
<223> OTHER INFORMATION: Synthetic

<400> SEQUENCE: 115

```
gacatcgtga tgacccagtc tcctctctcc ctgcccgtca cccctggaga gccggcctcc      60
atctcctgca ggtctactca gagcctcctg cataggaatg ccacaactat tttgcattgg     120
tacctacata agccagggca gtctccacaa ctcctgattc atctgggttc taatcgggcc     180
tccggggtcc ctgacaggtt cagtggcagt ggatcaggca cagatttta actgaaaatc      240
agcagagtgg aggctgagga tgttggggtc tattactgca tgcaagctct acagactccg     300
tacactttg gccaggggac caagctggag atcaaa                                336
```

<210> SEQ ID NO 116
<211> LENGTH: 112
<212> TYPE: PRT
<213> ORGANISM: Artificial Sequence
<220> FEATURE:
<223> OTHER INFORMATION: Synthetic

<400> SEQUENCE: 116

```
Asp Ile Val Met Thr Gln Ser Pro Leu Ser Leu Pro Val Thr Pro Gly
  1               5                  10                  15
Glu Pro Ala Ser Ile Ser Cys Arg Ser Thr Gln Ser Leu Leu His Arg
             20                  25                  30
Asn Gly His Asn Tyr Leu His Trp Tyr Leu His Lys Pro Gly Gln Ser
         35                  40                  45
Pro Gln Leu Leu Ile His Leu Gly Ser Asn Arg Ala Ser Gly Val Pro
     50                  55                  60
Asp Arg Phe Ser Gly Ser Gly Ser Gly Thr Asp Phe Thr Leu Lys Ile
 65                  70                  75                  80
Ser Arg Val Glu Ala Glu Asp Val Gly Val Tyr Tyr Cys Met Gln Ala
                 85                  90                  95
Leu Gln Thr Pro Tyr Thr Phe Gly Gln Gly Thr Lys Leu Glu Ile Lys
            100                 105                 110
```

<210> SEQ ID NO 117
<211> LENGTH: 354
<212> TYPE: DNA
<213> ORGANISM: Artificial Sequence
<220> FEATURE:
<223> OTHER INFORMATION: Synthetic

<400> SEQUENCE: 117

```
caggtgcagc tggtggagtc tggggctgag gtgaagaagc ctggggcctc agtgaaggtc      60
tcctgcaagg cttctggata caccttcacc ggctactata tgcactgggt gcgacaggcc     120
cctggacaag gcttgagtg gatgggatgg atcaaaccta aagtggtgg cacaaactat       180
gtacagaagt tcagggcag ggtcaccatg accaggaca cgtccatcaa cacagcctac       240
atggaactaa caatctgaa atctgacgac acggccgttt attactgtgc gactggaggg      300
agtcaagatg cttctgattt ctggggccaa gggacaatgg tcaccgtctc ttca           354
```

<210> SEQ ID NO 118
<211> LENGTH: 118
<212> TYPE: PRT
<213> ORGANISM: Artificial Sequence
<220> FEATURE:
<223> OTHER INFORMATION: Synthetic

<400> SEQUENCE: 118

```
Gln Val Gln Leu Val Glu Ser Gly Ala Glu Val Lys Lys Pro Gly Ala
  1               5                  10                  15

Ser Val Lys Val Ser Cys Lys Ala Ser Gly Tyr Thr Phe Thr Gly Tyr
             20                  25                  30

Tyr Met His Trp Val Arg Gln Ala Pro Gly Gln Gly Leu Glu Trp Met
         35                  40                  45

Gly Trp Ile Lys Pro Lys Ser Gly Gly Thr Asn Tyr Val Gln Lys Phe
 50                  55                  60

Gln Gly Arg Val Thr Met Thr Arg Asp Thr Ser Ile Asn Thr Ala Tyr
 65                  70                  75                  80

Met Glu Leu Asn Asn Leu Lys Ser Asp Asp Thr Ala Val Tyr Tyr Cys
                 85                  90                  95

Ala Thr Gly Gly Ser Gln Asp Ala Ser Asp Phe Trp Gly Gln Gly Thr
            100                 105                 110

Met Val Thr Val Ser Ser
            115
```

```
<210> SEQ ID NO 119
<211> LENGTH: 24
<212> TYPE: DNA
<213> ORGANISM: Artificial Sequence
<220> FEATURE:
<223> OTHER INFORMATION: Synthetic

<400> SEQUENCE: 119
ggatacacct tcaccggcta ctat                                          24
```

```
<210> SEQ ID NO 120
<211> LENGTH: 8
<212> TYPE: PRT
<213> ORGANISM: Artificial Sequence
<220> FEATURE:
<223> OTHER INFORMATION: Synthetic

<400> SEQUENCE: 120

Gly Tyr Thr Phe Thr Gly Tyr Tyr
 1               5
```

```
<210> SEQ ID NO 121
<211> LENGTH: 24
<212> TYPE: DNA
<213> ORGANISM: Artificial Sequence
<220> FEATURE:
<223> OTHER INFORMATION: Synthetic

<400> SEQUENCE: 121
atcaaaccta aaagtggtgg caca                                          24
```

```
<210> SEQ ID NO 122
<211> LENGTH: 8
<212> TYPE: PRT
<213> ORGANISM: Artificial Sequence
<220> FEATURE:
<223> OTHER INFORMATION: Synthetic

<400> SEQUENCE: 122

Ile Lys Pro Lys Ser Gly Gly Thr
 1               5
```

```
<210> SEQ ID NO 123
<211> LENGTH: 33
<212> TYPE: DNA
<213> ORGANISM: Artificial Sequence
```

<220> FEATURE:
<223> OTHER INFORMATION: Synthetic

<400> SEQUENCE: 123
gcgactggag ggagtcaaga tgcttctgat ttc                          33

<210> SEQ ID NO 124
<211> LENGTH: 11
<212> TYPE: PRT
<213> ORGANISM: Artificial Sequence
<220> FEATURE:
<223> OTHER INFORMATION: Synthetic

<400> SEQUENCE: 124

Ala Thr Gly Gly Ser Gln Asp Ala Ser Asp Phe
 1               5                  10

<210> SEQ ID NO 125
<211> LENGTH: 324
<212> TYPE: DNA
<213> ORGANISM: Artificial Sequence
<220> FEATURE:
<223> OTHER INFORMATION: Synthetic

<400> SEQUENCE: 125
gacatccagt tgacccagtc tccatcttcc gtgtctgcat ctgtaggagg cagagtcacc      60
atcacttgtc gggcgagtca ggatattagc atctggttag cctggtatca acagaaacca    120
gggaaagccc ctaacctcct gatctatgct gcatccagtt tacaaagtgg ggtcccatca    180
aggttcagcg gcagtggatc tgggacagat ttcactctca ccatcagcag cctgcagcct    240
gaagattttg caacttacta ttgtcaacag gctgacagtt tcccgctcac tttcggcggt    300
gggaccaagc tggagatcaa acga                                          324

<210> SEQ ID NO 126
<211> LENGTH: 108
<212> TYPE: PRT
<213> ORGANISM: Artificial Sequence
<220> FEATURE:
<223> OTHER INFORMATION: Synthetic

<400> SEQUENCE: 126

Asp Ile Gln Leu Thr Gln Ser Pro Ser Ser Val Ser Ala Ser Val Gly
 1               5                  10                  15

Gly Arg Val Thr Ile Thr Cys Arg Ala Ser Gln Asp Ile Ser Ile Trp
             20                  25                  30

Leu Ala Trp Tyr Gln Gln Lys Pro Gly Lys Ala Pro Asn Leu Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Asp Ser Phe Pro Leu
                 85                  90                  95

Thr Phe Gly Gly Gly Thr Lys Leu Glu Ile Lys Arg
            100                 105

<210> SEQ ID NO 127
<211> LENGTH: 18
<212> TYPE: DNA
<213> ORGANISM: Artificial Sequence
<220> FEATURE:
<223> OTHER INFORMATION: Synthetic

<400> SEQUENCE: 127
caggatatta gcatctgg					18

<210> SEQ ID NO 128
<211> LENGTH: 6
<212> TYPE: PRT
<213> ORGANISM: Artificial Sequence
<220> FEATURE:
<223> OTHER INFORMATION: Synthetic

<400> SEQUENCE: 128

Gln Asp Ile Ser Ile Trp
 1               5

<210> SEQ ID NO 129
<211> LENGTH: 9
<212> TYPE: DNA
<213> ORGANISM: Artificial Sequence
<220> FEATURE:
<223> OTHER INFORMATION: Synthetic

<400> SEQUENCE: 129 gctgcatcc					9

<210> SEQ ID NO 130
<211> LENGTH: 3
<212> TYPE: PRT
<213> ORGANISM: Artificial Sequence
<220> FEATURE:
<223> OTHER INFORMATION: Synthetic

<400> SEQUENCE: 130

Ala Ala Ser
 1

<210> SEQ ID NO 131
<211> LENGTH: 27
<212> TYPE: DNA
<213> ORGANISM: Artificial Sequence
<220> FEATURE:
<223> OTHER INFORMATION: Synthetic

<400> SEQUENCE: 131
caacaggctg acagtttccc gctcact					27

<210> SEQ ID NO 132
<211> LENGTH: 9
<212> TYPE: PRT
<213> ORGANISM: Artificial Sequence
<220> FEATURE:
<223> OTHER INFORMATION: Synthetic

<400> SEQUENCE: 132

Gln Gln Ala Asp Ser Phe Pro Leu Thr
 1               5

<210> SEQ ID NO 133
<211> LENGTH: 354
<212> TYPE: DNA
<213> ORGANISM: Artificial Sequence
<220> FEATURE:
<223> OTHER INFORMATION: Synthetic

<400> SEQUENCE: 133
caggtgcagc tggtgcagtc tggggctgag gtgaagaagc ctggggcctc agtgaaggtc					60

```
tcctgcaagg cttctggata caccttcacc ggctactata tgcactgggt gcgacaggcc      120
cctggacaag ggcttgagtg gatgggatgg atcaaaccta aaagtggtgg cacaaactat      180
gtacagaagt ttcagggcag ggtcaccatg accagggaca cgtccatcaa cacagcctac      240
atggaactaa acaatctgaa atctgacgac acggccgttt attactgtgc gactggaggg      300
agtcaagatg cttctgattt ctggggccaa gggacaatgg tcaccgtctc ttca            354
```

```
<210> SEQ ID NO 134
<211> LENGTH: 118
<212> TYPE: PRT
<213> ORGANISM: Artificial Sequence
<220> FEATURE:
<223> OTHER INFORMATION: Synthetic

<400> SEQUENCE: 134
```

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Lys Pro Lys Ser Gly Gly Thr Asn Tyr Val Gln Lys Phe
    50                  55                  60

Gln Gly Arg Val Thr Met Thr Arg Asp Thr Ser Ile Asn Thr Ala Tyr
65                  70                  75                  80

Met Glu Leu Asn Asn Leu Lys Ser Asp Asp Thr Ala Val Tyr Tyr Cys
                85                  90                  95

Ala Thr Gly Gly Ser Gln Asp Ala Ser Asp Phe Trp Gly Gln Gly Thr
            100                 105                 110

Met Val Thr Val Ser Ser
        115
```

```
<210> SEQ ID NO 135
<211> LENGTH: 321
<212> TYPE: DNA
<213> ORGANISM: Artificial Sequence
<220> FEATURE:
<223> OTHER INFORMATION: Synthetic

<400> SEQUENCE: 135
```

```
gacatccaga tgacccagtc tccatcttcc gtgtctgcat ctgtaggagg cagagtcacc      60
atcacttgtc gggcgagtca ggatattagc atctggttag cctggtatca acagaaacca     120
gggaaagccc ctaacctcct gatctatgct gcatccagtt tacaaagtgg ggtcccatca     180
aggttcagcg gcagtggatc tgggacagat ttcactctca ccatcagcag cctgcagcct     240
gaagattttg caacttacta ttgtcaacag gctgacagtt tcccgctcac tttcggcggt     300
gggaccaagg tggagatcaa a                                               321
```

```
<210> SEQ ID NO 136
<211> LENGTH: 107
<212> TYPE: PRT
<213> ORGANISM: Artificial Sequence
<220> FEATURE:
<223> OTHER INFORMATION: Synthetic

<400> SEQUENCE: 136
```

```
Asp Ile Gln Met Thr Gln Ser Pro Ser Ser Val Ser Ala Ser Val Gly
 1               5                  10                  15

Gly Arg Val Thr Ile Thr Cys Arg Ala Ser Gln Asp Ile Ser Ile Trp
```

```
                    20                  25                  30
Leu Ala Trp Tyr Gln Gln Lys Pro Gly Lys Ala Pro Asn Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asp Ser Phe Pro Leu
                85                  90                  95

Thr Phe Gly Gly Gly Thr Lys Val Glu Ile Lys
                100                 105
```

<210> SEQ ID NO 137
<211> LENGTH: 378
<212> TYPE: DNA
<213> ORGANISM: Artificial Sequence
<220> FEATURE:
<223> OTHER INFORMATION: Synthetic

<400> SEQUENCE: 137

```
caggtgcagc tggtggagtc tgggggagcc ttggtaaagc ctggggggtc ccttagactc      60
tcctgtgcag tctctggatt cactttcatt aatgactgga tgaactgggt ccgccaggct     120
ccagggaagg ggctggaatg ggttggccgt attaaaagca caactgatgg tgggacaaca     180
gacgacgctg cacccgtgaa aggcagattc accatctcaa gagatgactc aaaaaacacg     240
ctatatctgc aaatgaatag cctgaaaacc gaggacacag ccgtgtatta ctgtaccaga     300
gataggaacc gacagagaaa ttacttctat gacggtatgg acgtctgggg ccaagggacc     360
acggtcaccg tctcctca                                                   378
```

<210> SEQ ID NO 138
<211> LENGTH: 126
<212> TYPE: PRT
<213> ORGANISM: Artificial Sequence
<220> FEATURE:
<223> OTHER INFORMATION: Synthetic

<400> SEQUENCE: 138

```
Gln Val Gln Leu Val Glu Ser Gly Gly Ala Leu Val Lys Pro Gly Gly
1               5                   10                  15

Ser Leu Arg Leu Ser Cys Ala Val Ser Gly Phe Thr Phe Ile Asn Asp
            20                  25                  30

Trp Met Asn Trp Val Arg Gln Ala Pro Gly Lys Gly Leu Glu Trp Val
        35                  40                  45

Gly Arg Ile Lys Ser Thr Thr Asp Gly Gly Thr Thr Asp Asp Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Arg Asp Arg Asn Arg Gln Arg Asn Tyr Phe Tyr Asp Gly
                100                 105                 110

Met Asp Val Trp Gly Gln Gly Thr Thr Val Thr Val Ser Ser
            115                 120                 125
```

<210> SEQ ID NO 139
<211> LENGTH: 24
<212> TYPE: DNA
<213> ORGANISM: Artificial Sequence

```
<220> FEATURE:
<223> OTHER INFORMATION: Synthetic

<400> SEQUENCE: 139
ggattcactt tcattaatga ctgg                                          24

<210> SEQ ID NO 140
<211> LENGTH: 8
<212> TYPE: PRT
<213> ORGANISM: Artificial Sequence
<220> FEATURE:
<223> OTHER INFORMATION: Synthetic

<400> SEQUENCE: 140

Gly Phe Thr Phe Ile Asn Asp Trp
1               5

<210> SEQ ID NO 141
<211> LENGTH: 30
<212> TYPE: DNA
<213> ORGANISM: Artificial Sequence
<220> FEATURE:
<223> OTHER INFORMATION: Synthetic

<400> SEQUENCE: 141
attaaaagca caactgatgg tgggacaaca                                    30

<210> SEQ ID NO 142
<211> LENGTH: 10
<212> TYPE: PRT
<213> ORGANISM: Artificial Sequence
<220> FEATURE:
<223> OTHER INFORMATION: Synthetic

<400> SEQUENCE: 142

Ile Lys Ser Thr Thr Asp Gly Gly Thr Thr
1               5                   10

<210> SEQ ID NO 143
<211> LENGTH: 51
<212> TYPE: DNA
<213> ORGANISM: Artificial Sequence
<220> FEATURE:
<223> OTHER INFORMATION: Synthetic

<400> SEQUENCE: 143
accagagata ggaaccgaca gagaaattac ttctatgacg gtatggacgt c            51

<210> SEQ ID NO 144
<211> LENGTH: 17
<212> TYPE: PRT
<213> ORGANISM: Artificial Sequence
<220> FEATURE:
<223> OTHER INFORMATION: Synthetic

<400> SEQUENCE: 144

Thr Arg Asp Arg Asn Arg Gln Arg Asn Tyr Phe Tyr Asp Gly Met Asp
1               5                   10                  15

Val

<210> SEQ ID NO 145
<211> LENGTH: 339
<212> TYPE: DNA
<213> ORGANISM: Artificial Sequence
<220> FEATURE:
<223> OTHER INFORMATION: Synthetic
```

<400> SEQUENCE: 145

```
gacatccagt tgacccagtc tccagtctcc ctgcccgtca cccctggaga gccggcctcc      60
atctcctgca ggtctagtca gaggctcctg cataataatg gaaacaacta tttggattgg    120
tacctgcaga agccagggca gtctccacaa ctcctgatct atttgggctc taatcgggcc    180
tccggggtcc ctgacaggtt cagtggcagt ggatcaggca cagatttcac actgaaagtc    240
agtagagtgg aggctgagga tgttggggtt tattactgca tgcaagctct acaaactccg    300 tacactttg gccaggggac caagctggag atcaaacga                            339
```

<210> SEQ ID NO 146
<211> LENGTH: 113
<212> TYPE: PRT
<213> ORGANISM: Artificial Sequence
<220> FEATURE:
<223> OTHER INFORMATION: Synthetic

<400> SEQUENCE: 146

```
Asp Ile Gln Leu Thr Gln Ser Pro Val Ser Leu Pro Val Thr Pro Gly
 1               5                  10                  15

Glu Pro Ala Ser Ile Ser Cys Arg Ser Ser Gln Arg Leu Leu His Asn
            20                  25                  30

Asn Gly Asn Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Val
65                  70                  75                  80

Ser Arg Val Glu Ala Glu Asp Val Gly Val Tyr Tyr Cys Met Gln Ala
                85                  90                  95

Leu Gln Thr Pro Tyr Thr Phe Gly Gln Gly Thr Lys Leu Glu Ile Lys
            100                 105                 110

Arg
```

<210> SEQ ID NO 147
<211> LENGTH: 33
<212> TYPE: DNA
<213> ORGANISM: Artificial Sequence
<220> FEATURE:
<223> OTHER INFORMATION: Synthetic

<400> SEQUENCE: 147

```
cagaggctcc tgcataataa tggaaacaac tat                                  33
```

<210> SEQ ID NO 148
<211> LENGTH: 11
<212> TYPE: PRT
<213> ORGANISM: Artificial Sequence
<220> FEATURE:
<223> OTHER INFORMATION: Synthetic

<400> SEQUENCE: 148

```
Gln Arg Leu Leu His Asn Asn Gly Asn Asn Tyr
 1               5                  10
```

<210> SEQ ID NO 149
<211> LENGTH: 9
<212> TYPE: DNA
<213> ORGANISM: Artificial Sequence
<220> FEATURE:
<223> OTHER INFORMATION: Synthetic

```
<400> SEQUENCE: 149 ttgggctct                                                              9

<210> SEQ ID NO 150
<211> LENGTH: 3
<212> TYPE: PRT
<213> ORGANISM: Artificial Sequence
<220> FEATURE:
<223> OTHER INFORMATION: Synthetic

<400> SEQUENCE: 150

Leu Gly Ser
 1

<210> SEQ ID NO 151
<211> LENGTH: 27
<212> TYPE: DNA
<213> ORGANISM: Artificial Sequence
<220> FEATURE:
<223> OTHER INFORMATION: Synthetic

<400> SEQUENCE: 151
atgcaagctc tacaaactcc gtacact                                         27

<210> SEQ ID NO 152
<211> LENGTH: 9
<212> TYPE: PRT
<213> ORGANISM: Artificial Sequence
<220> FEATURE:
<223> OTHER INFORMATION: Synthetic

<400> SEQUENCE: 152

Met Gln Ala Leu Gln Thr Pro Tyr Thr
 1               5

<210> SEQ ID NO 153
<211> LENGTH: 375
<212> TYPE: DNA
<213> ORGANISM: Artificial Sequence
<220> FEATURE:
<223> OTHER INFORMATION: Synthetic

<400> SEQUENCE: 153
gaggtgcagc tggtggagtc tgggggagcc ttggtaaagc ctgggggtc ccttagactc       60 tcctgtgcag tctctggatt cactttcatt aatgactgga tgaactgggt ccgccaggct    120
ccagggaagg gctggaatg ggttggccgt attaaaagca caactgatgg tgggacaaca    180
gacgacgctg cacccgtgaa aggcagattc accatctcaa gagatgactc aaaaaacacg    240
ctatatctgc aaatgaatag cctgaaaacc gaggacacag ccgtgtatta ctgtaccaga    300
gataggaacc gacagagaaa ttacttctat gacggtatgg acgtctgggg ccaagggacc    360
acggtcaccg tctcc                                                    375

<210> SEQ ID NO 154
<211> LENGTH: 125
<212> TYPE: PRT
<213> ORGANISM: Artificial Sequence
<220> FEATURE:
<223> OTHER INFORMATION: Synthetic

<400> SEQUENCE: 154

Glu Val Gln Leu Val Glu Ser Gly Gly Ala Leu Val Lys Pro Gly Gly
 1               5                  10                  15

Ser Leu Arg Leu Ser Cys Ala Val Ser Gly Phe Thr Phe Ile Asn Asp
```

```
                    20                  25                  30
Trp Met Asn Trp Val Arg Gln Ala Pro Gly Lys Gly Leu Glu Trp Val
            35                  40                  45

Gly Arg Ile Lys Ser Thr Thr Asp Gly Gly Thr Thr Asp Asp Ala Ala
        50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Arg Asp Arg Asn Arg Gln Arg Asn Tyr Phe Tyr Asp Gly
            100                 105                 110

Met Asp Val Trp Gly Gln Gly Thr Thr Val Thr Val Ser
        115                 120                 125

<210> SEQ ID NO 155
<211> LENGTH: 336
<212> TYPE: DNA
<213> ORGANISM: Artificial Sequence
<220> FEATURE:
<223> OTHER INFORMATION: Synthetic

<400> SEQUENCE: 155
gacatcgtga tgacccagtc tccagtctcc ctgcccgtca cccctggaga gccggcctcc      60
atctcctgca ggtctagtca gaggctcctg cataataatg gaaacaacta tttggattgg     120
tacctgcaga agccagggca gtctccacaa ctcctgatct atttgggctc taatcgggcc     180
tccggggtcc ctgacaggtt cagtggcagt ggatcaggca cagatttcac actgaaagtc     240
agtagagtgg aggctgagga tgttggggtt tattactgca tgcaagctct acaaactccg     300 tacactttg gccaggggac caagctggag atcaaa                                336

<210> SEQ ID NO 156
<211> LENGTH: 112
<212> TYPE: PRT
<213> ORGANISM: Artificial Sequence
<220> FEATURE:
<223> OTHER INFORMATION: Synthetic

<400> SEQUENCE: 156

Asp Ile Val Met Thr Gln Ser Pro Val Ser Leu Pro Val Thr Pro Gly
1               5                   10                  15

Glu Pro Ala Ser Ile Ser Cys Arg Ser Ser Gln Arg Leu Leu His Asn
            20                  25                  30

Asn Gly Asn Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Val
65                  70                  75                  80

Ser Arg Val Glu Ala Glu Asp Val Gly Val Tyr Tyr Cys Met Gln Ala
                85                  90                  95

Leu Gln Thr Pro Tyr Thr Phe Gly Gln Gly Thr Lys Leu Glu Ile Lys
            100                 105                 110

<210> SEQ ID NO 157
<211> LENGTH: 351
<212> TYPE: DNA
<213> ORGANISM: Artificial Sequence
<220> FEATURE:
<223> OTHER INFORMATION: Synthetic
```

<400> SEQUENCE: 157

```
gaggtgcagc tggtggagtc tgggggaggc ttggtacagc ctggggggtc cctgagactc      60
tcctgtgcag cctctggatt cacctttagc agttatgcca tgacctgggt ccgccaggct     120
ccagggaagg ggcttgagtg ggtctcaggt gtaagtggaa gaggtggtag tacatactac     180
gcagactccg tgaagggccg gttcaccatc tccagagaca attccaagaa cacgctgtat     240
cttcaaatga acagcctgag agccgaggac acggccgtgt attactgtgc gtattgggat     300
atcagctcgt ttgactactg gggccaggga accctggtca ctgtctcctc a             351
```

<210> SEQ ID NO 158
<211> LENGTH: 117
<212> TYPE: PRT
<213> ORGANISM: Artificial Sequence
<220> FEATURE:
<223> OTHER INFORMATION: Synthetic

<400> SEQUENCE: 158

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Thr Trp Val Arg Gln Ala Pro Gly Lys Gly Leu Glu Trp Val
        35                  40                  45

Ser Gly Val Ser Gly Arg Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Tyr Trp Asp Ile Ser Ser Phe Asp Tyr Trp Gly Gln Gly Thr Leu
            100                 105                 110

Val Thr Val Ser Ser
        115
```

<210> SEQ ID NO 159
<211> LENGTH: 24
<212> TYPE: DNA
<213> ORGANISM: Artificial Sequence
<220> FEATURE:
<223> OTHER INFORMATION: Synthetic

<400> SEQUENCE: 159

```
ggattcacct ttagcagtta tgcc                                              24
```

<210> SEQ ID NO 160
<211> LENGTH: 8
<212> TYPE: PRT
<213> ORGANISM: Artificial Sequence
<220> FEATURE:
<223> OTHER INFORMATION: Synthetic

<400> SEQUENCE: 160

```
Gly Phe Thr Phe Ser Ser Tyr Ala
 1               5
```

<210> SEQ ID NO 161
<211> LENGTH: 24
<212> TYPE: DNA
<213> ORGANISM: Artificial Sequence
<220> FEATURE:

```
<223> OTHER INFORMATION: Synthetic

<400> SEQUENCE: 161
gtaagtggaa gaggtggtag taca                                              24

<210> SEQ ID NO 162
<211> LENGTH: 8
<212> TYPE: PRT
<213> ORGANISM: Artificial Sequence
<220> FEATURE:
<223> OTHER INFORMATION: Synthetic

<400> SEQUENCE: 162

Val Ser Gly Arg Gly Gly Ser Thr
 1               5

<210> SEQ ID NO 163
<211> LENGTH: 30
<212> TYPE: DNA
<213> ORGANISM: Artificial Sequence
<220> FEATURE:
<223> OTHER INFORMATION: Synthetic

<400> SEQUENCE: 163
gcgtattggg atatcagctc gtttgactac                                        30

<210> SEQ ID NO 164
<211> LENGTH: 10
<212> TYPE: PRT
<213> ORGANISM: Artificial Sequence
<220> FEATURE:
<223> OTHER INFORMATION: Synthetic

<400> SEQUENCE: 164

Ala Tyr Trp Asp Ile Ser Ser Phe Asp Tyr
 1               5                  10

<210> SEQ ID NO 165
<211> LENGTH: 324
<212> TYPE: DNA
<213> ORGANISM: Artificial Sequence
<220> FEATURE:
<223> OTHER INFORMATION: Synthetic

<400> SEQUENCE: 165
gacatccagt tgacccagtc tccatccttc ctgtctgcat ctgtaggaga cagagtcacc       60
atcacttgct gggccagtca gggcattagc acttatttag cctggtatca gcaaaaacca      120
gggaaaaccc ctaaactcct gatctatgct gcatccactt tgcaaagtgg agtcccatca      180
aggttcagcg gcagtggatc tgggacagat ttcactctca caatcagcag cctgcagcct      240
gaagattttg caacttatta ctgtcaacag tttaatagtt acccgctcac tttcggcgga      300
gggaccaagc tggagatcaa acga                                             324

<210> SEQ ID NO 166
<211> LENGTH: 108
<212> TYPE: PRT
<213> ORGANISM: Artificial Sequence
<220> FEATURE:
<223> OTHER INFORMATION: Synthetic

<400> SEQUENCE: 166

Asp Ile Gln Leu Thr Gln Ser Pro Ser Phe Leu Ser Ala Ser Val Gly
 1               5                  10                  15

Asp Arg Val Thr Ile Thr Cys Trp Ala Ser Gln Gly Ile Ser Thr Tyr
```

```
            20                  25                  30
Leu Ala Trp Tyr Gln Gln Lys Pro Gly Lys Thr Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Leu Glu Ile Lys Arg
            100                 105
```

<210> SEQ ID NO 167
<211> LENGTH: 18
<212> TYPE: DNA
<213> ORGANISM: Artificial Sequence
<220> FEATURE:
<223> OTHER INFORMATION: Synthetic

<400> SEQUENCE: 167
cagggcatta gcacttat                                                 18

<210> SEQ ID NO 168
<211> LENGTH: 6
<212> TYPE: PRT
<213> ORGANISM: Artificial Sequence
<220> FEATURE:
<223> OTHER INFORMATION: Synthetic

<400> SEQUENCE: 168

Gln Gly Ile Ser Thr Tyr
1               5

<210> SEQ ID NO 169
<211> LENGTH: 9
<212> TYPE: DNA
<213> ORGANISM: Artificial Sequence
<220> FEATURE:
<223> OTHER INFORMATION: Synthetic

<400> SEQUENCE: 169 gctgcatcc                                                            9

<210> SEQ ID NO 170
<211> LENGTH: 3
<212> TYPE: PRT
<213> ORGANISM: Artificial Sequence
<220> FEATURE:
<223> OTHER INFORMATION: Synthetic

<400> SEQUENCE: 170

Ala Ala Ser
1

<210> SEQ ID NO 171
<211> LENGTH: 27
<212> TYPE: DNA
<213> ORGANISM: Artificial Sequence
<220> FEATURE:
<223> OTHER INFORMATION: Synthetic

<400> SEQUENCE: 171
caacagttta atagttaccc gctcact                                       27

<210> SEQ ID NO 172
<211> LENGTH: 9
<212> TYPE: PRT
<213> ORGANISM: Artificial Sequence
<220> FEATURE:
<223> OTHER INFORMATION: Synthetic

<400> SEQUENCE: 172

Gln Gln Phe Asn Ser Tyr Pro Leu Thr
1               5

<210> SEQ ID NO 173
<211> LENGTH: 351
<212> TYPE: DNA
<213> ORGANISM: Artificial Sequence
<220> FEATURE:
<223> OTHER INFORMATION: Synthetic

<400> SEQUENCE: 173
gaggtgcagc tggtggagtc tgggggaggc ttggtacagc ctggggggtc cctgagactc    60
tcctgtgcag cctctggatt cacctttagc agttatgcca tgacctgggt ccgccaggct   120
ccagggaagg ggcttgagtg ggtctcaggt gtaagtggaa gaggtggtag tacatactac   180
gcagactccg tgaagggccg gttcaccatc tccagagaca attccaagaa cacgctgtat   240
cttcaaatga acagcctgag agccgaggac acggccgtgt attactgtgc gtattgggat   300
atcagctcgt tgactactgg ggccaggga accctggtca ctgtctcctc a             351

<210> SEQ ID NO 174
<211> LENGTH: 117
<212> TYPE: PRT
<213> ORGANISM: Artificial Sequence
<220> FEATURE:
<223> OTHER INFORMATION: Synthetic

<400> SEQUENCE: 174

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Thr Trp Val Arg Gln Ala Pro Gly Lys Gly Leu Glu Trp Val
        35                  40                  45

Ser Gly Val Ser Gly Arg Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Tyr Trp Asp Ile Ser Ser Phe Asp Tyr Trp Gly Gln Gly Thr Leu
            100                 105                 110

Val Thr Val Ser Ser
        115

<210> SEQ ID NO 175
<211> LENGTH: 321
<212> TYPE: DNA
<213> ORGANISM: Artificial Sequence
<220> FEATURE:
<223> OTHER INFORMATION: Synthetic

<400> SEQUENCE: 175
gacatccagt tgacccagtc tccatccttc ctgtctgcat ctgtaggaga cagagtcacc    60

```
atcacttgct gggccagtca gggcattagc acttatttag cctggtatca gcaaaaacca    120
gggaaaaccc ctaaactcct gatctatgct gcatccactt tgcaaagtgg agtcccatca    180
aggttcagcg gcagtggatc tgggacagat ttcactctca caatcagcag cctgcagcct    240
gaagattttg caacttatta ctgtcaacag tttaatagtt acccgctcac tttcggcgga    300
gggaccaagg tggagatcaa a                                              321
```

<210> SEQ ID NO 176
<211> LENGTH: 107
<212> TYPE: PRT
<213> ORGANISM: Artificial Sequence
<220> FEATURE:
<223> OTHER INFORMATION: Synthetic

<400> SEQUENCE: 176

Asp Ile Gln Leu Thr Gln Ser Pro Ser Phe Leu Ser Ala Ser Val Gly
1               5                   10                  15

Asp Arg Val Thr Ile Thr Cys Trp Ala Ser Gln Gly Ile Ser Thr Tyr
            20                  25                  30

Leu Ala Trp Tyr Gln Gln Lys Pro Gly Lys Thr Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys
            100                 105

<210> SEQ ID NO 177
<211> LENGTH: 369
<212> TYPE: DNA
<213> ORGANISM: Artificial Sequence
<220> FEATURE:
<223> OTHER INFORMATION: Synthetic

<400> SEQUENCE: 177

```
gaggtgcagc tggtggagtc tggggggaggc gtggtccagc ctgggagatc cctgagactc    60
tcctgtgtgg cctctggatt caccttcagt aactatggca tgcactgggt ccgccaggct   120
ccaggcaagg ggctggaatg ggtggcagtt atatcatatg atggaaataa tgatttgtat   180
tcagactccg tgaagggccg attcaccatc tccagagaca atgccaagaa cgcgctgtct   240
ctgcaaatga ccagcctgag agctgaggac acggctgtct attactgtgc gagagatagt   300
acgatgactc cctactacta ccacggtata gacgtctggg gccaagggac cacggtcacc   360
gtctcctca                                                           369
```

<210> SEQ ID NO 178
<211> LENGTH: 123
<212> TYPE: PRT
<213> ORGANISM: Artificial Sequence
<220> FEATURE:
<223> OTHER INFORMATION: Synthetic

<400> SEQUENCE: 178

Glu Val Gln Leu Val Glu Ser Gly Gly Gly Val Val Gln Pro Gly Arg
1               5                   10                  15

Ser Leu Arg Leu Ser Cys Val Ala Ser Gly Phe Thr Phe Ser Asn Tyr
            20                  25                  30

Gly Met His Trp Val Arg Gln Ala Pro Gly Lys Gly Leu Glu Trp Val
         35                  40                  45

Ala Val Ile Ser Tyr Asp Gly Asn Asn Asp Leu Tyr Ser Asp Ser Val
 50                  55                  60

Lys Gly Arg Phe Thr Ile Ser Arg Asp Asn Lys Asn Ala Leu Ser
 65                  70                  75                  80

Leu Gln Met Thr Ser Leu Arg Ala Glu Asp Thr Ala Val Tyr Tyr Cys
                 85                  90                  95

Ala Arg Asp Ser Thr Met Thr Pro Tyr Tyr Tyr His Gly Ile Asp Val
             100                 105                 110

Trp Gly Gln Gly Thr Thr Val Thr Val Ser Ser
         115                 120

<210> SEQ ID NO 179
<211> LENGTH: 24
<212> TYPE: DNA
<213> ORGANISM: Artificial Sequence
<220> FEATURE:
<223> OTHER INFORMATION: Synthetic

<400> SEQUENCE: 179
ggattcacct tcagtaacta tggc                                          24

<210> SEQ ID NO 180
<211> LENGTH: 8
<212> TYPE: PRT
<213> ORGANISM: Artificial Sequence
<220> FEATURE:
<223> OTHER INFORMATION: Synthetic

<400> SEQUENCE: 180

Gly Phe Thr Phe Ser Asn Tyr Gly
 1               5

<210> SEQ ID NO 181
<211> LENGTH: 24
<212> TYPE: DNA
<213> ORGANISM: Artificial Sequence
<220> FEATURE:
<223> OTHER INFORMATION: Synthetic

<400> SEQUENCE: 181
atatcatatg atggaaataa tgat                                          24

<210> SEQ ID NO 182
<211> LENGTH: 8
<212> TYPE: PRT
<213> ORGANISM: Artificial Sequence
<220> FEATURE:
<223> OTHER INFORMATION: Synthetic

<400> SEQUENCE: 182

Ile Ser Tyr Asp Gly Asn Asn Asp
 1               5

<210> SEQ ID NO 183
<211> LENGTH: 48
<212> TYPE: DNA
<213> ORGANISM: Artificial Sequence
<220> FEATURE:
<223> OTHER INFORMATION: Synthetic

<400> SEQUENCE: 183
gcgagagata gtacgatgac tccctactac taccacggta tagacgtc                48

```
<210> SEQ ID NO 184
<211> LENGTH: 16
<212> TYPE: PRT
<213> ORGANISM: Artificial Sequence
<220> FEATURE:
<223> OTHER INFORMATION: Synthetic

<400> SEQUENCE: 184

Ala Arg Asp Ser Thr Met Thr Pro Tyr Tyr Tyr His Gly Ile Asp Val
1               5                   10                  15

<210> SEQ ID NO 185
<211> LENGTH: 324
<212> TYPE: DNA
<213> ORGANISM: Artificial Sequence
<220> FEATURE:
<223> OTHER INFORMATION: Synthetic

<400> SEQUENCE: 185
gacatccaga tgacccagtc tccatcctcc ctgtctgcat ctgtaggaga cagagtcacc      60
atcacttgcc gggcaagtca ggacattaga aatgatttag ctggtatca gcagaaacca     120 gggaaagccc ctaagcgcct gatctatgct gcatccagtt tgcaaagtgg ggtcccatca    180
aggttcagcg gcagtggatc tgggacagac ttcactctca caatcagcag cctgcagcct    240
gaagattttg caacttatta ctgtctacag cataatagtt accctccgac gttcggccaa    300
gggaccaagg tggagatcaa acga                                            324

<210> SEQ ID NO 186
<211> LENGTH: 108
<212> TYPE: PRT
<213> ORGANISM: Artificial Sequence
<220> FEATURE:
<223> OTHER INFORMATION: Synthetic

<400> SEQUENCE: 186

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln His Asn Ser Tyr Pro Pro
                85                  90                  95

Thr Phe Gly Gln Gly Thr Lys Val Glu Ile Lys Arg
            100                 105

<210> SEQ ID NO 187
<211> LENGTH: 18
<212> TYPE: DNA
<213> ORGANISM: Artificial Sequence
<220> FEATURE:
<223> OTHER INFORMATION: Synthetic

<400> SEQUENCE: 187
caggacatta gaaatgat                                                    18
```

```
<210> SEQ ID NO 188
<211> LENGTH: 6
<212> TYPE: PRT
<213> ORGANISM: Artificial Sequence
<220> FEATURE:
<223> OTHER INFORMATION: Synthetic

<400> SEQUENCE: 188

Gln Asp Ile Arg Asn Asp
 1               5

<210> SEQ ID NO 189
<211> LENGTH: 9
<212> TYPE: DNA
<213> ORGANISM: Artificial Sequence
<220> FEATURE:
<223> OTHER INFORMATION: Synthetic

<400> SEQUENCE: 189 gctgcatcc                                                                  9

<210> SEQ ID NO 190
<211> LENGTH: 3
<212> TYPE: PRT
<213> ORGANISM: Artificial Sequence
<220> FEATURE:
<223> OTHER INFORMATION: Synthetic

<400> SEQUENCE: 190

Ala Ala Ser
 1

<210> SEQ ID NO 191
<211> LENGTH: 27
<212> TYPE: DNA
<213> ORGANISM: Artificial Sequence
<220> FEATURE:
<223> OTHER INFORMATION: Synthetic

<400> SEQUENCE: 191
ctacagcata atagttaccc tccgacg                                              27

<210> SEQ ID NO 192
<211> LENGTH: 9
<212> TYPE: PRT
<213> ORGANISM: Artificial Sequence
<220> FEATURE:
<223> OTHER INFORMATION: Synthetic

<400> SEQUENCE: 192

Leu Gln His Asn Ser Tyr Pro Pro Thr
 1               5

<210> SEQ ID NO 193
<211> LENGTH: 366
<212> TYPE: DNA
<213> ORGANISM: Artificial Sequence
<220> FEATURE:
<223> OTHER INFORMATION: Synthetic

<400> SEQUENCE: 193
caggtgcagc tggtggagtc tgggggaggc gtggtccagc ctgggagatc cctgagactc          60
tcctgtgtgg cctctggatt caccttcagt aactatggca tgcactgggt ccgccaggct         120
ccaggcaagg ggctggaatg ggtggcagtt atatcatatg atggaaataa tgatttgtat         180
tcagactccg tgaagggccg attcaccatc tccagagaca tgccaagaa cgcgctgtct          240
```

```
ctgcaaatga ccagcctgag agctgaggac acggctgtct attactgtgc gagagatagt    300
acgatgactc cctactacta ccacggtata cgtctggg gccaagggac acggtcacc       360 gtctcc                                                               366
```

<210> SEQ ID NO 194
<211> LENGTH: 122
<212> TYPE: PRT
<213> ORGANISM: Artificial Sequence
<220> FEATURE:
<223> OTHER INFORMATION: Synthetic

<400> SEQUENCE: 194

```
Gln Val Gln Leu Val Glu Ser Gly Gly Gly Val Val Gln Pro Gly Arg
 1               5                  10                  15

Ser Leu Arg Leu Ser Cys Val Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ala Val Ile Ser Tyr Asp Gly Asn Asn Asp Leu Tyr Ser Asp Ser Val
    50                  55                  60

Lys Gly Arg Phe Thr Ile Ser Arg Asp Asn Ala Lys Asn Ala Leu Ser
65                  70                  75                  80

Leu Gln Met Thr Ser Leu Arg Ala Glu Asp Thr Ala Val Tyr Tyr Cys
                85                  90                  95

Ala Arg Asp Ser Thr Met Thr Pro Tyr Tyr Tyr His Gly Ile Asp Val
            100                 105                 110

Trp Gly Gln Gly Thr Thr Val Thr Val Ser
        115                 120
```

<210> SEQ ID NO 195
<211> LENGTH: 321
<212> TYPE: DNA
<213> ORGANISM: Artificial Sequence
<220> FEATURE:
<223> OTHER INFORMATION: Synthetic

<400> SEQUENCE: 195

```
gacatccaga tgacccagtc tccatcctcc ctgtctgcat ctgtaggaga cagagtcacc     60
atcacttgcc gggcaagtca ggacattaga aatgatttag ctggtatca gcagaaacca    120 gggaaagccc ctaagcgcct gatctatgct gcatccagtt tgcaaagtgg ggtcccatca   180
aggttcagcg gcagtggatc tgggacagac ttcactctca caatcagcag cctgcagcct   240
gaagattttg caacttatta ctgtctacag cataatagtt accctccgac gttcggccaa   300
gggaccaagg tggagatcaa a                                             321
```

<210> SEQ ID NO 196
<211> LENGTH: 107
<212> TYPE: PRT
<213> ORGANISM: Artificial Sequence
<220> FEATURE:
<223> OTHER INFORMATION: Synthetic

<400> SEQUENCE: 196

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Arg Asn Asp
            20                  25                  30

Leu Gly Trp Tyr Gln Gln Lys Pro Gly Lys Ala Pro Lys Arg Leu Ile
        35                  40                  45
```

```
Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Leu Gln His Asn Ser Tyr Pro Pro
                 85                  90                  95

Thr Phe Gly Gln Gly Thr Lys Val Glu Ile Lys
            100                 105
```

<210> SEQ ID NO 197
<211> LENGTH: 363
<212> TYPE: DNA
<213> ORGANISM: Artificial Sequence
<220> FEATURE:
<223> OTHER INFORMATION: Synthetic

<400> SEQUENCE: 197

```
gaggtgcagc tggtggagtc tgggggaggc ttggtgcagc ctggggggtc cctgagactc    60
tcctgttcag cctctggatt cacctttagt aaatatgtca tgacctgggt ccgccaggct   120
ccagggaagg gactggagtg gtctcagct attggtccta ctggtcgtac cacggaatac   180
gcagactccg tgcagggccg cttcaccatc tccagagaca attccatgaa cacggttttt   240
cttcacttga acagtctgac agccgaggac acggccgaat attattgtgc gaagatgttt   300
gactggaatt acgacgtgta ctttgactcc tggggccagg gaaccctggt cactgtctcc   360
tca                                                                 363
```

<210> SEQ ID NO 198
<211> LENGTH: 121
<212> TYPE: PRT
<213> ORGANISM: Artificial Sequence
<220> FEATURE:
<223> OTHER INFORMATION: Synthetic

<400> SEQUENCE: 198

```
Glu Val Gln Leu Val Glu Ser Gly Gly Gly Leu Val Gln Pro Gly Gly
  1               5                  10                  15

Ser Leu Arg Leu Ser Cys Ser Ala Ser Gly Phe Thr Phe Ser Lys Tyr
             20                  25                  30

Val Met Thr Trp Val Arg Gln Ala Pro Gly Lys Gly Leu Glu Trp Val
         35                  40                  45

Ser Ala Ile Gly Pro Thr Gly Arg Thr Thr Glu Tyr Ala Asp Ser Val
     50                  55                  60

Gln Gly Arg Phe Thr Ile Ser Arg Asp Asn Ser Met Asn Thr Val Phe
 65                  70                  75                  80

Leu His Leu Asn Ser Leu Thr Ala Glu Asp Thr Ala Glu Tyr Tyr Cys
                 85                  90                  95

Ala Lys Met Phe Asp Trp Asn Tyr Asp Val Tyr Phe Asp Ser Trp Gly
            100                 105                 110

Gln Gly Thr Leu Val Thr Val Ser Ser
        115                 120
```

<210> SEQ ID NO 199
<211> LENGTH: 24
<212> TYPE: DNA
<213> ORGANISM: Artificial Sequence
<220> FEATURE:
<223> OTHER INFORMATION: Synthetic

<400> SEQUENCE: 199

```
ggattcacct ttagtaaata tgtc                                         24
```

<210> SEQ ID NO 200
<211> LENGTH: 8
<212> TYPE: PRT
<213> ORGANISM: Artificial Sequence
<220> FEATURE:
<223> OTHER INFORMATION: Synthetic

<400> SEQUENCE: 200

Gly Phe Thr Phe Ser Lys Tyr Val
1               5

<210> SEQ ID NO 201
<211> LENGTH: 24
<212> TYPE: DNA
<213> ORGANISM: Artificial Sequence
<220> FEATURE:
<223> OTHER INFORMATION: Synthetic

<400> SEQUENCE: 201

```
attggtccta ctggtcgtac cacg                                         24
```

<210> SEQ ID NO 202
<211> LENGTH: 8
<212> TYPE: PRT
<213> ORGANISM: Artificial Sequence
<220> FEATURE:
<223> OTHER INFORMATION: Synthetic

<400> SEQUENCE: 202

Ile Gly Pro Thr Gly Arg Thr Thr
1               5

<210> SEQ ID NO 203
<211> LENGTH: 42
<212> TYPE: DNA
<213> ORGANISM: Artificial Sequence
<220> FEATURE:
<223> OTHER INFORMATION: Synthetic

<400> SEQUENCE: 203

```
gcgaagatgt ttgactggaa ttacgacgtg tactttgact cc                     42
```

<210> SEQ ID NO 204
<211> LENGTH: 14
<212> TYPE: PRT
<213> ORGANISM: Artificial Sequence
<220> FEATURE:
<223> OTHER INFORMATION: Synthetic

<400> SEQUENCE: 204

Ala Lys Met Phe Asp Trp Asn Tyr Asp Val Tyr Phe Asp Ser
1               5                   10

<210> SEQ ID NO 205
<211> LENGTH: 321
<212> TYPE: DNA
<213> ORGANISM: Artificial Sequence
<220> FEATURE:
<223> OTHER INFORMATION: Synthetic

<400> SEQUENCE: 205

```
gacatccaga tgacccagtc tccctccatc ttgtctgcat ctgtaggaga cagagtcacc   60
atcacttgcc ggaccagtca gagtattagt aattggttgg cctggtatca gcagaaacca  120
```

```
gggaaagccc ctaacctcct gatctataag gcgtctagtt tagaaagtgg ggtcccatca    180
aggttcagcg gcagtggatc tgggacagaa ttcactctca ccatcagcag cctgcagcct    240
gatgattttg caacttatta ctgtcaacag tattatagat attggacgtt cggccaaggg    300
accaaggtgg agatcaaacg a                                              321
```

<210> SEQ ID NO 206
<211> LENGTH: 107
<212> TYPE: PRT
<213> ORGANISM: Artificial Sequence
<220> FEATURE:
<223> OTHER INFORMATION: Synthetic

<400> SEQUENCE: 206

```
Asp Ile Gln Met Thr Gln Ser Pro Ser Ile Leu Ser Ala Ser Val Gly
 1               5                  10                  15

Asp Arg Val Thr Ile Thr Cys Arg Thr Ser Gln Ser Ile Ser Asn Trp
            20                  25                  30

Leu Ala Trp Tyr Gln Gln Lys Pro Gly Lys Ala Pro Asn Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Tyr Arg Tyr Trp Thr
                85                  90                  95

Phe Gly Gln Gly Thr Lys Val Glu Ile Lys Arg
            100                 105
```

<210> SEQ ID NO 207
<211> LENGTH: 18
<212> TYPE: DNA
<213> ORGANISM: Artificial Sequence
<220> FEATURE:
<223> OTHER INFORMATION: Synthetic

<400> SEQUENCE: 207

```
cagagtatta gtaattgg                                                   18
```

<210> SEQ ID NO 208
<211> LENGTH: 6
<212> TYPE: PRT
<213> ORGANISM: Artificial Sequence
<220> FEATURE:
<223> OTHER INFORMATION: Synthetic

<400> SEQUENCE: 208

```
Gln Ser Ile Ser Asn Trp
 1               5
```

<210> SEQ ID NO 209
<211> LENGTH: 9
<212> TYPE: DNA
<213> ORGANISM: Artificial Sequence
<220> FEATURE:
<223> OTHER INFORMATION: Synthetic

<400> SEQUENCE: 209

```
aaggcgtct                                                              9
```

<210> SEQ ID NO 210
<211> LENGTH: 3
<212> TYPE: PRT

<213> ORGANISM: Artificial Sequence
<220> FEATURE:
<223> OTHER INFORMATION: Synthetic

<400> SEQUENCE: 210

Lys Ala Ser
 1

<210> SEQ ID NO 211
<211> LENGTH: 24
<212> TYPE: DNA
<213> ORGANISM: Artificial Sequence
<220> FEATURE:
<223> OTHER INFORMATION: Synthetic

<400> SEQUENCE: 211
caacagtatt atagatattg gacg                                          24

<210> SEQ ID NO 212
<211> LENGTH: 8
<212> TYPE: PRT
<213> ORGANISM: Artificial Sequence
<220> FEATURE:
<223> OTHER INFORMATION: Synthetic

<400> SEQUENCE: 212

Gln Gln Tyr Tyr Arg Tyr Trp Thr
 1               5

<210> SEQ ID NO 213
<211> LENGTH: 363
<212> TYPE: DNA
<213> ORGANISM: Artificial Sequence
<220> FEATURE:
<223> OTHER INFORMATION: Synthetic

<400> SEQUENCE: 213
gaggtgcagc tggtggagtc tgggggaggc ttggtgcagc ctggggggtc cctgagactc      60
tcctgttcag cctctggatt cacctttagt aaatatgtca tgacctgggt ccgccaggct     120
ccagggaagg gactggagtg gtctcagct attggtccta ctggtcgtac cacggaatac     180
gcagactccg tgcagggccg cttcaccatc tccagagaca attccatgaa cacggttttt     240
cttcacttga cagtctgac agccgaggac acggccgaat attattgtgc gaagatgttt      300
gactggaatt acgacgtgta ctttgactcc tggggccagg aaccctggt caccgtctcc      360 tca                                                                  363

<210> SEQ ID NO 214
<211> LENGTH: 121
<212> TYPE: PRT
<213> ORGANISM: Artificial Sequence
<220> FEATURE:
<223> OTHER INFORMATION: Synthetic

<400> SEQUENCE: 214

Glu Val Gln Leu Val Glu Ser Gly Gly Gly Leu Val Gln Pro Gly Gly
 1               5                  10                  15

Ser Leu Arg Leu Ser Cys Ser Ala Ser Gly Phe Thr Phe Ser Lys Tyr
             20                  25                  30

Val Met Thr Trp Val Arg Gln Ala Pro Gly Lys Gly Leu Glu Trp Val
         35                  40                  45

Ser Ala Ile Gly Pro Thr Gly Arg Thr Thr Glu Tyr Ala Asp Ser Val
     50                  55                  60

```
Gln Gly Arg Phe Thr Ile Ser Arg Asp Asn Ser Met Asn Thr Val Phe
 65                  70                  75                  80

Leu His Leu Asn Ser Leu Thr Ala Glu Asp Thr Ala Glu Tyr Tyr Cys
                 85                  90                  95

Ala Lys Met Phe Asp Trp Asn Tyr Asp Val Tyr Phe Ser Trp Gly
            100                 105                 110

Gln Gly Thr Leu Val Thr Val Ser Ser
        115                 120
```

<210> SEQ ID NO 215
<211> LENGTH: 318
<212> TYPE: DNA
<213> ORGANISM: Artificial Sequence
<220> FEATURE:
<223> OTHER INFORMATION: Synthetic

<400> SEQUENCE: 215

```
gacatccaga tgacccagtc tccctccatc ttgtctgcat ctgtaggaga cagagtcacc    60
atcacttgcc ggaccagtca gagtattagt aattggttgg cctggtatca gcagaaacca   120
gggaaagccc ctaacctcct gatctataag gcgtctagtt tagaaagtgg ggtcccatca   180
aggttcagcg gcagtggatc tgggacagaa ttcactctca ccatcagcag cctgcagcct   240
gatgattttg caacttatta ctgtcaacag tattatagat attggacgtt cggccaaggg   300
accaaggtgg agatcaaa                                                 318
```

<210> SEQ ID NO 216
<211> LENGTH: 106
<212> TYPE: PRT
<213> ORGANISM: Artificial Sequence
<220> FEATURE:
<223> OTHER INFORMATION: Synthetic

<400> SEQUENCE: 216

```
Asp Ile Gln Met Thr Gln Ser Pro Ser Ile Leu Ser Ala Ser Val Gly
 1               5                  10                  15

Asp Arg Val Thr Ile Thr Cys Arg Thr Ser Gln Ser Ile Ser Asn Trp
             20                  25                  30

Leu Ala Trp Tyr Gln Gln Lys Pro Gly Lys Ala Pro Asn Leu Leu Ile
         35                  40                  45

Tyr Lys Ala Ser Ser Leu Glu Ser Gly Val Pro Ser Arg Phe Ser Gly
     50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Tyr Arg Tyr Trp Thr
                 85                  90                  95

Phe Gly Gln Gly Thr Lys Val Glu Ile Lys
            100                 105
```

<210> SEQ ID NO 217
<211> LENGTH: 369
<212> TYPE: DNA
<213> ORGANISM: Artificial Sequence
<220> FEATURE:
<223> OTHER INFORMATION: Synthetic

<400> SEQUENCE: 217

```
caggttcagc tggtgcagtc tgggggaggc ttggtacagc ctggggggtc cctgagactc    60
tcctgtgcag cctctggatt cacctttagt aattatgtca tgaactgggt ccgccaggct   120
ccagggaagg ggctggagtg ggtctcagtt ataagtggta gtggcggtag cacacactac   180
```

```
gcagactccg tgaagggccg gttcaccatc tccagagaca attccaaaga cgcgctgtat    240
ctacaaatga acagcctgag agccgaggac acggccgttt attactgtgc gaaaggcccg    300
ctggaggctt actactacta caacggtatg gacgtctggg gccaagggac cacggtcacc    360
gtctcctca                                                            369
```

<210> SEQ ID NO 218
<211> LENGTH: 123
<212> TYPE: PRT
<213> ORGANISM: Artificial Sequence
<220> FEATURE:
<223> OTHER INFORMATION: Synthetic

<400> SEQUENCE: 218

Gln Val Gln Leu Val Gln Ser Gly Gly Gly Leu Val Gln Pro Gly Gly
 1               5                  10                  15

Ser Leu Arg Leu Ser Cys Ala Ala Ser Gly Phe Thr Phe Ser Asn Tyr
            20                  25                  30

Val Met Asn Trp Val Arg Gln Ala Pro Gly Lys Gly Leu Glu Trp Val
        35                  40                  45

Ser Val Ile Ser Gly Ser Gly Gly Ser Thr His Tyr Ala Asp Ser Val
    50                  55                  60

Lys Gly Arg Phe Thr Ile Ser Arg Asp Asn Ser Lys Asp Ala Leu Tyr
65                  70                  75                  80

Leu Gln Met Asn Ser Leu Arg Ala Glu Asp Thr Ala Val Tyr Tyr Cys
                85                  90                  95

Ala Lys Gly Pro Leu Glu Ala Tyr Tyr Tyr Tyr Asn Gly Met Asp Val
            100                 105                 110

Trp Gly Gln Gly Thr Thr Val Thr Val Ser Ser
        115                 120

<210> SEQ ID NO 219
<211> LENGTH: 24
<212> TYPE: DNA
<213> ORGANISM: Artificial Sequence
<220> FEATURE:
<223> OTHER INFORMATION: Synthetic

<400> SEQUENCE: 219

```
ggattcacct ttagtaatta tgtc                                            24
```

<210> SEQ ID NO 220
<211> LENGTH: 8
<212> TYPE: PRT
<213> ORGANISM: Artificial Sequence
<220> FEATURE:
<223> OTHER INFORMATION: Synthetic

<400> SEQUENCE: 220

Gly Phe Thr Phe Ser Asn Tyr Val
 1               5

<210> SEQ ID NO 221
<211> LENGTH: 24
<212> TYPE: DNA
<213> ORGANISM: Artificial Sequence
<220> FEATURE:
<223> OTHER INFORMATION: Synthetic

<400> SEQUENCE: 221

```
ataagtggta gtggcggtag caca                                            24
```

<210> SEQ ID NO 222
<211> LENGTH: 8
<212> TYPE: PRT
<213> ORGANISM: Artificial Sequence
<220> FEATURE:
<223> OTHER INFORMATION: Synthetic

<400> SEQUENCE: 222

Ile Ser Gly Ser Gly Gly Ser Thr
1               5

<210> SEQ ID NO 223
<211> LENGTH: 48
<212> TYPE: DNA
<213> ORGANISM: Artificial Sequence
<220> FEATURE:
<223> OTHER INFORMATION: Synthetic

<400> SEQUENCE: 223
gcgaaaggcc cgctggaggc ttactactac tacaacggta tggacgtc          48

<210> SEQ ID NO 224
<211> LENGTH: 16
<212> TYPE: PRT
<213> ORGANISM: Artificial Sequence
<220> FEATURE:
<223> OTHER INFORMATION: Synthetic

<400> SEQUENCE: 224

Ala Lys Gly Pro Leu Glu Ala Tyr Tyr Tyr Tyr Asn Gly Met Asp Val
1               5                   10                  15

<210> SEQ ID NO 225
<211> LENGTH: 321
<212> TYPE: DNA
<213> ORGANISM: Artificial Sequence
<220> FEATURE:
<223> OTHER INFORMATION: Synthetic

<400> SEQUENCE: 225
gccatccaga tgacccagtc tccatccttc ctgtctgcat ctgtaggaga cagagtcacc     60
atcacttgct gggccagtca ggccattagc agttatttag cctggtatca gcacaaacca    120
gggagagccc ctaagctcct gatctattct acatccactt tgcaaagtgg agtcccatca    180
aggttcagcg gcagtggatc tgggacagaa ttcactctca caatcagcag cctgcagcct    240
gaagattttg caacttatta ctgtcaacag cttaatagtt accccacctt cggccaaggg    300
accaagctgg agatcaaacg a                                              321

<210> SEQ ID NO 226
<211> LENGTH: 107
<212> TYPE: PRT
<213> ORGANISM: Artificial Sequence
<220> FEATURE:
<223> OTHER INFORMATION: Synthetic

<400> SEQUENCE: 226

Ala Ile Gln Met Thr Gln Ser Pro Ser Phe Leu Ser Ala Ser Val Gly
1               5                   10                  15

Asp Arg Val Thr Ile Thr Cys Trp Ala Ser Gln Ala Ile Ser Ser Tyr
            20                  25                  30

Leu Ala Trp Tyr Gln His Lys Pro Gly Arg Ala Pro Lys Leu Leu Ile
        35                  40                  45

Tyr Ser Thr Ser Thr Leu Gln Ser Gly Val Pro Ser Arg Phe Ser Gly

```
                50                  55                  60
Ser Gly Ser Gly Thr Glu Phe Thr Leu Thr Ile Ser Ser Leu Gln Pro
 65                  70                  75                  80

Glu Asp Phe Ala Thr Tyr Tyr Cys Gln Gln Leu Asn Ser Tyr Pro Thr
                 85                  90                  95

Phe Gly Gln Gly Thr Lys Leu Glu Ile Lys Arg
            100                 105
```

```
<210> SEQ ID NO 227
<211> LENGTH: 18
<212> TYPE: DNA
<213> ORGANISM: Artificial Sequence
<220> FEATURE:
<223> OTHER INFORMATION: Synthetic

<400> SEQUENCE: 227
caggccatta gcagttat                                                 18
```

```
<210> SEQ ID NO 228
<211> LENGTH: 6
<212> TYPE: PRT
<213> ORGANISM: Artificial Sequence
<220> FEATURE:
<223> OTHER INFORMATION: Synthetic

<400> SEQUENCE: 228

Gln Ala Ile Ser Ser Tyr
 1               5
```

```
<210> SEQ ID NO 229
<211> LENGTH: 9
<212> TYPE: DNA
<213> ORGANISM: Artificial Sequence
<220> FEATURE:
<223> OTHER INFORMATION: Synthetic

<400> SEQUENCE: 229 tctacatcc                                                            9
```

```
<210> SEQ ID NO 230
<211> LENGTH: 3
<212> TYPE: PRT
<213> ORGANISM: Artificial Sequence
<220> FEATURE:
<223> OTHER INFORMATION: Synthetic

<400> SEQUENCE: 230

Ser Thr Ser
 1
```

```
<210> SEQ ID NO 231
<211> LENGTH: 24
<212> TYPE: DNA
<213> ORGANISM: Artificial Sequence
<220> FEATURE:
<223> OTHER INFORMATION: Synthetic

<400> SEQUENCE: 231
caacagctta atagttaccc cacc                                          24
```

```
<210> SEQ ID NO 232
<211> LENGTH: 8
<212> TYPE: PRT
<213> ORGANISM: Artificial Sequence
<220> FEATURE:
<223> OTHER INFORMATION: Synthetic
```

<400> SEQUENCE: 232

Gln Gln Leu Asn Ser Tyr Pro Thr
 1               5

<210> SEQ ID NO 233
<211> LENGTH: 369
<212> TYPE: DNA
<213> ORGANISM: Artificial Sequence
<220> FEATURE:
<223> OTHER INFORMATION: Synthetic

<400> SEQUENCE: 233

```
gaggtgcagc tggtggagtc tgggggaggc ttggtacagc ctgggggtc cctgagactc      60
tcctgtgcag cctctggatt cacctttagt aattatgtca tgaactgggt ccgccaggct    120
ccagggaagg gctggagtg gtctcagtt ataagtggta gtggcggtag cacacactac     180
gcagactccg tgaagggccg gttcaccatc tccagagaca attccaaaga cgcgctgtat    240
ctacaaatga acagcctgag agccgaggac acggccgttt attactgtgc gaaaggcccg    300
ctggaggctt actactacta caacggtatg gacgtctggg gccaagggac cacggtcacc    360
gtctcctca                                                            369
```

<210> SEQ ID NO 234
<211> LENGTH: 123
<212> TYPE: PRT
<213> ORGANISM: Artificial Sequence
<220> FEATURE:
<223> OTHER INFORMATION: Synthetic

<400> SEQUENCE: 234

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asn Tyr
            20                  25                  30

Val Met Asn Trp Val Arg Gln Ala Pro Gly Lys Gly Leu Glu Trp Val
        35                  40                  45

Ser Val Ile Ser Gly Ser Gly Gly Ser Thr His Tyr Ala Asp Ser Val
    50                  55                  60

Lys Gly Arg Phe Thr Ile Ser Arg Asp Asn Ser Lys Asp Ala Leu Tyr
65                  70                  75                  80

Leu Gln Met Asn Ser Leu Arg Ala Glu Asp Thr Ala Val Tyr Tyr Cys
                85                  90                  95

Ala Lys Gly Pro Leu Glu Ala Tyr Tyr Tyr Tyr Asn Gly Met Asp Val
            100                 105                 110

Trp Gly Gln Gly Thr Thr Val Thr Val Ser Ser
        115                 120

<210> SEQ ID NO 235
<211> LENGTH: 318
<212> TYPE: DNA
<213> ORGANISM: Artificial Sequence
<220> FEATURE:
<223> OTHER INFORMATION: Synthetic

<400> SEQUENCE: 235

```
gacatccagt tgacccagtc tccatccttc ctgtctgcat ctgtaggaga cagagtcacc     60
atcacttgct gggccagtca ggccattagc agttatttag cctggtatca gcacaaacca    120
gggagagccc ctaagctcct gatctattct acatccactt tgcaaagtgg agtcccatca    180
```

```
aggttcagcg gcagtggatc tgggacagaa ttcactctca caatcagcag cctgcagcct    240
gaagattttg caacttatta ctgtcaacag cttaatagtt accccacctt cggccaaggg    300
accaagctgg agatcaaa                                                  318
```

<210> SEQ ID NO 236
<211> LENGTH: 106
<212> TYPE: PRT
<213> ORGANISM: Artificial Sequence
<220> FEATURE:
<223> OTHER INFORMATION: Synthetic

<400> SEQUENCE: 236

```
Asp Ile Gln Leu Thr Gln Ser Pro Ser Phe Leu Ser Ala Ser Val Gly
  1               5                  10                  15

Asp Arg Val Thr Ile Thr Cys Trp Ala Ser Gln Ala Ile Ser Ser Tyr
             20                  25                  30

Leu Ala Trp Tyr Gln His Lys Pro Gly Arg Ala Pro Lys Leu Leu Ile
         35                  40                  45

Tyr Ser Thr Ser Thr Leu Gln Ser Gly Val Pro Ser Arg Phe Ser Gly
     50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Gln Gln Leu Asn Ser Tyr Pro Thr
                 85                  90                  95

Phe Gly Gln Gly Thr Lys Leu Glu Ile Lys
            100                 105
```

<210> SEQ ID NO 237
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(1)
<223> OTHER INFORMATION: Xaa = Gly
<220> FEATURE:
<221> NAME/KEY: VARIANT
<222> LOCATION: (2)...(2)
<223> OTHER INFORMATION: Xaa = Phe
<220> FEATURE:
<221> NAME/KEY: VARIANT
<222> LOCATION: (3)...(3)
<223> OTHER INFORMATION: Xaa = Thr
<220> FEATURE:
<221> NAME/KEY: VARIANT
<222> LOCATION: (4)...(4)
<223> OTHER INFORMATION: Xaa = Phe
<220> FEATURE:
<221> NAME/KEY: VARIANT
<222> LOCATION: (5)...(5)
<223> OTHER INFORMATION: Xaa = Ser
<220> FEATURE:
<221> NAME/KEY: VARIANT
<222> LOCATION: (6)...(6)
<223> OTHER INFORMATION: Xaa = Thr, Ser, or Asn
<220> FEATURE:
<221> NAME/KEY: VARIANT
<222> LOCATION: (7)...(7)
<223> OTHER INFORMATION: Xaa = Tyr
<220> FEATURE:
<221> NAME/KEY: VARIANT
<222> LOCATION: (8)...(8)
<223> OTHER INFORMATION: Xaa = Gly, Trp, Val, or Ala

<400> SEQUENCE: 237

Xaa Xaa Xaa Xaa Xaa Xaa Xaa Xaa

```
<210> SEQ ID NO 238
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(1)
<223> OTHER INFORMATION: Xaa = Ile or Val
<220> FEATURE:
<221> NAME/KEY: VARIANT
<222> LOCATION: (2)...(2)
<223> OTHER INFORMATION: Xaa = Ser or Lys
<220> FEATURE:
<221> NAME/KEY: VARIANT
<222> LOCATION: (3)...(3)
<223> OTHER INFORMATION: Xaa = Gly or Glu
<220> FEATURE:
<221> NAME/KEY: VARIANT
<222> LOCATION: (4)...(4)
<223> OTHER INFORMATION: Xaa = Thr, Asp, Ser, or Arg
<220> FEATURE:
<221> NAME/KEY: VARIANT
<222> LOCATION: (5)...(5)
<223> OTHER INFORMATION: Xaa = Gly
<220> FEATURE:
<221> NAME/KEY: VARIANT
<222> LOCATION: (6)...(6)
<223> OTHER INFORMATION: Xaa = Arg, Ser, or Gly
<220> FEATURE:
<221> NAME/KEY: VARIANT
<222> LOCATION: (7)...(7)
<223> OTHER INFORMATION: Xaa = Thr, Glu, or Ser
<220> FEATURE:
<221> NAME/KEY: VARIANT
<222> LOCATION: (8)...(8)
<223> OTHER INFORMATION: Xaa = Thr or Lys

<400> SEQUENCE: 238

Xaa Xaa Xaa Xaa Xaa Xaa Xaa Xaa
 1               5

<210> SEQ ID NO 239
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(1)
<223> OTHER INFORMATION: Xaa = Thr or Ala
<220> FEATURE:
<221> NAME/KEY: VARIANT
<222> LOCATION: (2)...(2)
<223> OTHER INFORMATION: Xaa = Lys, Arg or absent
<220> FEATURE:
<221> NAME/KEY: VARIANT
<222> LOCATION: (3)...(3)
<223> OTHER INFORMATION: Xaa = Glu, Gly or absent
<220> FEATURE:
<221> NAME/KEY: VARIANT
<222> LOCATION: (4)...(4)
<223> OTHER INFORMATION: Xaa = Asp, Pro or absent
<220> FEATURE:
<221> NAME/KEY: VARIANT
<222> LOCATION: (5)...(5)
<223> OTHER INFORMATION: Xaa = Leu or absent
<220> FEATURE:
<221> NAME/KEY: VARIANT
<222> LOCATION: (6)...(6)
<223> OTHER INFORMATION: Xaa = Arg, Tyr, Glu or absent
<220> FEATURE:
<221> NAME/KEY: VARIANT
```

```
<222> LOCATION: (7)...(7)
<223> OTHER INFORMATION: Xaa = Gly, Asp, Ala or absent
<220> FEATURE:
<221> NAME/KEY: VARIANT
<222> LOCATION: (8)...(8)
<223> OTHER INFORMATION: Xaa = Asp, Ser or Tyr
<220> FEATURE:
<221> NAME/KEY: VARIANT
<222> LOCATION: (9)...(9)
<223> OTHER INFORMATION: Xaa = Tyr or Trp
<220> FEATURE:
<221> NAME/KEY: VARIANT
<222> LOCATION: (10)...(10)
<223> OTHER INFORMATION: Xaa = Tyr or Asp
<220> FEATURE:
<221> NAME/KEY: VARIANT
<222> LOCATION: (11)...(11)
<223> OTHER INFORMATION: Xaa =Tyr, Lys or Ile
<220> FEATURE:
<221> NAME/KEY: VARIANT
<222> LOCATION: (12)...(12)
<223> OTHER INFORMATION: Xaa = Gly, Tyr, Asn, or Ser
<220> FEATURE:
<221> NAME/KEY: VARIANT
<222> LOCATION: (13)...(13)
<223> OTHER INFORMATION: Xaa =Val, Gly or Ser
<220> FEATURE:
<221> NAME/KEY: VARIANT
<222> LOCATION: (14)...(14)
<223> OTHER INFORMATION: Xaa = Phe or Met
<220> FEATURE:
<221> NAME/KEY: VARIANT
<222> LOCATION: (15)...(15)
<223> OTHER INFORMATION: Xaa = Asp
<220> FEATURE:
<221> NAME/KEY: VARIANT
<222> LOCATION: (16)...(16)
<223> OTHER INFORMATION: Xaa = Tyr or Val

<400> SEQUENCE: 239

Xaa Xaa Xaa Xaa Xaa Xaa Xaa Xaa Xaa Xaa Xaa Xaa Xaa Xaa Xaa Xaa
 1               5                  10                  15

<210> SEQ ID NO 240
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(1)
<223> OTHER INFORMATION: Xaa = Gln
<220> FEATURE:
<221> NAME/KEY: VARIANT
<222> LOCATION: (2)...(2)
<223> OTHER INFORMATION: Xaa = Thr, Ser, Ala or Gly
<220> FEATURE:
<221> NAME/KEY: VARIANT
<222> LOCATION: (3)...(3)
<223> OTHER INFORMATION: Xaa = Ile
<220> FEATURE:
<221> NAME/KEY: VARIANT
<222> LOCATION: (4)...(4)
<223> OTHER INFORMATION: Xaa = Ser or Leu
<220> FEATURE:
<221> NAME/KEY: VARIANT
<222> LOCATION: (5)...(5)
<223> OTHER INFORMATION: Xaa = Tyr or absent
<220> FEATURE:
<221> NAME/KEY: VARIANT
<222> LOCATION: (6)...(6)
<223> OTHER INFORMATION: Xaa = Ser or absent
<220> FEATURE:
<221> NAME/KEY: VARIANT
<222> LOCATION: (7)...(7)
<223> OTHER INFORMATION: Xaa = Ser or absent
<220> FEATURE:
```

```
<221> NAME/KEY: VARIANT
<222> LOCATION: (8)...(8)
<223> OTHER INFORMATION: Xaa = Asn or absent
<220> FEATURE:
<221> NAME/KEY: VARIANT
<222> LOCATION: (9)...(9)
<223> OTHER INFORMATION: Xaa = Asn or absent
<220> FEATURE:
<221> NAME/KEY: VARIANT
<222> LOCATION: (10)...(10)
<223> OTHER INFORMATION: Xaa = Lys or absent
<220> FEATURE:
<221> NAME/KEY: VARIANT
<222> LOCATION: (11)...(11)
<223> OTHER INFORMATION: Xaa = Ser, Asn or Thr
<220> FEATURE:
<221> NAME/KEY: VARIANT
<222> LOCATION: (12)...(12)
<223> OTHER INFORMATION: Xaa = Trp or Tyr

<400> SEQUENCE: 240

Xaa Xaa Xaa Xaa Xaa Xaa Xaa Xaa Xaa Xaa Xaa Xaa
 1               5                  10

<210> SEQ ID NO 241
<211> LENGTH: 3
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(1)
<223> OTHER INFORMATION: Xaa = Ala, Trp or Ser
<220> FEATURE:
<221> NAME/KEY: VARIANT
<222> LOCATION: (2)...(2)
<223> OTHER INFORMATION: Xaa = Ala or Thr
<220> FEATURE:
<221> NAME/KEY: VARIANT
<222> LOCATION: (3)...(3)
<223> OTHER INFORMATION: Xaa = Ser

<400> SEQUENCE: 241

Xaa Xaa Xaa
 1

<210> SEQ ID NO 242
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(1)
<223> OTHER INFORMATION: Xaa =Gln
<220> FEATURE:
<221> NAME/KEY: VARIANT
<222> LOCATION: (2)...(2)
<223> OTHER INFORMATION: Xaa = Gln
<220> FEATURE:
<221> NAME/KEY: VARIANT
<222> LOCATION: (3)...(3)
<223> OTHER INFORMATION: Xaa = Tyr, Leu or Phe
<220> FEATURE:
<221> NAME/KEY: VARIANT
<222> LOCATION: (4)...(4)
<223> OTHER INFORMATION: Xaa = His, Tyr or Asn
<220> FEATURE:
<221> NAME/KEY: VARIANT
<222> LOCATION: (5)...(5)
<223> OTHER INFORMATION: Xaa = Arg or Ser
<220> FEATURE:
<221> NAME/KEY: VARIANT
<222> LOCATION: (6)...(6)
```

```
<223> OTHER INFORMATION: Xaa = Ser, Thr or Tyr
<220> FEATURE:
<221> NAME/KEY: VARIANT
<222> LOCATION: (7)...(7)
<223> OTHER INFORMATION: Xaa =Trp or Pro
<220> FEATURE:
<221> NAME/KEY: VARIANT
<222> LOCATION: (8)...(8)
<223> OTHER INFORMATION: Xaa = Phe, Leu or absent
<220> FEATURE:
<221> NAME/KEY: VARIANT
<222> LOCATION: (9)...(9)
<223> OTHER INFORMATION: Xaa = Thr

<400> SEQUENCE: 242

Xaa Xaa Xaa Xaa Xaa Xaa Xaa Xaa Xaa
 1               5

<210> SEQ ID NO 243
<211> LENGTH: 756
<212> TYPE: DNA
<213> ORGANISM: Homo sapiens

<400> SEQUENCE: 243
atggccgagg atctgggact gagctttggg gaaacagcca gtgtggaaat gctgccagag      60
cacggcagct gcaggcccaa ggccaggagc agcagcgcac gctgggctct cacctgctgc     120
ctggtgttgc tccccttcct tgcaggactc accacatacc tgcttgtcag ccagctccgg     180
gcccagggag aggcctgtgt gcagttccag gctctaaaag acaggagtt tgcaccttca      240 catcagcaag tttatgcacc tcttagagca gacggagata agccaagggc acacctgaca     300
gttgtgagac aaactcccac acagcacttt aaaaatcagt tcccagctct gcactgggaa     360
catgaactag gcctggcctt caccaagaac cgaatgaact ataccaacaa attcctgctg     420
atcccagagt cgggagacta cttcatttac tcccaggtca cattccgtgg gatgacctct     480
gagtgcagtg aaatcagaca agcaggccga ccaaacaagc cagactccat cactgtggtc     540
atcaccaagg taacagacag ctaccctgag ccaacccagc tcctcatggg gaccaagtct     600
gtatgcgaag taggtagcaa ctggttccag cccatctacc tcggagccat gttctccttg     660
caagaagggg acaagctaat ggtgaacgtc agtgacatct ctttggtgga ttacacaaaa     720
gaagataaaa ccttctttgg agccttctta ctatag                              756

<210> SEQ ID NO 244
<211> LENGTH: 251
<212> TYPE: PRT
<213> ORGANISM: Homo sapiens

<400> SEQUENCE: 244

Met Ala Glu Asp Leu Gly Leu Ser Phe Gly Glu Thr Ala Ser Val Glu
 1               5                   10                  15

Met Leu Pro Glu His Gly Ser Cys Arg Pro Lys Ala Arg Ser Ser Ser
                20                  25                  30

Ala Arg Trp Ala Leu Thr Cys Cys Leu Val Leu Pro Phe Leu Ala
        35                  40                  45

Gly Leu Thr Thr Tyr Leu Leu Val Ser Gln Leu Arg Ala Gln Gly Glu
    50                  55                  60

Ala Cys Val Gln Phe Gln Ala Leu Lys Gly Gln Glu Phe Ala Pro Ser
65                  70                  75                  80

His Gln Gln Val Tyr Ala Pro Leu Arg Ala Asp Gly Asp Lys Pro Arg
                85                  90                  95

Ala His Leu Thr Val Val Arg Gln Thr Pro Thr Gln His Phe Lys Asn
```

```
              100                 105                 110
Gln Phe Pro Ala Leu His Trp Glu His Glu Leu Gly Leu Ala Phe Thr
        115                 120                 125
Lys Asn Arg Met Asn Tyr Thr Asn Lys Phe Leu Leu Ile Pro Glu Ser
130                 135                 140
Gly Asp Tyr Phe Ile Tyr Ser Gln Val Thr Phe Arg Gly Met Thr Ser
145                 150                 155                 160
Glu Cys Ser Glu Ile Arg Gln Ala Gly Arg Pro Asn Lys Pro Asp Ser
                165                 170                 175
Ile Thr Val Val Ile Thr Lys Val Thr Asp Ser Tyr Pro Glu Pro Thr
            180                 185                 190
Gln Leu Leu Met Gly Thr Lys Ser Val Cys Glu Val Gly Ser Asn Trp
        195                 200                 205
Phe Gln Pro Ile Tyr Leu Gly Ala Met Phe Ser Leu Gln Glu Gly Asp
    210                 215                 220
Lys Leu Met Val Asn Val Ser Asp Ile Ser Leu Val Asp Tyr Thr Lys
225                 230                 235                 240
Glu Asp Lys Thr Phe Phe Gly Ala Phe Leu Leu
                245                 250

<210> SEQ ID NO 245
<211> LENGTH: 756
<212> TYPE: DNA
<213> ORGANISM: Homo sapiens

<400> SEQUENCE: 245
atggccgagg atctgggact gagctttggg gaaacagcca gtgtggaaat gctgccagag    60
cacggcagct gcaggcccaa ggccaggagc agcagcgcac gctgggctct cacctgctgc   120
ctggtgttgc tccccttcct tgcaggactc accacatacc tgcttgtcag ccagctccgg   180
gcccagggag aggcctgtgt gcagttccag gctctaaaag acaggagtt tgcaccttca    240 catcagcaag tttatgcacc tcttagagca gacggagata agccaagggc acacctgaca   300
gttgtgagac aaactcccac acagcacttt aaaaatcagt tcccagctct gcactgggaa   360
catgaactag gcctggcctt caccaagaac cgaatgaact ataccaacaa attcctgctg   420
atcccagagt cgggagacta cttcatttac tcccaggtca cattccgtgg gatgacctct   480
gagtgcagtg aaatcagacg agcaggccga ccaaacaagc cagactccat cactgtggtc   540
atcaccaagg taacagacag ctaccctgag ccaacccagc tcctcatggg gaccaagtct   600
gtatgcgaag taggtagcaa ctggttccag cccatctacc tcggagccat gttctccttg   660
caagaagggg acaagctaat ggtgaacgtc agtgacatct ctttggtgga ttacacaaaa   720
gaagataaaa ccttctttgg agccttctta ctatag                             756

<210> SEQ ID NO 246
<211> LENGTH: 251
<212> TYPE: PRT
<213> ORGANISM: Homo sapiens

<400> SEQUENCE: 246

Met Ala Glu Asp Leu Gly Leu Ser Phe Gly Glu Thr Ala Ser Val Glu
1               5                   10                  15
Met Leu Pro Glu His Gly Ser Cys Arg Pro Lys Ala Arg Ser Ser Ser
            20                  25                  30
Ala Arg Trp Ala Leu Thr Cys Cys Leu Val Leu Leu Pro Phe Leu Ala
        35                  40                  45
```

| | | | | | | | | | | | |
|---|---|---|---|---|---|---|---|---|---|---|---|
|Gly|Leu|Thr|Thr|Tyr|Leu|Leu|Val|Ser|Gln|Leu|Arg|Ala|Gln|Gly|Glu|
|50| | | | |55| | | | |60| | | | | |

Ala Cys Val Gln Phe Gln Ala Leu Lys Gly Gln Glu Phe Ala Pro Ser
65                  70                  75                  80

His Gln Gln Val Tyr Ala Pro Leu Arg Ala Asp Gly Asp Lys Pro Arg
                85                  90                  95

Ala His Leu Thr Val Val Arg Gln Thr Pro Thr Gln His Phe Lys Asn
            100                 105                 110

Gln Phe Pro Ala Leu His Trp Glu His Glu Leu Gly Leu Ala Phe Thr
        115                 120                 125

Lys Asn Arg Met Asn Tyr Thr Asn Lys Phe Leu Leu Ile Pro Glu Ser
130                 135                 140

Gly Asp Tyr Phe Ile Tyr Ser Gln Val Thr Phe Arg Gly Met Thr Ser
145                 150                 155                 160

Glu Cys Ser Glu Ile Arg Arg Ala Gly Arg Pro Asn Lys Pro Asp Ser
                165                 170                 175

Ile Thr Val Val Ile Thr Lys Val Thr Asp Ser Tyr Pro Glu Pro Thr
            180                 185                 190

Gln Leu Leu Met Gly Thr Lys Ser Val Cys Glu Val Gly Ser Asn Trp
        195                 200                 205

Phe Gln Pro Ile Tyr Leu Gly Ala Met Phe Ser Leu Gln Glu Gly Asp
    210                 215                 220

Lys Leu Met Val Asn Val Ser Asp Ile Ser Leu Val Asp Tyr Thr Lys
225                 230                 235                 240

Glu Asp Lys Thr Phe Phe Gly Ala Phe Leu Leu
                245                 250

<210> SEQ ID NO 247
<211> LENGTH: 756
<212> TYPE: DNA
<213> ORGANISM: Macaca fascicularis

<400> SEQUENCE: 247

| | | |
|---|---|---|
|atggccgagg atctgggact gagctttggg gagacagcca gtgtggaaat gctgccagag|60|
|cacggcagct gcaggcccaa ggccaggagc agcagcgcat gctgggctct cacctgctgc|120|
|ctggtgttgc tccccttcct tgcagggctc accacctacc tgcttgtcag ccagctccgg|180|
|gcccaaggag aggcctgtgt gcagctccag gatctaaaag gacaggagtt tgcaccttca|240|
|catcagcaag tttatgcacc tcttagagca gatggagata agccaagggc acacctgaca|300|
|gttgtgagac aaactcccac acagcactta aaaaatcagt tcccagctct gcactgggaa|360|
|catgaactag gcctggcctt caccaagaac cgaatgaact acaccaacaa attcctgctg|420|
|atcccagagt cgggagacta cttcgtttac tcccaggtca cattccgtgg gatgacctct|480|
|gagtgcagtg aaatcagaca gcaggccga ccaaacaagc cagactccat cactgtggtc|540|
|atcaccaagg taacagacag ctaccctgag ccaacccagc tcctcatggg gaccaagtct|600|
|gtgtgtgaag taggcagtaa ctggttccag cccatctacc tcggagccat gttctccttg|660|
|caagaagggg acaagctcat ggtgaacgtc agtgacatct ctttggtgga ttacacaaaa|720|
|gaagataaaa ccttctttgg agccttctta ctatag|756|

<210> SEQ ID NO 248
<211> LENGTH: 251
<212> TYPE: PRT
<213> ORGANISM: Macaca fascicularis

<400> SEQUENCE: 248

Met Ala Glu Asp Leu Gly Leu Ser Phe Gly Glu Thr Ala Ser Val Glu
 1               5                  10                 15
Met Leu Pro Glu His Gly Ser Cys Arg Pro Lys Ala Arg Ser Ser Ser
             20                  25                  30
Ala Cys Trp Ala Leu Thr Cys Cys Leu Val Leu Pro Phe Leu Ala
         35                  40                  45
Gly Leu Thr Thr Tyr Leu Leu Val Ser Gln Leu Arg Ala Gln Gly Glu
 50                  55                  60
Ala Cys Val Gln Leu Gln Asp Leu Lys Gly Gln Glu Phe Ala Pro Ser
 65              70                  75                  80
His Gln Gln Val Tyr Ala Pro Leu Arg Ala Asp Gly Asp Lys Pro Arg
             85                  90                  95
Ala His Leu Thr Val Val Arg Gln Thr Pro Thr Gln His Leu Lys Asn
             100                 105                 110
Gln Phe Pro Ala Leu His Trp Glu His Glu Leu Gly Leu Ala Phe Thr
             115                 120                 125
Lys Asn Arg Met Asn Tyr Thr Asn Lys Phe Leu Leu Ile Pro Glu Ser
 130                 135                 140
Gly Asp Tyr Phe Val Tyr Ser Gln Val Thr Phe Arg Gly Met Thr Ser
 145                 150                 155                 160
Glu Cys Ser Glu Ile Arg Gln Ala Gly Arg Pro Asn Lys Pro Asp Ser
             165                 170                 175
Ile Thr Val Val Ile Thr Lys Val Thr Asp Ser Tyr Pro Glu Pro Thr
             180                 185                 190
Gln Leu Leu Met Gly Thr Lys Ser Val Cys Glu Val Gly Ser Asn Trp
             195                 200                 205
Phe Gln Pro Ile Tyr Leu Gly Ala Met Phe Ser Leu Gln Glu Gly Asp
             210                 215                 220
Lys Leu Met Val Asn Val Ser Asp Ile Ser Leu Val Asp Tyr Thr Lys
 225                 230                 235                 240
Glu Asp Lys Thr Phe Phe Gly Ala Phe Leu Leu
             245                 250

<210> SEQ ID NO 249
<211> LENGTH: 759
<212> TYPE: DNA
<213> ORGANISM: Mus musculus

<400> SEQUENCE: 249
atggcagagg agctggggtt gggcttcgga gaaggagtcc cagtggaagt gctgccggaa     60
ggctgtagac acaggccaga ggccagggcc gggctagctg ccaggagcaa agcctgcctg    120
gctctcacct gctgcctgtt gtcatttccc atcctcgcag acttagcac cctcctaatg    180 gctggccagc tccgggtccc cggaaaagac tgtatgcttc gggccataac agaagagaga    240
tctgagcctt caccacagca agtttactca cctcccagag gcaagccgag agcacacctg    300
acaattaaga acaaacccc agcaccacat ctgaaaaatc agctctctgc tctacactgg    360
gaacatgacc tagggatggc cttcaccaag aacgggatga gtacatcaa caaatccctg    420 gtgatcccag agtcaggaga ctatttcatc tactcccaga tcacattccg agggaccaca    480
tctgtgtgtg tgacatcag tcggggggaga cgaccaaaca agccagactc catcaccatg    540
gttatcacca aggtagcaga cagctaccct gagcctgccc gcctactaac agggtccaag    600
tctgtgtgtg aaataagcaa caactggttc cagtccctct accttgggc cacgttctcc    660 ttggaagaag gagacagact aatggtaaac gtcagtgaca tctccttggt ggattacaca    720
aaagaagata aaactttctt tggagctttc ttgctataa                759

<210> SEQ ID NO 250
<211> LENGTH: 252
<212> TYPE: PRT
<213> ORGANISM: Mus musculus

<400> SEQUENCE: 250

Met Ala Glu Glu Leu Gly Leu Gly Phe Gly Glu Gly Val Pro Val Glu
1               5                   10                  15

Val Leu Pro Glu Gly Cys Arg His Arg Pro Glu Ala Arg Ala Gly Leu
            20                  25                  30

Ala Ala Arg Ser Lys Ala Cys Leu Ala Leu Thr Cys Cys Leu Leu Ser
        35                  40                  45

Phe Pro Ile Leu Ala Gly Leu Ser Thr Leu Leu Met Ala Gly Gln Leu
    50                  55                  60

Arg Val Pro Gly Lys Asp Cys Met Leu Arg Ala Ile Thr Glu Glu Arg
65                  70                  75                  80

Ser Glu Pro Ser Pro Gln Gln Val Tyr Ser Pro Pro Arg Gly Lys Pro
                85                  90                  95

Arg Ala His Leu Thr Ile Lys Lys Gln Thr Pro Ala Pro His Leu Lys
            100                 105                 110

Asn Gln Leu Ser Ala Leu His Trp Glu His Asp Leu Gly Met Ala Phe
        115                 120                 125

Thr Lys Asn Gly Met Lys Tyr Ile Asn Lys Ser Leu Val Ile Pro Glu
    130                 135                 140

Ser Gly Asp Tyr Phe Ile Tyr Ser Gln Ile Thr Phe Arg Gly Thr Thr
145                 150                 155                 160

Ser Val Cys Gly Asp Ile Ser Arg Gly Arg Arg Pro Asn Lys Pro Asp
                165                 170                 175

Ser Ile Thr Met Val Ile Thr Lys Val Ala Asp Ser Tyr Pro Glu Pro
            180                 185                 190

Ala Arg Leu Leu Thr Gly Ser Lys Ser Val Cys Glu Ile Ser Asn Asn
        195                 200                 205

Trp Phe Gln Ser Leu Tyr Leu Gly Ala Thr Phe Ser Leu Glu Glu Gly
    210                 215                 220

Asp Arg Leu Met Val Asn Val Ser Asp Ile Ser Leu Val Asp Tyr Thr
225                 230                 235                 240

Lys Glu Asp Lys Thr Phe Phe Gly Ala Phe Leu Leu
                245                 250

<210> SEQ ID NO 251
<211> LENGTH: 1254
<212> TYPE: DNA
<213> ORGANISM: Homo sapiens

<400> SEQUENCE: 251
atggagcagc ggccgcgggg ctgcgcggcg gtggcggcgg cgctcctcct ggtgctgctg     60
ggggcccggg cccagggcgg cactcgtagc cccaggtgtg actgtgccgg tgacttccac    120
aagaagattg gtctgttttg ttgcagaggc tgcccagcgg ggcactacct gaaggcccct    180
tgcacggagc cctgcggcaa ctccacctgc cttgtgtgtc cccaagacac cttcttggcc    240
tgggagaacc accataattc tgaatgtgcc cgctgccagg cctgtgatga gcaggcctcc    300
caggtggcgc tggagaactg ttcagcagtg gccgacaccc gctgtggctg taagccaggc    360
tggtttgtgg agtgccaggt cagccaatgt gtcagcagtt cacccttcta ctgccaacca    420

```
tgcctagact gcggggccct gcaccgccac acacggctac tctgttcccg cagagatact    480
gactgtggga cctgcctgcc tggcttctat gaacatggcg atggctgcgt gtcctgcccc    540
acgagcaccc tggggagctg tccagagcgc tgtgccgctg tctgtggctg gaggcagatg    600
ttctgggtcc aggtgctcct ggctggcctt gtggtccccc tcctgcttgg ggccaccctg    660
acctacacat accgccactg ctggcctcac aagcccctgg ttactgcaga tgaagctggg    720
atggaggctc tgaccccacc accggccacc catctgtcac ccttggacag cgcccacacc    780
cttctagcac ctcctgacag cagtgagaag atctgcaccg tccagttggt gggtaacagc    840 tggaccccctg gctaccccga gacccaggag gcgctctgcc cgcaggtgac atggtcctgg    900
gaccagttgc ccagcagagc tcttggcccc gctgctgcgc ccacactctc gccagagtcc    960
ccagccggct cgccagccat gatgctgcag ccggccccgc agctctacga cgtgatggac   1020
gcggtcccag cgcggcgctg gaaggagttc gtgcgcacgc tggggctgcg cgaggcagag   1080
atcgaagccg tggaggtgga gatcggccgc ttccgagacc agcagtacga gatgctcaag   1140
cgctggcgcc agcagcagcc cgcgggcctc ggagccgttt acgcggccct ggagcgcatg   1200
gggctggacg gctgcgtgga agacttgcgc agccgcctgc agcgcggccc gtga         1254
```

<210> SEQ ID NO 252
<211> LENGTH: 417
<212> TYPE: PRT
<213> ORGANISM: Homo sapiens

<400> SEQUENCE: 252

```
Met Glu Gln Arg Pro Arg Gly Cys Ala Ala Val Ala Ala Ala Leu Leu
 1               5                  10                  15

Leu Val Leu Leu Gly Ala Arg Ala Gln Gly Gly Thr Arg Ser Pro Arg
            20                  25                  30

Cys Asp Cys Ala Gly Asp Phe His Lys Lys Ile Gly Leu Phe Cys Cys
        35                  40                  45

Arg Gly Cys Pro Ala Gly His Tyr Leu Lys Ala Pro Cys Thr Glu Pro
    50                  55                  60

Cys Gly Asn Ser Thr Cys Leu Val Cys Pro Gln Asp Thr Phe Leu Ala
65                  70                  75                  80

Trp Glu Asn His His Asn Ser Glu Cys Ala Arg Cys Gln Ala Cys Asp
                85                  90                  95

Glu Gln Ala Ser Gln Val Ala Leu Glu Asn Cys Ser Ala Val Ala Asp
            100                 105                 110

Thr Arg Cys Gly Cys Lys Pro Gly Trp Phe Val Glu Cys Gln Val Ser
        115                 120                 125

Gln Cys Val Ser Ser Pro Phe Tyr Cys Gln Pro Cys Leu Asp Cys
    130                 135                 140

Gly Ala Leu His Arg His Thr Arg Leu Leu Cys Ser Arg Arg Asp Thr
145                 150                 155                 160

Asp Cys Gly Thr Cys Leu Pro Gly Phe Tyr Glu His Gly Asp Gly Cys
                165                 170                 175

Val Ser Cys Pro Thr Ser Thr Leu Gly Ser Cys Pro Glu Arg Cys Ala
            180                 185                 190

Ala Val Cys Gly Trp Arg Gln Met Phe Trp Val Gln Val Leu Leu Ala
        195                 200                 205

Gly Leu Val Val Pro Leu Leu Leu Gly Ala Thr Leu Thr Tyr Thr Tyr
    210                 215                 220

Arg His Cys Trp Pro His Lys Pro Leu Val Thr Ala Asp Glu Ala Gly
```

```
            225                 230                 235                 240
Met Glu Ala Leu Thr Pro Pro Ala Thr His Leu Ser Pro Leu Asp
                245                 250                 255

Ser Ala His Thr Leu Leu Ala Pro Pro Asp Ser Ser Glu Lys Ile Cys
            260                 265                 270

Thr Val Gln Leu Val Gly Asn Ser Trp Thr Pro Gly Tyr Pro Glu Thr
        275                 280                 285

Gln Glu Ala Leu Cys Pro Gln Val Thr Trp Ser Trp Asp Gln Leu Pro
        290                 295                 300

Ser Arg Ala Leu Gly Pro Ala Ala Ala Pro Thr Leu Ser Pro Glu Ser
305                 310                 315                 320

Pro Ala Gly Ser Pro Ala Met Met Leu Gln Pro Gly Pro Gln Leu Tyr
                325                 330                 335

Asp Val Met Asp Ala Val Pro Ala Arg Arg Trp Lys Glu Phe Val Arg
                340                 345                 350

Thr Leu Gly Leu Arg Glu Ala Glu Ile Glu Ala Val Glu Val Glu Ile
            355                 360                 365

Gly Arg Phe Arg Asp Gln Gln Tyr Glu Met Leu Lys Arg Trp Arg Gln
        370                 375                 380

Gln Gln Pro Ala Gly Leu Gly Ala Val Tyr Ala Ala Leu Glu Arg Met
385                 390                 395                 400

Gly Leu Asp Gly Cys Val Glu Asp Leu Arg Ser Arg Leu Gln Arg Gly
                405                 410                 415

Pro

<210> SEQ ID NO 253
<211> LENGTH: 900
<212> TYPE: DNA
<213> ORGANISM: Homo sapiens

<400> SEQUENCE: 253
atgagggcgc tggaggggcc aggcctgtcg ctgctgtgcc tggtgttggc gctgcctgcc      60
ctgctgccgg tgccggctgt acgcggagtg gcagaaacac ccacctaccc ctggcgggac     120
gcagagacag gggagcggct ggtgtgcgcc cagtgccccc aggcaccctt gtgcagcgg      180 ccgtgccgcc gagacagccc cacgacgtgt ggcccgtgtc accgcgccac ctacacgcag     240
ttctggaact acctggagcg ctgccgctac tgcaacgtcc tctgcgggga gcgtgaggag     300
gaggcacggg cttgccacgc cacccacaac cgtgcctgcc gctgccgcac cggcttcttc     360
gcgcacgctg gtttctgctt ggagcacgca tcgtgtccac ctggtgccgg cgtgattgcc     420
ccgggcaccc ccagccagaa cacgcagtgc agccgtgcc ccccaggcac cttctcagcc      480
agcagctcca gctcagagca gtgccagccc caccgcaact gcacggccct gggcctggcc     540
ctcaatgtgc caggctcttc ctcccatgac accctgtgca ccagctgcac tggcttcccc     600
ctcagcacca gggtaccagg agctgaggag tgtgagcgtg ccgtcatcga ctttgtggct     660
ttccaggaca tctccatcaa gaggctgcag cggctgctgc aggccctcga ggccccggag     720
ggctggggtc cgacaccaag gcgggccgc gcggccttgc agctgaagct gcgtcggcgg      780
ctcacggagc tcctgggggc gcaggacggg gcgctgctgg tgcggctgct gcaggcgctg     840
cgcgtggcca ggatgcccgg gctggagcgg agcgtccgtg agcgcttcct ccctgtgcac     900

<210> SEQ ID NO 254
<211> LENGTH: 300
<212> TYPE: PRT
<213> ORGANISM: Homo sapiens
```

```
<400> SEQUENCE: 254

Met Arg Ala Leu Glu Gly Pro Gly Leu Ser Leu Leu Cys Leu Val Leu
 1               5                  10                  15

Ala Leu Pro Ala Leu Leu Pro Val Pro Ala Val Arg Gly Val Ala Glu
             20                  25                  30

Thr Pro Thr Tyr Pro Trp Arg Asp Ala Glu Thr Gly Glu Arg Leu Val
         35                  40                  45

Cys Ala Gln Cys Pro Pro Gly Thr Phe Val Gln Arg Pro Cys Arg Arg
 50                  55                  60

Asp Ser Pro Thr Thr Cys Gly Pro Cys Pro Pro Arg His Tyr Thr Gln
 65                  70                  75                  80

Phe Trp Asn Tyr Leu Glu Arg Cys Arg Tyr Cys Asn Val Leu Cys Gly
                 85                  90                  95

Glu Arg Glu Glu Glu Ala Arg Ala Cys His Ala Thr His Asn Arg Ala
            100                 105                 110

Cys Arg Cys Arg Thr Gly Phe Phe Ala His Ala Gly Phe Cys Leu Glu
            115                 120                 125

His Ala Ser Cys Pro Pro Gly Ala Gly Val Ile Ala Pro Gly Thr Pro
        130                 135                 140

Ser Gln Asn Thr Gln Cys Gln Pro Cys Pro Pro Gly Thr Phe Ser Ala
145                 150                 155                 160

Ser Ser Ser Ser Ser Glu Cys Gln Pro His Arg Asn Cys Thr Ala
                165                 170                 175

Leu Gly Leu Ala Leu Asn Val Pro Gly Ser Ser His Asp Thr Leu
        180                 185                 190

Cys Thr Ser Cys Thr Gly Phe Pro Leu Ser Thr Arg Val Pro Gly Ala
        195                 200                 205

Glu Glu Cys Glu Arg Ala Val Ile Asp Phe Val Ala Phe Gln Asp Ile
        210                 215                 220

Ser Ile Lys Arg Leu Gln Arg Leu Leu Gln Ala Leu Glu Ala Pro Glu
225                 230                 235                 240

Gly Trp Gly Pro Thr Pro Arg Ala Gly Arg Ala Ala Leu Gln Leu Lys
                245                 250                 255

Leu Arg Arg Arg Leu Thr Glu Leu Leu Gly Ala Gln Asp Gly Ala Leu
            260                 265                 270

Leu Val Arg Leu Leu Gln Ala Leu Arg Val Ala Arg Met Pro Gly Leu
        275                 280                 285

Glu Arg Ser Val Arg Glu Arg Phe Leu Pro Val His
        290                 295                 300

<210> SEQ ID NO 255
<211> LENGTH: 330
<212> TYPE: PRT
<213> ORGANISM: Artificial Sequence
<220> FEATURE:
<223> OTHER INFORMATION: Synthetic

<400> SEQUENCE: 255

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
```

-continued

```
                50                  55                  60
Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                     85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
                115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
                290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

```
<210> SEQ ID NO 256
<211> LENGTH: 327
<212> TYPE: PRT
<213> ORGANISM: Artificial Sequence
<220> FEATURE:
<223> OTHER INFORMATION: Synthetic

<400> SEQUENCE: 256

Ala Ser Thr Lys Gly Pro Ser Val Phe Pro Leu Ala Pro Cys Ser Arg
  1               5                  10                  15

Ser Thr Ser Glu Ser Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
         50                  55                  60

Leu Ser Ser Val Val Thr Val Pro Ser Ser Leu Gly Thr Lys Thr
 65                  70                  75                  80

Tyr Thr Cys Asn Val Asp His Lys Pro Ser Asn Thr Lys Val Asp Lys
                     85                  90                  95
```

```
Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 257
<211> LENGTH: 327
<212> TYPE: PRT
<213> ORGANISM: Artificial Sequence
<220> FEATURE:
<223> OTHER INFORMATION: Synthetic

<400> SEQUENCE: 257

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
            115                 120                 125
```

```
Asp Thr Leu Met Ile Ser Arg Thr Pro Glu Val Thr Cys Val Val Val
            130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 258
<211> LENGTH: 252
<212> TYPE: PRT
<213> ORGANISM: Rattus norvegicus

<400> SEQUENCE: 258

Met Ala Glu Glu Leu Gly Leu Gly Phe Gly Glu Ala Val Pro Val Glu
1               5                   10                  15

Met Leu Pro Glu Gly Cys Arg His Arg Arg Glu Ala Arg Thr Gly Leu
            20                  25                  30

Ala Ala Arg Ser Lys Ala Cys Leu Ala Leu Thr Cys Cys Leu Leu Ser
        35                  40                  45

Phe Pro Ile Leu Ala Gly Leu Ser Thr Leu Leu Met Thr Gly Gln Leu
50                  55                  60

Arg Ile Pro Gly Lys Asp Cys Met Phe Pro Thr Val Thr Glu Glu Arg
65                  70                  75                  80

Ser Ala Pro Ser Ala Gln Pro Val Tyr Thr Pro Ser Arg Asp Lys Pro
                85                  90                  95

Lys Ala His Leu Thr Ile Met Arg Gln Thr Pro Val Pro His Leu Lys
            100                 105                 110

Asn Glu Leu Ala Ala Leu His Trp Glu Asn Asn Leu Gly Met Ala Phe
        115                 120                 125

Thr Lys Asn Arg Met Asn Tyr Thr Asn Lys Phe Leu Val Ile Pro Glu
130                 135                 140

Ser Gly Asp Tyr Phe Ile Tyr Ser Gln Ile Thr Phe Arg Gly Thr Thr
145                 150                 155                 160

Ser Glu Cys Gly Asp Ile Ser Arg Val Arg Arg Pro Lys Pro Lys Asp
                165                 170                 175
```

```
Ser Ile Thr Val Val Ile Thr Lys Val Ala Asp Ser Tyr Pro Glu Pro
                180                 185                 190

Ala His Leu Leu Thr Gly Thr Lys Ser Val Cys Glu Ile Ser Ser Asn
                195                 200                 205

Trp Phe Gln Pro Ile Tyr Leu Gly Ala Met Phe Ser Leu Glu Glu Gly
210                 215                 220

Asp Arg Leu Met Val Asn Val Ser Asp Ile Ser Leu Val Asp Tyr Thr
225                 230                 235                 240

Lys Glu Asp Lys Thr Phe Phe Gly Ala Phe Leu Ile
                245                 250

<210> SEQ ID NO 259
<211> LENGTH: 411
<212> TYPE: PRT
<213> ORGANISM: Mus musculus

<400> SEQUENCE: 259

Met Glu Ala Arg Leu Leu Arg Gly Cys Val Val Glu Pro Leu Phe Leu
1               5                   10                  15

Pro Leu Leu Leu Leu Leu Leu Leu Leu Gly Gly Gln Gly Gln Gly
                20                  25                  30

Gly Met Ser Gly Arg Cys Asp Cys Ala Ser Glu Ser Gln Lys Arg Tyr
                35                  40                  45

Gly Pro Phe Cys Cys Arg Gly Cys Pro Lys Gly His Tyr Met Lys Ala
50                  55                  60

Pro Cys Ala Glu Pro Cys Gly Asn Ser Thr Cys Leu Pro Cys Pro Ser
65                  70                  75                  80

Asp Thr Phe Leu Thr Arg Asp Asn His Phe Lys Thr Asp Cys Thr Arg
                85                  90                  95

Cys Gln Val Cys Asp Glu Gly Ala Leu Gln Val Thr Leu Glu Asn Cys
                100                 105                 110

Ser Ala Lys Ser Asp Thr His Cys Gly Cys Ser Gly Trp Cys Val
                115                 120                 125

Asp Cys Ser Thr Glu Pro Cys Gly Lys Ser Ser Pro Phe Ser Cys Val
130                 135                 140

Pro Cys Gly Ala Thr Thr Pro Val His Glu Ala Pro Thr Pro Arg Pro
145                 150                 155                 160

Cys Leu Pro Gly Phe Tyr Ile Arg Gly Asn Asp Cys Thr Ser Cys Pro
                165                 170                 175

Thr Gly Phe Ser Ser Val Cys Pro Lys Ala Cys Thr Ala Val Cys Gly
                180                 185                 190

Trp Lys Gln Met Phe Trp Val Gln Val Leu Leu Gly Val Ala Phe Leu
                195                 200                 205

Phe Gly Ala Ile Leu Ile Cys Ala Tyr Cys Arg Trp Gln Pro Cys Lys
210                 215                 220

Ala Val Val Thr Ala Asp Thr Ala Gly Thr Glu Thr Leu Ala Ser Pro
225                 230                 235                 240

Gln Thr Ala His Leu Ser Ala Ser Asp Ser Ala His Thr Leu Leu Ala
                245                 250                 255

Pro Pro Ser Ser Thr Gly Lys Ile Cys Thr Val Gln Leu Val Gly
                260                 265                 270

Asn Asn Trp Thr Pro Gly Leu Ser Gln Thr Gln Glu Val Val Cys Gly
                275                 280                 285

Gln Ala Ser Gln Pro Trp Asp Gln Leu Pro Asn Arg Thr Leu Gly Thr
290                 295                 300
```

-continued

| | | | | | | | | | | | | | | | |
|---|---|---|---|---|---|---|---|---|---|---|---|---|---|---|---|
| Pro 305 | Leu | Ala | Ser | Pro 310 | Leu | Ser | Pro | Ala 315 | Pro | Pro | Ala | Gly | Ser | Pro | Ala 320 |
| Ala | Val | Leu | Gln | Pro 325 | Gly | Pro | Gln | Leu 330 | Tyr | Asp | Val | Met | Asp | Ala 335 | Val |
| Pro | Ala | Arg | Arg 340 | Trp | Lys | Glu | Phe | Val 345 | Arg | Thr | Leu | Gly | Leu 350 | Arg | Glu |
| Ala | Glu | Ile 355 | Glu | Ala | Val | Glu | Val 360 | Glu | Ile | Cys | Arg | Phe 365 | Arg | Asp | Gln |
| Gln | Tyr 370 | Glu | Met | Leu | Lys | Arg 375 | Trp | Arg | Gln | Gln | Pro 380 | Ala | Gly | Leu | |
| Gly 385 | Ala | Ile | Tyr | Ala | Ala 390 | Leu | Glu | Arg | Met | Gly 395 | Leu | Glu | Gly | Cys | Ala 400 |
| Glu | Asp | Leu | Arg | Ser 405 | Arg | Leu | Gln | Arg | Gly 410 | Pro | | | | | |